(12) United States Patent
Redlich et al.

(10) Patent No.: US 7,322,047 B2
(45) Date of Patent: *Jan. 22, 2008

(54) DATA SECURITY SYSTEM AND METHOD ASSOCIATED WITH DATA MINING

(75) Inventors: Ron M. Redlich, Miami Beach, FL (US); Martin A. Nemzow, Miami Beach, FL (US)

(73) Assignee: Digital Doors, Inc., Miami Beach, FL (US)

( * ) Notice: Subject to any disclaimer, the term of this patent is extended or adjusted under 35 U.S.C. 154(b) by 798 days.
This patent is subject to a terminal disclaimer.

(21) Appl. No.: 10/277,196

(22) Filed: Dec. 31, 2002

(65) Prior Publication Data

US 2003/0120949 A1 Jun. 26, 2003

Related U.S. Application Data

(63) Continuation-in-part of application No. 10/155,192, filed on May 23, 2002, and a continuation-in-part of application No. 10/155,525, filed on May 23, 2002, now Pat. No. 7,191,252, and a continuation-in-part of application No. 10/008,209, filed on Dec. 6, 2001, now Pat. No. 7,140,044, and a continuation-in-part of application No. 10/008,218, filed on Dec. 6, 2001, now Pat. No. 7,146,644, and a continuation-in-part of application No. 09/916,397, filed on Jul. 27, 2001, now Pat. No. 7,103,915.

(60) Provisional application No. 60/400,062, filed on Aug. 2, 2002, provisional application No. 60/400,112, filed on Aug. 2, 2002, provisional application No. 60/400,406, filed on Aug. 2, 2002, provisional application No. 60/400,407, filed on Aug. 2, 2002, provisional application No. 60/260,398, filed on Jan. 9, 2001, provisional application No. 60/287,813, filed on May 2, 2001, provisional application No. 60/267,944, filed on Feb. 12, 2001, provisional application No. 60/247,242, filed on Nov. 13, 2000, provisional application No. 60/247,232, filed on Nov. 13, 2000.

(51) Int. Cl.
*G06F 7/00* (2006.01)
*G06F 17/00* (2006.01)
*H04L 9/14* (2006.01)

(52) U.S. Cl. .............. 726/27; 713/166; 713/193; 715/530; 715/540

(58) Field of Classification Search ............ 726/27; 713/166, 193; 715/530, 540, 751; 709/229
See application file for complete search history.

(56) References Cited

U.S. PATENT DOCUMENTS 5,036,315 A 7/1991 Gurley .................. 340/721

(Continued)

FOREIGN PATENT DOCUMENTS

WO WO 9953624 A1 * 10/1999

(Continued)

OTHER PUBLICATIONS

Ingram i100, Content Security Appliance (2 pages), printed Jun. 24, 2001.

(Continued)

*Primary Examiner*—Emmanuel L. Moise
*Assistant Examiner*—Michael Pyzocha
(74) *Attorney, Agent, or Firm*—Robert C. Kain, Jr.; Fleit Kain

(57) ABSTRACT

The data security method, system and associated data mining enables multiple users, each having a respective security clearance level to access security sensitive words, data objects, characters or icons. The method extracts security sensitive words, data objects, characters or icons from plaintext or other source documents to obtain (a) subsets of extracted data and (b) remainder data. The extracted data is, in one embodiment, stored in a multilevel security system (MLS) which separates extract data of different security levels with MLS guards. Some or all of the original data is reconstructed via one or more of the subsets of extracted data and remainder data only in the presence of a predetermined security level. In this manner, an inquiring party, with the proper security clearance, can data mine the data in the MLS secured storage.

90 Claims, 18 Drawing Sheets

U.S. PATENT DOCUMENTS

| | | | | |
|---|---|---|---|---|
| 5,423,032 | A | 6/1995 | Byrd et al. | 395/600 |
| 5,485,474 | A | 1/1996 | Rabin | 371/37.1 |
| 5,532,950 | A | 7/1996 | Moses | 364/724.19 |
| 5,581,682 | A * | 12/1996 | Anderson et al. | 715/530 |
| 5,715,399 | A | 2/1998 | Bezos | 395/227 |
| 5,757,916 | A | 5/1998 | MacDoran et al. | 380/25 |
| 5,778,304 | A | 7/1998 | Grube et al. | 455/33.1 |
| 5,832,212 | A | 11/1998 | Cragun et al. | 395/188.01 |
| 5,842,023 | A | 11/1998 | Tsumura | 395/712 |
| 5,871,398 | A * | 2/1999 | Schneier et al. | 463/16 |
| 5,887,269 | A | 3/1999 | Brunts et al. | 701/208 |
| 5,892,908 | A | 4/1999 | Hughes et al. | 395/200.8 |
| 5,905,980 | A | 5/1999 | Masuichi et al. | 707/1 |
| 5,933,498 | A | 8/1999 | Schneck et al. | 380/4 |
| 5,960,080 | A * | 9/1999 | Fahlman et al. | 380/252 |
| 5,982,897 | A | 11/1999 | Clark | 380/21 |
| 5,996,011 | A | 11/1999 | Humes | 709/225 |
| 6,044,375 | A * | 3/2000 | Shmueli et al. | 707/101 |
| 6,055,544 | A | 4/2000 | DeRose et al. | 707/104 |
| 6,073,165 | A | 6/2000 | Narasimhan et al. | 109/206 |
| 6,078,907 | A | 6/2000 | Lamm | 705/40 |
| 6,094,483 | A | 7/2000 | Fridrich et al. | 380/28 |
| 6,148,342 | A | 11/2000 | Ho | 709/225 |
| 6,154,172 | A | 11/2000 | Piccionelli et al. | 342/357.1 |
| 6,192,472 | B1 | 2/2001 | Garay et al. | 713/165 |
| 6,253,203 | B1 * | 6/2001 | O'Flaherty et al. | 707/9 |
| 6,301,668 | B1 | 10/2001 | Gleichauf | 713/201 |
| 6,370,629 | B1 | 4/2002 | Hastings et al. | 711/163 |
| 6,389,542 | B1 | 5/2002 | Flyntz | 713/201 |
| 6,487,538 | B1 | 11/2002 | Gupta | 705/24 |
| 6,598,161 | B1 * | 7/2003 | Kluttz et al. | 713/166 |
| 6,602,298 | B1 | 8/2003 | Kirshenbaum | 715/502.2 |
| 6,662,189 | B2 * | 12/2003 | Oyanagi et al. | 707/102 |
| 6,714,977 | B1 | 3/2004 | Fowler | 709/224 |
| 6,771,290 | B1 | 8/2004 | Hoyle | 345/745 |
| 2002/0073311 | A1 | 6/2002 | Brown et al. | 713/165 |
| 2002/0073313 | A1 | 6/2002 | Brown et al. | 713/165 |
| 2002/0116641 | A1 | 8/2002 | Mastrianni | 713/201 |
| 2004/0054630 | A1 | 3/2004 | Ginter | 705/53 |

FOREIGN PATENT DOCUMENTS

| | | |
|---|---|---|
| WO | WO 00/75779 | 12/2000 |
| WO | WO 00/75779 A2 | 12/2000 |
| WO | WO 00/75779 A2 | 12/2000 |

OTHER PUBLICATIONS

Element-Wise XML Encryption, Hiroshi Maruyama and Takeshi Imamura, IBM Research, Tokyo Research Laboratory (4 pages), Apr. 20, 2000.

Survival Information Storage Systems by Jay J. Wylie, Michael W. Bigrigg, John D. Strunk, Gregory R. Ganger, Han Kiliccote Pradeep K. Khosla (8 pages), Aug. 2000.

ZD Net Interactive iWeek—IBS, SAP: XML to Boost Security Integration ( 1 page), May 3, 1999.

Myers, A.C. "Mostly-Static Decentralized Information Flow Control" M.I.T. Doctoral Thesis Jan. 1999.

Cisco Systems' Intrusion Detection System (IDS) Host Sensor 2.0 product data sheet and technical overview, 10 pgs., Jul. 3, 2000, www.cisco.com.

"Protecting Privacy using the Decentralized Label Model" A. Myers, Cornell Univ. Jan. 1, 2000.

Mimesweeper Product Data sheet, Resoft Int'l LLC., Nov. 12, 2001 re-soft.com/product/mimeswep.

Complete Content Security for Internet Gateways and Mail Servers, Aladdin, Jul. 2000.

Aladdin Product announcement for e-Safe Appliance, Aladdin Knowledge Sys., Ltd., Nov. 8, 2001, Aks.com/news/2001/e-safe.

Mail Attender 4.1x product white paper by Sherpa Software, Oct. 2001.

MIMEsweeper-Content Security for E-mail, Web Browsing & Webmail, Nov. 12, 2001.

Cisco IDS Host Sensor Product, Oct. 16, 2001.

Ingrian i100, Content Security Appliance (1 pages), printed Jun. 24, 2001.

Element-Wise XML Encryption, Hiroshi Maruyama and Takeshi Imamura, IBM Research, Tokyo Research Laboratory (4 pages), Apr. 20, 2000.

Survival Information Storage Systems by Jay J. Wylie, Michael W. Brigrigg, John D. Strunk, Gregory R. Ganger, Han Kiloccote Pradeep K. Khosla (8 pages), Aug. 2000.

ZD Net Interactive Week—IBS—SAP: XML to Boost Security Integration (1 page), May 3, 1999.

Myers, A.C. "Mostly-Static Decentralized Information Flow Control" M.I.T. Doctoral Thesis Jan. 1999.

The 1996 book, Applied Cryptography, by Schneier.

The Uniform Resource Locator article "Fold OC", Feb. 17, 2000.

Microsoft Word "Learning Microsoft Word 7.0", Jul. 9, 1997.

Intelligence Community System for Information Sharing (ICSIS) Relationship to the Global Information Grid (GIG), White Paper, Mar. 27, 2001.

* cited by examiner

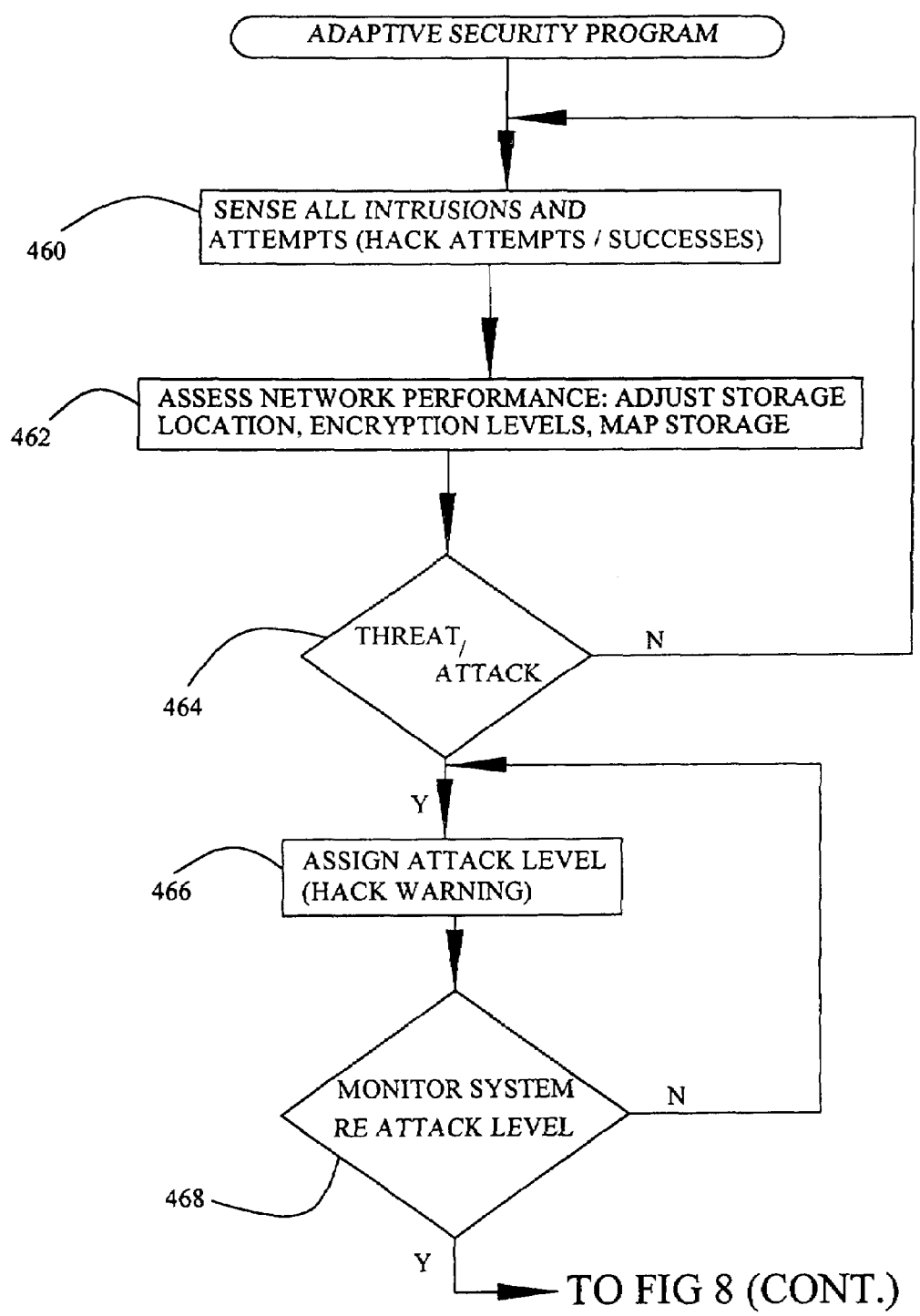

DATA SECURITY SYSTEM AND METHOD ASSOCIATED WITH DATA MINING

This is a continuation-in-part of patent application Ser. No. 10/155,192 filed on May 23, 2002 and 10/155,525 filed on May 23, 2002, now U.S. Pat. No. 7,191,252 and is a regular patent application claiming the benefit of provisional patent applications 60/400,062 filed on Aug. 2, 2002, 60/400,112 filed on Aug. 2, 2002, 60/400,406 filed on Aug. 2, 2002, and 60/400,407 filed on Aug. 2, 2002, and is a continuation-in-part of patent application Ser. No. 10/008,209 filed on Dec. 6, 2001 now U.S. Pat. No. 7,140,044 and 10/008,218 filed on Dec. 6, 2001, now U.S. Pat. No. 7,146,644 and is a continuation-in-part of patent application Ser. No. 09/916,397 filed Jul. 27, 2001 now U.S. Pat. No. 7,146,644 which is a regular patent application is based upon provisional patent application No. 60/260,398, filed Jan. 9, 2001; application Ser. No. 60/287,813, filed on May, 2, 2001; application Ser. No. 60/267,944, filed Feb. 12, 2001; application Ser. No. 60/247,242, filed Nov. 13, 2000 and application Ser. No. 60/247,232, filed Nov. 13, 2000.

The present invention relates to a data security system and method and, more specifically, to a process, program and system which is adjunct or additive to an email system, a browser program or a telecommunications program. The invention filters, extracts, disperses, via a controlled release of data segments to storage locations and permits reconstruction utilizing security protocols to provide a security system, for data. Scrubbing credit card data or financial data from text, a data object or data stream is also discussed herein.

BACKGROUND OF THE INVENTION

The extensive use of computers and the continued expansion of telecommunications networks, particularly the Internet, enable businesses, governments and individuals to create documents (whether text, characters, icons, images or a combination thereof, sound, video, and data objects in general, sometimes referred to generally herein as "data objects") and distribute those documents widely to others. Although the production, distribution and publication of documents is generally beneficial to society, there is a need to limit the distribution and publication of security sensitive words, characters or icons. Concerns regarding the privacy of certain data (for example, an individual's social security number, credit history, medical history, business trade secrets and financial data) is an important issue in society. In another words, individuals and businesses have a greater concern regarding maintaining the secrecy of certain information in view of the increasing ease of distribution of documents through computer networks and the Internet.

U.S. Pat. No. 6,055,544 to DeRose et al. discloses the generation of chunks of a long document for an electronic book system. DeRose '544 discloses solutions available to book publishers to publish books in electronic format on the worldwide web. One of the problems is that the books are published as small document fragments rather than publishing an entire book which, due to the formatting, protocol and command structure on the Internet, downloads an entire book to the user. The problem involved with publishing small documents is that there is no relationship to other portions of the book. See col. 3, lines 51-55 and col. 4, lines 3-5. One methodology to solve the problem involves inserting hypertext links in the book. This places a large burden on the book publisher. Col. 4, lines 19-21. Accordingly, it is an object of DeRose '544 to provide a mechanism for accessing only a portion of a large, electronically published document and automatically determining what portion of the document to download to the user based upon user selections that is, previous portions and subsequent portions of the document are downloaded with the selected portion, without maintaining separate data files for each portion of the document. Col. 4, lines 34-39. In other words, if a person wanted to access chapter 4 of a text, the system in DeRose '544 would display chapter 4, chapter 3 (the preceding chapter) and chapter 5 (the subsequent chapter). This publishing of portions of the document utilizes a subset of marked up elements established as being significant and a second subset of elements being less significant. For example, "Title elements" define a table of contents. A first representation of the document structure defined by all of the marked up elements may be used in combination with a second representation of the document structure defined only by the significant elements to control selection of portions of the documents such that previous and subsequent portions may be selected and rendered in a consistent and intuitive manner." Col. 4, lines 38-55. A computer system stores a first representation of the hierarchy of all elements in the electronic document. As example, this may be each chapter in its entirety. The computer also stores a second representation of the hierarchy of only significant elements in the electronic document. As an example, this may be a listing of each chapter without the text associated with the chapter. In response to request for a portion of the document, the computer system selects the portion defined by the significant element in the second representation. For example, if the user requested chapter 4, the entirety of chapter 4 would be downloaded from the web server to the client computer. In addition to rendering or publishing the selected chapter, the computer system looks to the relationship of the elements in the first representation of the hierarchy (the list of all chapters) and downloads from the web server the adjacent chapters. In this example, this would involve downloading chapters 3 and chapter 5. In a further embodiment, the computer system selects only a leaf element of the second representation as a significant element during the download. See the Summary of the Invention, col. 4, line 40 through col. 6, line 14.

U.S. Pat. No. 5,832,212 to Cragun et al. discloses a censoring browser method for viewing downloaded and downloading Internet documents. The abstract describes the system as including a user profile including user selected censoring parameters. Data packet contents are received from the Internet and the packets are compared with the user selected censoring parameters. Responsive to the comparison, the received data packet contents are processed and selectively displayed. The user selected censoring parameters include censored words and word fragments, and user selected categories. Compared word and word fragments can be removed and selectively replaced with predefined characters or acceptable substitute words. Tallies of weights for user selected categories are accumulated and compared with used selected threshold values. A predefined message can be displayed responsive to an accumulated tally exceeding a user selected threshold value without displaying the received data packet contents.

U.S. Pat. No. 6,094,483 to Fridrich discloses an encryption methodology hiding data and messages in images. In one application of the system in Fridrich '483, a method is disclosed of embedding a secret digital square image with 256 gray levels within an image carrier. The secret image is first encrypted using a chaotic Baker map. The resulting image is a random collection of pixels with randomly distributed gray levels without any spatial correlations. The carrier image is twice the size (height and width or 2n×2m) the secret image with 256 gray levels. The carrier image is modified according to a mathematical formula.

U.S. Pat. No. 5,485,474 to Rabin discloses a scheme for information dispersal and reconstruction. Information to be transmitted or stored is represented as N elements of a field or a computational structure. These N characters of information are grouped into a set of n pieces, each containing m characters. col. 1, lines 37-46. The system is used for fault tolerance storage in a partitioned or distributed memory system. Information is disbursed into n pieces so that any m pieces suffice for reconstruction. The pieces are stored in different parts of the memory storage medium. A fairly complex mathematical algorithm is utilized to provide reconstruction of the information utilizing no fewer than m pieces.

U.S. Pat. No. 6,192,472 B1 to Garay et al. discloses a method and apparatus for the secure distributed storage and retrieval of information. Garay '472 identifies the problem as how to store information in view of random hardware or telecommunications failures. Col. 1, lines 17-20. The initial solution is to replicate the stored data in multiple locations. Col. 1, lines 28-31. Another solution is to disperse the information utilizing in Information Dispersal Algorithm (IDA). The basic approach taking in IDA is to distribute the information F being stored among n active processors in such a way that the retrieval of F is possible even in the presence of up to t failed (inactive) processors. Col. 1, lines 40-44. Another issue is the utilization of cryptographic tools. With the use of tools called distributed fingerprints (hashes), the stored data is distributed using the fingerprints and coding functions to determine errors. In this way, the correct processors are able to reconstruct the fingerprint using the code's decoding function, check whether the pieces of the file F were correctly returned, and finally reconstruct F from the correct pieces using the IDA algorithm. Col. 2, lines 50-59. Garay '472 also discloses the use of Secure Storage and Retrieval of Information (SSRI) with the added requirement of confidentiality of information. Col. 3, line 56. With this added requirement, any collision of up to t processors (except ones including the rightful owner of the information) should not be able to learn anything about the information. Confidentiality of information is easily achieved by encryption. Col. 3, lines 56-61. The issue involves encryption key management, that is, the safe deposit of cryptographic keys. Garay '472 discloses confidentiality protocol utilizing distributed key management features. This mechanism allows the user to keep his or her decryption key shared among several n servers in such a way that when the user wants to decrypt a given encrypted text, the user would have to interact with a single server (the gateway) to obtain the matching plaintext while none of the servers (including the gateway) gets any information about the plaintext. Col. 4, lines 5-14.

U.S. Pat. No. 5,996,011 to Humes discloses a system and a method for filtering data received over the Internet by a client computer. The system restricts access to objectionable or target data received by a client computer over an Internet by a web server by filtering objectionable data from the data received. The Humes '011 system filters the data "on the fly." Further, the Humes '011 system can be applied to process any type of target data from the data received and displayed to the user. Col. 2, lines 32-44. If the web page requested by the user contains only a minimum amount of objectionable or target data, the user receives only a portion of the filtered web page for viewing. Hume '011 also provides that if the web page contains a large amount of objectionable material, the system blocks the entire display of the web page on the user's computer monitor. Col. 2, lines 56-62. Hume '011 provides three levels of filtering. At the first level, if the domain name contains objectionable words or material, the initial download from the domain is blocked. At the second level, the text in the download is filtered and objectionable words are replaced with a predetermined icon, for example, "- - - ". Col. 3, lines 32-35. The filter uses a dictionary. Col. 3, lines 45-48. The filtered out words are counted. If the final score of "filtered out" material exceeds a predetermined threshold, the entire page is blocked from the user's view. Col. 4, lines 2-4.

U.S. Pat. No. 5,905,980 to Masuichi, et al., discloses a document processing apparatus for processing various types of documents, a word extracting apparatus for extracting a word from a text item including plural words, a word extracting method used in the document processing apparatus, and a storage medium for storing a word extracting program. Extracted words are associated with other words via an algorithm. The extracted words and associated words are used as a search index for the document.

U.S. Pat. No. 5,996,011 to Humes discloses a computer based system and method for filtering data received by a computer system, and in particular, for filtering text data from World Wide Web pages received by a computer connected to the Internet, for purposes of restricting access to objectionable web sites.

U.S. Pat. No. 6,148,342 to Ho discloses a system for managing sensitive data. The system prevents a system administrator from accessing sensitive data by storing data and identifier information on different computer systems. Each query from a user's terminal is encrypted using two codes, the first code readable only by an identifier database and a second code readable only by a data access database. The data is routed from the user's source terminal to the identifier database at the first computer. The first computer/identifier database first verifies the user's ID and the security clearance for the requested information and substitutes a second internal ID to the data packet/query. The modified query is then presented to the data access database (the second computer) and, subject to a second security clearance, the response to the data query is sent back to the user's source terminal.

A publication entitled "Element-Wise XML Encryption" by H. Maruyama T. Imamura, published by IBM Research, Tokyo Research Laboratory, Apr. 20, 2000 discloses a protocol or process wherein certain parts of an XML document are encrypted and the balance of the plaintext is not encrypted. The protocol is useful in three party transactions, for example, when a buyer sends an order in an XML document to a merchant which contains the buyer's credit card information. The credit card information is sent to a credit company and the merchant does not need to know the credit number as long as he obtains clearance or authorization from the credit card company. Another instance is an access control policy which requires a certain part of an XML document to be readable only by a privileged user (for example, a manager could access the salary field in an employee records but others could only access name, phone and office fields). The Imamura article discusses encryption protocol, the delivery of keys and the utilization of compression. The article does not discuss separate storage of the critical data apart from the plaintext of the XML document.

The Ingrain i100 Content Security Appliance product brochure, available in June, 2001, discloses a system coupled to multiple web servers (computers) to accelerate secured transactions between multiple client computers (over the Internet) and prevents Secure Sockets Layer SSL performance bottlenecks by performing high-performance SSL handshakes and encrypting all data sent to back end servers using long-lived SSL session.

An article entitled "Survivable Information Storage Systems" by J. Wylie M. Bigrigg, J. Strunk, G. Ganger, H. Kiliccote, and P. Khosla, published August, 2000 in COMPUTER, pp. 61-67, discloses a PASIS architecture which combines decentralized storage system technologies, data redundancy and encoding and dynamic self-maintenance to create survivable information storage. The Bigrigg article states that to achieve survivability, storage systems must be decentralized and must spread information among independent storage nodes. The decentralized storage systems partition information among nodes using data distribution and redundancy schemes commonly associated with disc array system such as RAID (redundancy array of independent discs) insuring scalable performance for tolerance. P. 61. Thresholding schemes—also known as secret sharing schemes or information dispersal protocols—offer an alternative to these approaches which provide both information confidentiality and availability. These schemes and codes, replicate, and divide information to multiple pieces or shares that can be stored at different storage nodes. The system can only reconstruct the information when enough shares are available. P. 62. The PASIS architecture combines decentralized storage systems, data redundancy and encoding and dynamic self-maintenance to achieve survivable information storage. The PASIS system uses threshold schemes to spread information across a decentralized collection of storage nodes. Client-side agents communicate with the collection of storage node to read and write information, hiding decentralization from the client system. P. 62. The device maintains unscrubable audit logs—that is, they cannot be erased by client-side intruders—security personal can use the logs to partially identify the propagation of intruder-tainted information around the system. P. 63. The article states that, as with any distributed storage system, PASIS requires a mechanism that translates object names—for example file names—to storage locations. A directory service maps the names of information objects stored in a PASIS system to the names of the shares that comprised the information object. A share's name has two parts: the name of the storage node on which the share is located and the local name of the share on the storage node. A PASIS file system can embed the information needed for this translation in directory entries. P.63. To service a read request, the PASIS call client (a) looks up in the directory service the names of the n shares that comprise the object; (b) sends read requests to at least m of the n storage nodes; (c) collects the responses and continues to collect the responses until the client has collected m distinct shares; and (d) performs the appropriate threshold operation on the received shares to reconstruct the original information. P. 63. The p-in-n general threshold scheme breaks information into n shares so that (a) every shareholder has one of the n shares; (b) any m of the shareholders can reconstruct the information; and (c) a group of fewer than p shareholders gains no information. P. 64. Secret-sharing schemes are p-m-n threshold schemes that trade off information confidentiality and information availability: the higher the confidentiality guaranty, the more shares are required to reconstruct the original information object. Secret sharing schemes can be thought of as a combination of splitting and replication techniques. P. 64. The article discusses the technique of dissemination which divides information objects into n pieces and stores each piece separately. Dissemination decreases information availability because all shares must be available. It offers no information theoretic confidentiality because each share expresses 1/n of the original information. P. 64. Short secret sharing encrypts the original information with a random key, stores the encryption key using secret sharing, and stores the encrypted information using information disperse. P. 64. An extension to the threshold schemes is cheater detection. In a threshold scheme that provides cheater detection, shares are constructed in such a fashion that a client reconstructing the original information object can tell, with high probability, whether any shares have been modified. This technique allows strong information integrity guarantees. Cheater detection can also be implemented using cryptographic techniques such as adding digest to information before storing it. P. 65. For the highest architecture to be effective as possible, it must make the full flexibility of threshold schemes available to clients. The article believes this option requires automated selection of appropriate threshold schemes on a per object basis. This selection would combine object characteristics and observations about the current system environment. For example, a client would use short secret sharing protocol to store an object larger than a particular size and conventional secret sharing protocol to store smaller objects. The size that determines which threshold scheme to use could be a function of object type, current system performance, or both. P. 67.

The MAIL sweeper and MIME sweeper programs by ReSoft International uses a keyword search engine to review e-mails for certain words or phrases. IF the e-mail does not clear the filter, the addressee data must clear a data base check to protect the privacy and/or confidentiality of the e-mail data. See re-soft.com/product/mimesweep. The Aladdin eSafe Appliance restricts outgoing e-mails from sending classifier or prohibited content. See aks.com/news/2001/esafe.

OBJECTS OF THE INVENTION

It is an object of the present invention to provide a data security system, an information processing system and a method for securely storing data and rebuilding that data in the presence of an adequate security clearance.

It is another object of the present invention to provide a method for securing data on a single personal computer (PC), on a plurality of computers linked together through a local area network (LAN) or a wide area network (WAN) or the Internet.

It is a further object of the present invention to provide a method for securing data utilizing a client-server computer system. The client-server computer system may be implemented over the Internet. The security system may be provided to the public, to government or to private entities as an Application Service Provider or ASP over the Internet.

It is a further object of the present invention to provide a method for securing data which is highly flexible and programmable by a user.

It is an additional object of the present invention to enable the user to establish (a) the scope of the security sensitive words, characters or icon, data objects, (b) the future use (or destruction or encryption) of a filter enabling extraction of security sensitive data, (c) the selection of storage locations (local, removable, in an LAN, a WAN or on the Internet) for extracted data and remainder or common data and (d) one or multiple levels of security limiting full reconstruction and enabling partial reconstruction of the extracted data and the remainder or common data.

It is another object of the present invention to establish and manage the separation of user-based communities of interest based upon crypto-graphically separated, need to know security levels.

It is another object to provide an adaptive system responsive to hacking attempts and hacking attacks.

These steps may be completely automated (after some parameters are set or programmed by a system administrator), may be fully programmable by the user, or may be a combination of automated and manual controls implemented by the systems administrator and/or the user-client.

It is an object of the present invention to parse, disperse and reconstruct the data or data object thereby enabling secure storage of the data. For example, financial data maintained by an institute, can be parsed with an algorithm, the parsed segments dispersed off-site and away from the financial institute, and, upon appropriate security clearance, the dispersed data can be reconstructed to duplicate the data. Large distribution of parsed data is contemplated by this aspect of the invention. The original data remains stable, operable and immediately useful. The securing dispersed data is a back-up of the original data.

It is a further object of the present invention to secure e-mail data transmissions and web browser transmissions by extraction of security sensitive data, facilitating the remote storage of said data and sending remainder data to the e-mail addressee or the recipient.

It is another object of the present invention to use fine-grained selection of security critical data, extraction and encryption and separate storage of the secured data. The parsing or filtering of plaintext, data object, file or data stream thereby bridges the gap between full encryption of the plaintext etc. and no encryption. The present system is therefore a more efficient use of processing speeds, times, and storage resources.

It is a further object to create a credit card number or financial data scrubber. The scrubber may be employed to remove any security critical data.

It is another object of the present invention to permit the user to decide on and select a level of risk he or she believes appropriate by selecting no, minimal, intermediate or maximum levels of data security.

It is another object of the present invention to permit the user to access data security risks, access data processing resources (processing time, storage facilities, data access time, etc.) and select a security level which balances risks and resources.

SUMMARY OF THE INVENTION

The method for securing data in a computer system in one embodiment includes establishing a group of security sensitive words, characters, icons, data streams or data objects, filtering the data input from a data input device and extracting the security sensitive data. The extracted data is separated from the remainder data and is separately stored. In one embodiment on a personal computer (PC) system, the extracted data and the remainder or common data is stored in different, distributed memory segments. In a network implementation, the extracted data may be stored in one computer and the remainder or common data may be stored in another computer. In a client-server implementation, the server may direct storage of the extracted data to a different location than the remainder data, either on the server or on a further memory system (computer) interconnected to the server or on the client computer and in distributed memory segments. A map may be generated by a software module or sub-system indicating the location of the extracted data and the remainder data in the network. The filter may be destroyed (via a deletion routine) or may be retained for future use by the user. If retained, encryption is preferred. The map may be stored on the client computer or the user's PC or may be stored on the server. Copies of the map may be removed (deleted) from the user's PC or the client computer. The map may be encrypted. The extracted data and/or the remainder data may be removed (deleted or scrubbed) from the originating computer. Encryption can be utilized to further enhance the security levels of the system. All transfers of the filter between the client to the server may be encrypted, and all data (whether extracted data or remainder data) may be encrypted prior to storage in the distributed memory. Any transfer of extracted data or remainder data or maps or filters may include an encryption feature. Reconstruction of the data is permitted only in the presence of a predetermined security clearance. A plurality of security clearances might be required which would enable a corresponding plurality of reconstructing users to view all or portions of the data. Persons with low level security clearance would only be permitted to have access to low level extracted data (low level security sensitive data) and the common data. Persons with high level security clearances would be permitted access to the entire document reconstituted from the extracted data and the remainder data. A computer readable medium containing programming instructions carrying out the methodology for securing data is also described herein. An information processing system for securing data is also described.

In another embodiment, the method for securing data in a computer network and transparently establishing and managing the separation of user-based communities of interest based upon cryptographically separated, need to know, security levels, by necessity, utilizes communities of interest representing a plurality of users having corresponding similar security levels, each with a respective security clearance. In other words, all members of Community A have the same security level and security clearance, which is different than the users of Community B which have a different security level and security clearance. The method and the computer media containing programming instructions includes filtering data from the data input computer, extracting security sensitive words, phrases, characters, icons, or data objects and forming subsets of extracted data and remainder data. The subsets of extracted data are stored in one or more computer memories in the network identified as extracted stores. The remainder data is also stored in the network if necessary. Reconstruction of some or all of the data via one or more of the subsets of extracted data and the remainder data is permitted only in the presence of a predetermined security clearance from the plurality of security levels. The cryptographically separated, need to know, security levels correspond to respective ones of the plurality of security levels and the method includes, in one embodiment, encrypting subsets of extracted data with corresponding degrees of encryption associated with the plurality of security levels. During reconstruction, all or a portion of the plaintext data is decrypted only in the presence of the respective security level. The information processing system which secures data per the community of interest security level in the includes a data filter for the data input from the data input computer which extracts the security sensitive words, phrases, icons or data objects. A system and a methodology for storing the subsets of extracted data and remainder data is provided and a compiler permits reconstruction of some or all of the plain text data in the presence of an appropriate security clearance level. Multiple level encryption in one document is also available.

An adaptive method of securing data responsive to a plurality of hacking events utilizes a hacking monitor which generates a corresponding plurality of hack warnings dependent upon the severity of the hacking attack. Based upon respective ones of the hacking or hack warnings, data is filtered to extract security sensitive words, phrases etc. and the extracted data and the remainder data (if necessary) is stored based on the degree of hack warning. Reconstruction is permitted of some or all the data utilizing the extracted data and the remainder data only in the presence of the predetermined security clearance level. Automatic reconstruction is permitted after the hack attack terminates. The method sometimes includes encrypting extracted data dependent upon the degree or severity of the hack warning and decrypting that data during reconstruction. A computer readable medium containing programming instructions similar to the method is also provided. The information processing system includes a filter which is adjusted based upon the degree of hack warning to extract security sensitive words. A storage system stores extracted data and remainder data (if necessary) based upon the level of the hack warning and a compiler is used to reconstruct the data in the presence of the appropriate security clearance level.

The parsing and dispersion aspects of the present invention enable the user to parse, disperse and reconstruct the data or data object thereby enabling secure storage of the data. The original data may be maintained in its original state and stored as is customary, encrypted or destroyed. For example, financial data maintained by an institute in its original state, and a copy thereof can be parsed with an algorithm, the parsed segments dispersed off-site, (that is, separated and stored in extract and remainder stores or computer memories), away from the financial institute, and, upon appropriate security clearance, the dispersed data can be reconstructed to duplicate the data. Large distribution of parsed data is contemplated by this aspect of the invention. The original data remains stable, operable and immediately useful in its stored location. The secured and dispersed data is a back-up of the original data. Destruction of the original source is also an alternative embodiment.

Another embodiment of the present invention operates in an e-mail or a web browser environment. In a specific embodiment, the invention operates as a credit card or financial data scrubber. The e-mail data has one or more security sensitive words, characters or icons and the method or computer program works in a distributed computer system with a remote memory designated as an extract store. The method extracts the security sensitive words, characters or icons from said e-mail data to obtain extracted data and remainder data therefrom. The extracted data is stored in the extract store. The methodology emails the remainder data to the addressee. the addresses is permitted to retrieve the extracted data from said extract store only in the presence of a predetermined security clearance and hence, reconstruct the e-mail data with said extracted data and remainder data. The program and method on the user's e-mail device extracts the security sensitive data, facilitates storage of the extracted data in said extract store and, emails the remainder data to the addressee. Rather than extracting security data, the method and program may parse the data. The method and program for safeguarding data entered via a browser involves extracting security sensitive data, facilitating the storage of such data in the remote store, and forwarding the remainder data to a targeted destination in the distributed computer system. The scrubber may utilize a pop-up window to enable user activation of the scrubber on an email or a web browser communication.

The present invention can be configured in various forms. The following descriptions discuss various aspects of the invention and further advantages thereof.

The present invention enables the user to obtain automatic classification and declassification of documents on the fly. The extraction process downgrades and declassifies documents on the fly (in real time) so that they are useless to unauthorized parties. Presentation by a user of a valid security clearance enables substantially instant and seamless reconstitution of the security sensitive content.

The present invention can be configured to automatically secure unstructured documents and freeform documents, for example, e-mail, instant messaging, or Word documents (input documents).

The present invention may also be configured to automatically secure structured documents and transactional documents for example, database records or XML documents (input documents).

The present invention introduces flexibility into security management, risk management of data, data storage, and data flows and enable automatic responsiveness to threats. The innovation enables automatic response to security challenges and threats. The innovation can maintain, upgrade and downgrade the levels of security through implementation of a leveled granular extraction process and a controlled-release mechanism. Attacks or other external events can trigger a response in the form of higher extraction levels, expanding the type of content extracted, and constricting the release of important and critical data control from storage. How much and what to extract depends on the level of threat or perceived risk. In same manner, the amount and type of content released from storage and reconstituted depends on the level of threat or risk perceived by the system. The system delivers a level of security protection specifically matched to meet security needs as dictated by the changing security threats, environment, policy and organizational needs.

The present invention enables a user to introduce and maintain multiple levels and standards of security. It is common knowledge that the highest security is delivered through total separation. Whereas this concept has only been implemented physically or by isolating computer environments, the invention achieves this concept of total separation within open and networked computer environments. The invention can implement a total physical and logical separation of important and critical data from its context and can preclude access to that information without a needed granular access permission. The invention is also effective for sounds and images (data objects or data streams with security words, characters, terms, icons or other data objects).

Some aspects of the present invention introduce a new method and apparatus to monitor security sensitive content through a process of analysis and categorization of each word or character, in a document. The invention enables processing of every character, word, number, as they are entered into a document and categorizes each into one of many pre-set categories. Categories can include surnames, locations, currency, defined terminology, and unknown words or phrases.

The present invention, in some embodiments, introduces a method and apparatus for plain text extraction and dispersion of security sensitive data. Maximum security with traditional methods encumbers free flow of information and business efficiency. Encryption burdens computer systems with high performance overhead, and its use is limited to the parties who have decryption capabilities. The invention offers a new solution. It enables leveled security in plain-text format, in addition to none, some, or all of pre-existing encryption, decryption, firewalls, and other security infrastructure. The level of security is determined by the extent of the security sensitive items, selection process; the extent of dispersal to various distributed storage locations; the rules for controlled-release from storage; and the access rules governing the reconstitution of extracts into the secured document.

In this configuration of the invention, the extractions are dispersed to distributed storage on a granular level. The rest of the document can be stored at its original location and/or other storage locations. Dispersal of extractions introduces new barriers not existing in current security. In certain situations, an attacker has first to find the (encrypted) map to the locations, then locate and access the distributed storage, get the data released from the controlled-release storage, and finally reintegrate the extracts into the appropriate documents.

Further, the present invention enables the user to implement a method and apparatus for targeted extraction and encryption of security sensitive items. The extraction capabilities of the system enable different workflow modes. The system enables extraction and encryption of important and critical content. In essence, only the critical content is extracted and/or encrypted, whereas the rest of the document remains as plaintext. This capability enables the following: advantages and flexibility; and the ability to share the document within the organization or transmit it to outsiders while still maintaining security over the most important and critical content of the document. This is an automatic process for controlling the content of outgoing e-mail. The document owner releases the important and critical content by enabling access to it to defined parties at defined times within defined threat modes.

The present invention, in some implementations, introduces a method and apparatus for encrypting document or extractions with multiple encryption types. The invention can deliver the highest level of security by using multiple types of encryption (and/or multiple keys) for one line, paragraph or document. Maximum security is delivered through automatic selection of security sensitive items, and encrypting these extractions with one or more types of encryption. The remainder data can also be encrypted. Multiple encryption types within one document statistically precludes deciphering that document regardless of the available computer power. Common encryption methods are vulnerable through existing technologies, social engineering methods, carelessness, and workflow habits. Furthermore, simple encryption becomes more vulnerable (including triple DES) assuming future mathematical breakthroughs or quantum computing. Existing methods to crack block ciphers are being improved to compromise the future AES Rinjdael standard.

The present invention also enables the user to configure the system to introduce a method and apparatus for content dispersion. The innovation enables control over specific important and critical content items within the general contents of documents or digital files in a computer or within a network. The immediate controlled-release of those important content items according to specific identification and access criteria proactively safeguards the security and the value of documents or digital files. The content control enables broad dissemination of the digital files in closed networks, as well as open networks including the Internet, without compromising the security of the important and critical information in the digital file. The dispersal channels can include any of all of the following: networks, Internet, Virtual Private Channel. Telephone lines, Optical lines, Wireless, Fax, Documents, Verbal communication.

The present invention, when configured in an appropriate manner, introduces a method and apparatus for enhancing the survivability capabilities of an organization and its networks. If networks get damaged, the decryption capability, such as PKI, is likely to be compromised, or at a minimum, suspended. In such instances, the invention enables continuation of work on channels, which need not be secure. In addition, the dispersion of information guarantees maximum partial reconstitution to documents and transactions, or total reconstitution to documents and transactions benefiting from backup at distributed storage facilities.

The present invention, in the appropriate environment, introduces a method and apparatus for delivering security for inter-connecting networks. It enables security for closed networks connecting to the Internet and other open networks. The Internet infrastructure and open networks are not secure. Even secured closed networks, such as VPNs, are not secured enough. The critical content of documents is the critical asset of the organization and must be highly secured, with maximum reliability, full transparency and instant accessibility. To remain competitive, organizations must maximize utility of the critical data within their documents, files, databases and servers. The securing of such documents must not be at the expense of compromising the access or processing speed of such documents. The invention enables work in plain text, as well as with encryption. Working in plain text reduces the computing performance overload.

Some aspects of the present invention introduce a method and apparatus for delivering information flow control in decentralized environments. Protection of privacy and confidentiality of information represents a long-standing challenge, The challenge has become much bigger with the expansion of the Internet, which has created decentralized networks. Parties, who do not know or trust each other, have to exchange information. The invention enables free flow and sharing of information between parties by removing burdening security restrictions and creating top security with a controlled-release of the security sensitive content in the documents. The technology enables top security through introduction of user and organization's ownership and control of the critical granular data in documents.

The system, in certain embodiments, introduces an additional layer of access controls at the granular level of the user document. In order to view the reconstructed critical information the user would need to be verified by additional access controls at the data storage level. The user access code or a physical key enables release of data from the storage. Today's access controls do not stop the user from distributing documents to other parties. The inventions fined grained controlled-release mechanism releases the critical information, only under a required set of circumstances and access validation. The invention enables the user ownership of his security sensitive critical data and conditions for its release and dissemination. The user has the option to hide the critical data through declassification process and release through a reclassification process in which the critical data would be reconstituted in the document.

The present invention, when configured by the user, introduces a method and apparatus for delivering compartmentalization of security sensitive content by leveled access to users. The invention creates leveled sharing of information, for example such that persons with level 3 access will have keys for encryption type RSA persons with level access 2 will have access to Blowfish encryption within one document.

The present invention, in certain embodiments, introduces a method and apparatus for enabling more use of distributed and dispersed storage including ASPs (application service providers). There is a major human tendency to refrain from sending important documents to web storage locations because of potential security breaches. This cultural issue is both driven by psychological issues and well-founded security concerns. The retention of those documents as is in physical proximity or locked security, provides actual security but precludes gaining any utility from those documents in a functional business setting. Instead the invention enables functional distribution of those documents without the security sensitive data, and a controlled-release of some or all of the extractions in a granular way in order to support business activities while retaining security.

The present invention, in certain configurations, introduces a method and apparatus for enabling lower storage costs. The extraction process declassifies and downgrades mission critical documents. The downgrading and transformation of a critical document into a non-critical document, enables storage in less secured and lower cost storage. Taking advantage of this security-initiated, extraction process can yield substantial storage cost savings. The invention enables a high return on investment ROI for system storage cost arbitrage. Splitting the data into critical and non-critical enables 20 to 90% savings on storage cost.

The present invention, in certain circumstances, delivers an automated security risk management system that creates added in-depth security defenses at the semantic-level as well as creation of controlled-release mechanisms at the storage-level with significantly reduced performance overhead requirements.

Certain embodiments of the present invention present a technology which answers the security demands as required by Committee on Information Systems Trustworthiness of the National Research Council. The Committee's report, Trust in Cyberspace (1999), defines the security paradigms needed for a safe future. The report states: The substantial commercial off-the-shelf (COTS) makeup of a network information systems, the use of extensible components, the expectation of growth by accretion, and the likely absence of centralized control, trust, or authority demand a new approach to security: risk mitigation rather than risk avoidance; technologies to hinder attacks, rather than prevent them outright; add-on technologies and defense in depth; relocation of vulnerabilities rather than their elimination; none of the existing or security technologies addresses these needs in whole. The invention breakthroughs this barrier by providing a single system which implements each one of those four elements in a unified way. The invention controls information flow in centralized and decentralized environments, through controlled-release of information within distributed systems.

The present invention can be implemented to enable certain security measures while accommodating the performance needs of a network. The invention provides a method and apparatus to ease overhead performance on congested computer networks. It can adjust the security defenses based on the performance needs of the network. Many security systems overburden the already burdened computing environment in terms of computational overhead, labor, and training requirements. The invention enables to ease the overhead performance of a network by transforming from high overhead performance, encryption methods, and other security methods, to the method presented by this invention.

Certain aspects of the present invention minimize the time of exposure of the important content within a document. The invention enables to separate the important content from the rest of the document for substantial periods of time, thereby minimizing substantially the exposure to risk. It is possible for example to extract the important content from the document and release it for reconstitution only when the user will open the document. In such situations the important content could for example be time and unexposed for over 99% of the time and exposed for less than 1% of the time, which lowers the risk substantially.

Further, embodiments of the present invention provide a security risk management method and system to minimize security risks. The invention enables minimization of security risks by: Automatic separation and extraction of granular critical data from the core document. Dispersal of the extracted critical data groups to different secured storage locations. Reconstitution of the critical data in document for limited time, to minimize exposure to risk. Partial reconstitution, of the critical data, in core document, through a controlled release of granular critical data. Granular controlled release of data to specific authorized people only.

The present invention, in certain configurations, provides a controlled release security mechanism to enable the release of content and granular content from storage locations in a centralized and decentralized environment. The controlled release mechanism enables release of the appropriate content to the authorized party at the right time under the right circumstances.

The present invention sometimes provides a security solution against damage by insiders. Studies show that insiders cause 70%-85% of the damage. These nine innovations are described in detail as follows: The invention enables insiders and employees to work with documents while managers and owners control the release of the critical prioritized information. The control is granular, thereby enabling continued work with the rest of the content in the document. The objective is to empower the user with the highest security while enabling him maximum sharing and delivery flexibility. This enables free flow of information between closed networks and public networks, such as the Internet, without compromising the security through extraction of important and critical content. The user can transport documents through various networks and e-mail services knowing that the critical information, which is still under control, and is not compromised.

The present invention can be configured to provide an automatic security system in order to overcome human flaws that create security vulnerabilities. Human engineering flaws are the cause of 90% of security vulnerabilities. For example, passwords are exposed through human fault enabling reading of plain text before it is encrypted. The invention enables an automatic process of appropriate response to security threats in an objective way and on an on going basis.

Certain aspects of the present invention provide an automatic security system in order to reduce human labor, and training costs.

The present invention provides, in one or more embodiments, protection for important granular content within a document. A feature left out in computer development is the protection and automatic protection of granular important content in a document. In every facet of life critical assets are immediately protected. For example, credit cards and cash are protected in a wallet, important items at home are placed in closets, wall units, cabinets and safes. The present system extracts the digital equivalent of these items, e.g., extracts all credit card data, and stores the extracted data in secure location(s).

In general, the present invention provides an alternative method to encryption. Mathematical security and encryption could be broken. Discovery of a mathematical equation for a shortcut of the factoring of prime numbers would be make mathematical security and encryption extremely vulnerable.

In 1999 a 512-bit RSA key was broken—at that time 95% of keys in e-commerce were 512 bits long. U.S. government 56-bit Data Encryption Standard was cracked in just 22 hours by the Freedom Foundation. 100,000 PCs were connected with a supercomputer which enabled the testing of 245 billion keys per second.

The invention, in a larger sense, provides an automated security risk management system. The system automatically responds to attacks by matching the defenses level to the level of threats The system responds to security threats through the following mechanisms: (1) controlled extraction of sensitive security data: in normal circumstances, extractions will take place according to pre-set rules; in threat situations, additional extractions will take place to deliver higher security; in an attack, additional substantial amounts of critical data will be extracted to deliver the highest security; (2) controlled dispersal to storage locations; in normal circumstances, dispersal to different storage locations according to pre-set rules will take place; in threat and attack situations, more dispersal to more storage locations, via additional communication channels will take place; and (3) controlled release of extracts for reconstitution; controlling amount of extracts released for reconstitution; controlling time of exposure of extracts in reconstitution; limiting access to specific people; and limiting access to specific times.

The present invention defends against devices like keyboard sniffers and mouse sniffers that can read information keyed into the computer and transmit it to an adversary. The invention enables to input security sensitive items through data input devices other than the keyboard. For example credit card numbers can be inputted through a hand held wireless device. The inputted data would be transferred to storage for possible reconstitution.

The present invention can also be configured to defend against devices that intercept electromagnetic signals from computers, monitors, printers, and keyboards. For example the Van Eck receptors which can read information off the screen the display screen. The invention enables separation contents of document into two or more displays thereby limiting the potential damage of electromagnetic eavesdropping.

The present invention, in many embodiments, enables the controlled release of data object full or partial release of plaintext source documents to persons or organizations with the appropriate security clearances.

Another object of the present invention is to enable the control of information flow over a PC, a network, a LAN, a WAN and over the Internet.

A further object of the present invention is to enable the interoperability of several secured networks based upon the relative security clearances of each network.

It is another object of the present invention to provide a process for synthesizing a document.

BRIEF DESCRIPTION OF THE DRAWINGS

Further objects and advantages of the present invention can be found in the detailed description of the preferred embodiments when taken in conjunction with the accompanying drawings in which:

FIG. 3A diagrammatically illustrates interleaving distinct data into different memory locations in a video memory.

DETAILED DESCRIPTION OF THE PREFERRED EMBODIMENTS

Figure 1A:
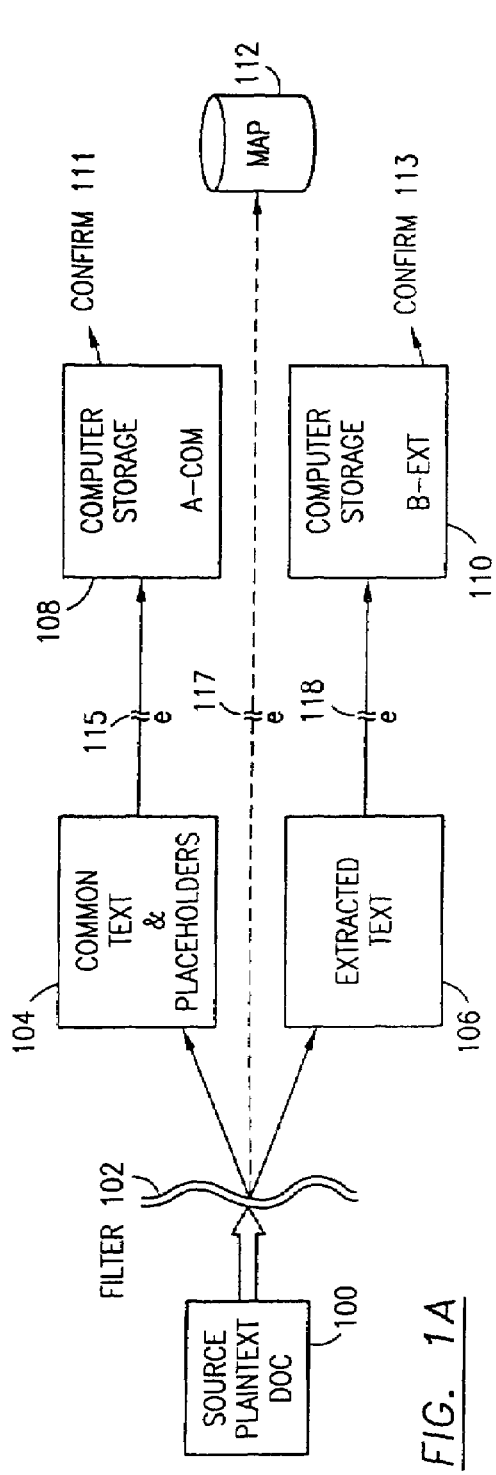
FIG. 1A diagrammatically illustrates a basic system diagram showing filtering and storing extracted data and remainder or common data and, in an enhanced embodiment, generating and storing a map.

The present invention relates to a data security system, a methodology of securing data on a personal computer (PC) system, on a computer network (LAN or WAN) and over the Internet and computer programs and computer modules and an information processing system to accomplish this security system.

It is important to know that the embodiments illustrated herein and described herein below are only examples of the many advantageous uses of the innovative teachings set forth herein. In general, statements made in the specification of the present application do not necessarily limit any of the various claimed inventions. Moreover, some statements may apply to some inventive features but not to others. In general, unless otherwise indicated, singular elements may be in the plural and vice versa with no loss of generality. In the drawings, like numerals refer to like parts or features throughout the several views.

The present invention could be produced in hardware or software, or in a combination of hardware and software, and these implementations would be known to one of ordinary skill in the art. The system, or method, according to the inventive principles as disclosed in connection with the preferred embodiment, may be produced in a single computer system having separate elements or means for performing the individual functions or steps described or claimed or one or more elements or means combining the performance of any of the functions or steps disclosed or claimed, or may be arranged in a distributed computer system, interconnected by any suitable means as would be known by one of ordinary skill in the art.

According to the inventive principles as disclosed in connection with the preferred embodiment, the invention and the inventive principles are not limited to any particular kind of computer system but may be used with any general purpose computer, as would be known to one of ordinary skill in the art, arranged to perform the functions described and the method steps described. The operations of such a computer, as described above, may be according to a computer program contained on a medium for use in the operation or control of the computer as would be known to one of ordinary skill in the art. The computer medium which may be used to hold or contain the computer program product, may be a fixture of the computer such as an embedded memory or may be on a transportable medium such as a disk, as would be known to one of ordinary skill in the art.

The invention is not limited to any particular computer program or logic or language, or instruction but may be practiced with any such suitable program, logic or language, or instructions as would be known to one of ordinary skill in the art. Without limiting the principles of the disclosed invention any such computing system can include, inter alia, at least a computer readable medium allowing a computer to read data, instructions, messages or message packets, and other computer readable information from the computer readable medium. The computer readable medium may include non-volatile memory, such as ROM, flash memory, floppy disk, disk drive memory, CD-ROM, and other permanent storage. Additionally, a computer readable medium may include, for example, volatile storage such as RAM, buffers, cache memory, and network circuits.

Furthermore, the computer readable medium may include computer readable information in a transitory state medium such as a network link and/or a network interface, including a wired network or a wireless network, that allow a computer to read such computer readable information.

In the drawings, and sometimes in the specification, reference is made to certain abbreviations. The following Abbreviations Table provides a correspondence between the abbreviations and the item or feature.

| Abbreviations Table | |
|---|---|
| A-com | computer or memory store for common or remainder data |
| ASP | application service provider - server on a network |
| B-ext | computer or memory store for extracted data |
| bd | board |
| CD-RW | compact disk drive with read/write feature for CD disk |
| comm. | communications, typically telecommunications |
| CPU | central processing unit |
| doc | document |
| dr | drive, e.g., computer hard drive |
| DS | data storage |
| e | encryption |
| ext-data | extracted data |
| I/O | input/output |
| I-com | Internet storage for common or remainder data |
| I-ext | Internet storage for extracted data |
| loc | location |
| mem | memory |
| MLS | multilevel security |
| obj | object, for example, a data object |
| pgm | program |
| re | regarding or relating to |
| recon | reconstruct |
| rel | release |
| req | request |
| rev | review |
| sec | security |
| SL | security level (sometimes S1 for security level 1, etc.) |
| sys | system |
| t | time |
| tele-com | telecommunications system or network |
| URL | Uniform Resource Locator, x pointer, or other network locator |

Basic Operational Theory

FIG. 1A diagrammatically illustrates the basic processes for establishing a secure storage of information, generally identified herein as "data." "Data," as used herein, includes any data object, e.g., text, images, icons, etc. Sound bites, data objects and video images may also be extracted as "data." A source document 100, sometimes referred to as a "plaintext," is passed through a filter 102. Filter 102, in a most basic sense, separates out common text or remainder data 104 from uncommon text, words, characters or icons. The security sensitive words, characters or icons are separated from remainder or common text 104 as extracted text 106. It should be noted that although the word "text" is utilized with respect to remainder text 104 and extracted text 106, the "text" is a data object and includes words, phrases, paragraphs, single characters, portions of words, characters, whole or partial images, or icons or sound or video. In a basic implementation, filter 102 may utilize a dictionary such that words present in the dictionary (common words) are separated from the source plaintext document 100 and placed into remainder document or common data file 104. The uncommon words (extracted-security sensitive words), not found in the dictionary, would be placed in an extracted text or extracted data file 106. For example, a business may wish to impose a security system on a contract document such that the names of the contracting parties (not found in the dictionary) and the street names (not found in the dictionary) would be stored in extracted data text file 106. The common text or remainder data would be stored in remainder data file 104. In the illustrated embodiment, remainder data file 104 also includes place holders which enables the extracted data to be easily inserted or set back into the remainder data file.

Input or Initial Processing Considerations

The security sensitive words, characters, icons or data objects may be any word, phrase, letter, character, icon, data object (full or partial), image or whatever, as pre-defined or as established by the user. The user may specifically design the filter, begin with a dictionary to define common terms, identify any additional security sensitive words, letters, images, icon, data objects, partial versions of the foregoing or any other granular aspect of the plaintext. After defining the filter and accepting the data input, the system filters the plaintext and separates extracted data (security sensitive items) from the remainder data. The filter may also include elements of artificial intelligence (AI). For example, the user may select one word as a security word and the AI filter may automatically select all synonymous words. The AI filter may enable the user to define a filter is real time at the entry of data via a keyboard. For example, the user may select to secure (i.e., extract and store) some proper names and may instruct the filter to secure names such as Block, Smythe and Cherry. During input of the plaintext, the system may detect Smith and ask the user if he or she wants to secure (a) all proper names in a common name dictionary collection and/or (b) all names with spellings similar to the filter input data, Block, Smythe and Cherry. As is known in the art, AI typically uses inference engines to define one pathway or to outline a course of action. The filter or extraction engine discussed herein can be configured with AI, inference engines, neural network systems or other automatic systems to carry out the functionality described herein for the dynamic operation of the security system.

The system and methodology described herein also encompasses parsing the plain text document by bit count, word, word count, page count, line count, paragraph count and parsing based upon any identifiable document characteristic, capital letters, italics, underline, etc. Algorithms may be implemented to parse the plain text document. The target of the parsing algorithm (a bit count, word, letter, etc.) is equivalent to the "security word, character or icon, data object" discussed herein. The parsing occurs with the filtering of the plain text source document 100 and the subsequent storage of extracted data apart from remainder data.

Storage

In a basic configuration, the common text or the remainder data is stored in common storage memory 108. This common or remainder data store is identified as A-com generally referring to a segmented memory in a PC or a computer A in a network (LAN or WAN). It should be understood that reference to "remainder data" is simply a short-hand representation of data that is not extracted or filtered by the system. Accordingly, "remainder data" is simply that data which can be viewed, manipulated or further processed by the user inputting or initially processing the data. Remainder data storage 108 may include a confirm storage signal function 111 to send back a confirm storage signal to the data input device generating source plaintext document 100. The extracted data file 106 is stored in a different memory computer storage 110 (B-ext). In a preferred embodiment, memory segment 108 (A-com) is at a different location than computer storage memory segment 110 (B-ext). In a PC embodiment, memory A-com is a different memory segment than memory B-ext. In a networked embodiment, computer storage 108 may be on a different computer as compared with computer storage 110. In an Internet embodiment, common text or cleansed text storage is at one web site (which may be one computer) and the extracted, high security data is stored at another web site, buried web page or other Internet-accessible memory store location. In any event, the remainder text is stored in a memory A-com and the extracted data or high security words, characters, icons or data objects are stored in memory B-ext. After storage of the extracted data in memory 110, a confirmation indicator 113 may be generated to the client computer or the computer handling source plaintext input document 100 (the originating computer system).

As a simple example, the program configured in accordance with the present invention, could automatically detect entry of all credit card numbers types into a user's computer. The filter is set to detect the unique credit card sequence and data string. Assuming that the user's computer is operating a browser and the user is communicating with a server on the Internet, the user's computer would filter out the credit card number and send the number to a secure storage site. The secure storage site is owned, operated or leased by a trusted party. The extracted data, i.e., the credit card data, is stored at the trusted site. The URL or other identifying data is sent to the vendor from which the user wants to purchase goods and services over the Internet. When the vendor seeks to complete the transaction, the vendor sends a request code to the secure site, the trusted party at the secure extracted data storage site debits the user's credit card account (or otherwise debits the user's bank account) and sends an approval code to the vendor. In this manner, the vendor is never given the user's credit card—the card number is sent to a trusted party automatically by the filter in the security program described herein. The security program may be incorporated in a browser to automatically protect credit card data, personal data (as a method to become anonymous on the Internet), etc. from being deliberately broadcast to others on the Internet or to block others from snooping into the user's personal data while the user communicates over the Internet.

In a further enhancement of the present invention, the computer or data input device handling source plaintext document 100 may also record the location of A-com 108 and B-ext 110. The location data is called herein a "map." A memory mapping function is utilized. The map may be stored in a third memory location 112. Memory location map 112 may be a segment of the memory of the data input computer originating plaintext 100. The map may be encrypted for security reasons.

Extraction and Storage Enhancements

As a further enhancement of the present invention, the user, prior to initiating the security system, may be given a choice of filtering out all the uncommon words or words not found in the dictionary and adding certain security sensitive words, characters, icons or data objects to filter 102. The added words or terms are filtered out with the uncommon words. Of course, the user may be required to manually input all security words or download the security word filter from the Internet or another system on the LAN. For security systems having multiple security levels, a plurality of filters would be created, each filter associated with a different security level. Further, multiple security levels would require, in addition to remainder text document or data 104, a plurality of extracted data documents 106. The common or remainder text document or data 104 would still be stored in remainder computer storage A-com 108. However, each extracted data document 106 would be stored in a respective, separate computer memory segment or computer B-ext 110.

Separate storage of a plurality of extracted data at multiple, separate locations in B-ext is one of the many important features of the present invention.

In view of increasing levels of security relating to (a) the storage location A-com; (b) the transfer of remainder text document 104 to memory computer storage A-com 108; (c) the storage of map 112 (possibly encrypted); (d) the creation, storage or transfer of filter 102 (possibly encrypted); (e) the storage of extracted data at memory storage B-ext (whether singular or plural storage sites); and (f) the transfer of extracted data thereto, the system may include an encryption e feature. The encryption e function 115, 117 and 118 is diagrammatically illustrated in FIG. 1A.

The program of the present invention can be set to extract critical data (a) when the plaintext or the source document (data object) is created; (b) when the source document or data object is saved; (c) on a periodic basis; (d) automatically; (e) per user command; (f) per ascertainable or programmable event; and (g) a combination of the foregoing. Timing for storage of the extracted data is based on these aspects. Reconstruction of the data object or plaintext may be (a) automatic and substantially transparent to the user; (b) based upon manual entry of security clearance data; (c) periodic; or (d) a combination of the foregoing dependent upon outside events and who is the author of the data object or other definable aspects of the data object, its environment of origination, current and anticipated security threats and its environment of proposed reconstruction. The timing for the extraction, storage and reconstruction is oftentimes dependent upon the level of security required by the user and/or his or her organization.

The system and method creates a high level of security by automatic selection and removal of critical and prioritized contents from a data objects stream, whether it be a digital document, digital file, database, sound bite, video clip, other structured, or streaming data formats. The system and method enables a controlled release of the extracted data objects, enabling instant display of the instantaneous returned contents, contingent on verification of user identity, access rights, time of operation, location of source and or user, destination of source and or user, and determine threat modes. The system and method delivers high security by removal of the selected prioritized content from memories. The copies and traces of the selected extracted contents are eradicated from the computer memory while the separated extract data stream is transferred to a safe removed storage memory media. The extract, extracts, and any part thereof, will be return transferred to user display as soon as identity and access rights are validated.

A replacement of the extract (sometimes called a placeholder) can also be substituted on-the-fly to provide updated results, misinformation, dis-information, messages, alerts, links (to reports, data mining, search engines, web sites, and hyperlinks understood in the current art), advertisements, and personalization and customization. The validation can be done instantly by password, challenge questions and answers, remote verification (phone, video, or personal contact with user), or by biometrics means.

The extraction of data objects within data streams includes words, structured data objects, characters, numbers, bullet points, footnotes, prices, images, sound segments, video segments, and selected digital data packets. The extraction is conducted by separating a source (original) data stream into two or more extracts data streams. The different data object extractions are separated into groups reflecting predefined contextual categories and restitution applications (such as to enable customization and personalization for the same or different users). The modified source (original) stream typically contains the majority of data objects of the source stream, whereas the extract streams contains a minority of the data objects which represent selected and categorized information and information deemed to be of prioritized importance.

The extracted categorized data objects are separated into one or more contiguous data streams. The extracted data stream or streams are scattered to one or more storage memory memories. The extracted data can be transported and shuttled between different storage or projection apparatus, as directed automatically by various constraints including: security risk criteria of threats and attacks, sources, targets, users, policies, time of day, and threat modes.

The extracted data, in some cases, is transported to an online removable storage and under extreme security threats to an off-line/off-network, digital or physical vaulted storage. Transport and shuttle is based on the level of security alert. The use and release of the vaulted extractions is controlled by a set of rules or organizational policy which includes the following options among others: (a) A vaulting of some, all, or specific data object extracts for long or short periods of time. (b) Release of extractions into a display, in which the extracted data objects will reconstitute with the modified original data stream, the original data objects stream or original document. (c) Release of extractions into a projection display in order to project with the modified data stream, the original document while maintaining complete separation of the modified source data stream (the source modified by the extraction of data objects and insertion of placeholders) and the extracted data object streams. (d) Release of extractions into a projection display in order to project a reconstitution of the original document, in other words to create altered versions of the original document, while maintaining complete separation of the modified data stream and the extracted streams. (e) In situations of high security threats, release of extractions into another projection display, PDA, floppy disk, paper document a wireless display, an overlay transparency while maintaining logical and physical separation of delivery streams. This will enable working with a representation of the initial source, but not the initial source itself, while understanding the prevalent, critical extracted information without comprising security to the initial source material by exposing sensitive, identifying, or critical information. (f) The distribution of sources, modified sources, or extracts to remote and distributed viewing devices. (g) Enable the ongoing operation of information delivery and display in defiance of known ongoing or unknown security flaws, breaches, or events compromising the general state of security. (h) The delivery of distinct and separate data streams, delivered on the same or different channels and media, each with minimal, limited, or even substantial usefulness in and by itself, that can be overlaid logically or physically to reconstitute the identifying data stream and display. Separate display devices can be used to create a composite image or they can be overlaid to physically separate display devices to reconstitute a useful composite display.

The objective is to create security for the single computer or extended network. When an intruder penetrates preexisting firewalls and other security systems, the data object and streams, digital documents, and digital files which will be valueless and prioritized data objects rendered unidentifiable, the penetration is valueless because the critical strategic information has been exported to a vaulted storage. Competitors or hackers, who learn that a computer or network is protected by the system and method, might decide to attack another target instead. This is comparable to a situation in which a bank robber, who finds out that the bank vault is empty, will most probably look for another bank.

The system and method has a menu of different options including the ability to extract: (a) All existing databases on the computer or network. (b) All newly loaded, mounted, or integrated data to the computer or network. (c) All plug-in memory devices (temporary or permanent) containing data. (d) All new and imported data to the computer or network. (e) All new work and output created by the computer or network. (f) All data being transported in/out of the computer or network including electronic mail. (g) All data being transmitted in/out of the computer or network including electronic mail.

The system and method releases the extracted data streams, subject to a controlled-release mechanism and process. The release mechanism is contingent on parameters including; rights to access specific contents, timing criteria, security restrictions, and preset policies. The release of the extracted data objects permits restitution of the source data stream in variations of the source that are full, partial, or modified representations of that source data stream. The release provides for various levels (through user configuration) of separation between the modified source data stream and the extracted data streams. The system enables the maximum grade of security by means of the option of a visual merged projection of said different data streams, while maintaining a strict physical and logical separation between the data streams.

Basic Reconstruction

Figure 1B:
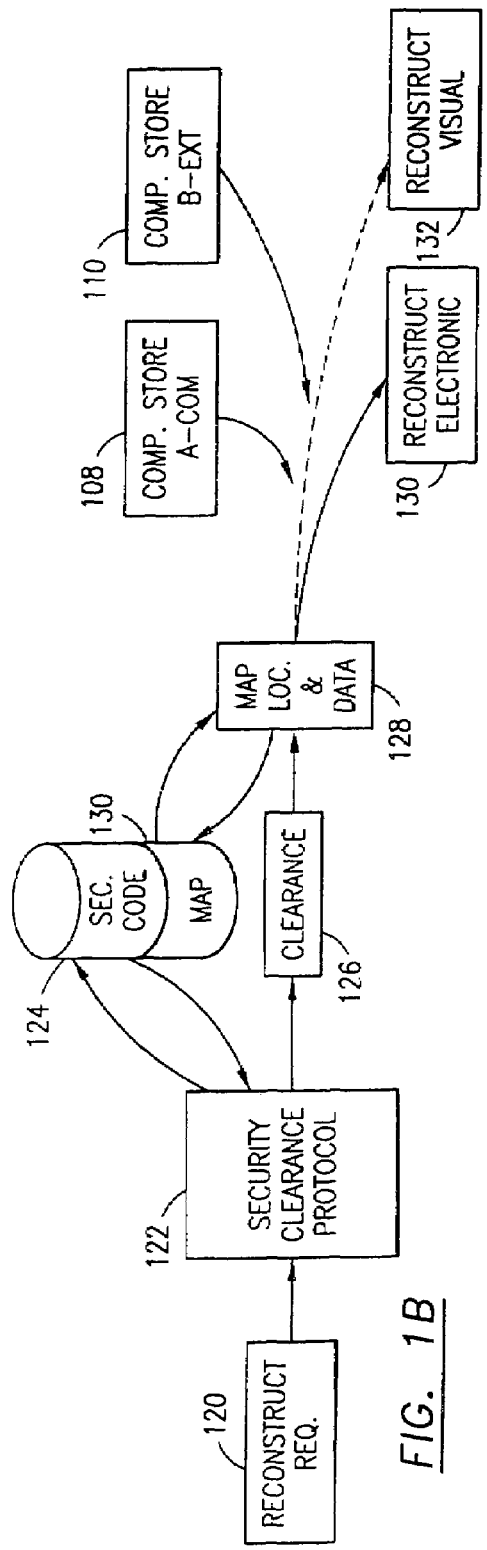
FIG. 1B diagrammatically illustrates a system diagram showing reconstruction of the data, various security clearances and both electronic reconstruction and visual reconstruction.

FIG. 1B generally diagrammatically illustrates the major features of a reconstruction routine or system. The user, typically at a computer terminal, inputs a reconstruction request 120. The system first executes a security clearance protocol routine 122 in order to determine whether the user has the proper security clearance. The security clearance may be thought of as a security clearance control. If multiple users are permitted access to the documents and those multiple users have different security clearances, the security clearance protocol determines the level of security clearance and, hence, the full or partial reconstruction of the plaintext. The security code input by the user is checked against a security code database or list 124. Clearance is provided in step 126. The location of the map and, hence, the location of the remainder data A-com 108 and extraction is provided to the user's computer in step 128. This may include obtaining a copy of the map 130 showing the location of memory segments in (a) the local computer; (b) the LAN or WAN; or (c) the Internet storage sites. The storage segments are A-com 108 and B-ext 110. The common or remainder data is downloaded or transferred or made available to the user's computer as shown at the output of map location and data step 128. Typically, the extracted or security sensitive data from B-ext is downloaded. As described hereinafter, the data can be reconstructed as a complete electronic document in function 130 or may be reconstructed only as a visual reconstruction in step 132. Visual reconstruction is discussed later. Function 130 operates as a compiler to gather the extracted data and remainder data into a single plaintext document. If the data object represents sound or audio signals, reconstruction and play back may require a speaker output in function block 130. In a telecommunications implementation of the present invention, the input would include a microphone or audio detector (supplemental to the input device for document 100), an analog to digital converter (possibly with a voice to digital converter), the filter, extractor, storage facilities at least for the extracted data, and at the output of the system, a converter to audio and an audio announcer. The recipient of the secured data stream or message would be required to clear a security clearance and possibly obtain a decoding key prior to listening to the entire, decoded message. The key and the security data is separately downloaded to the recipient's device.

If remainder data in A-com memory 108 and extracted data in B-ext computer memory 110 is encrypted, the reconstruction process includes a decryption step. Encryptors and decryptors are relatively well known by persons of ordinary skill in the art. Further, the filter 102 (FIG. 1A) may include some encryption routine operating on the data object (plaintext) during the filtering. A simple encryption may include substituting "dummy" text or images for the security words and keeping a pointer to an encryption key document mapping the security words with the dummy words. The filter may be stored or may be destroyed at the option of the user. Storage of the filter impacts the degree of security of the entire data system but storage of the same filter enables the user to reuse the filter at a later time. Encryption of the stored filter increases the security of the data. Creation and storage of map in memory 112 also impacts the degree of security of the system. However, if the filter 102 is destroyed and all copies of the map are destroyed on the user's computer originating plaintext document data 100, and the map is stored offsite in a third computer memory location 112, this offsite map storage may enhance the degree of security of the data. The originating computer processing plaintext 100 may be scrubbed to remove all reference and copies of the plaintext, remainder text, extracted data, map storage data, etc., i.e., a deletion routine may be employed on the data input computer.

System Configurations

Figure 2:
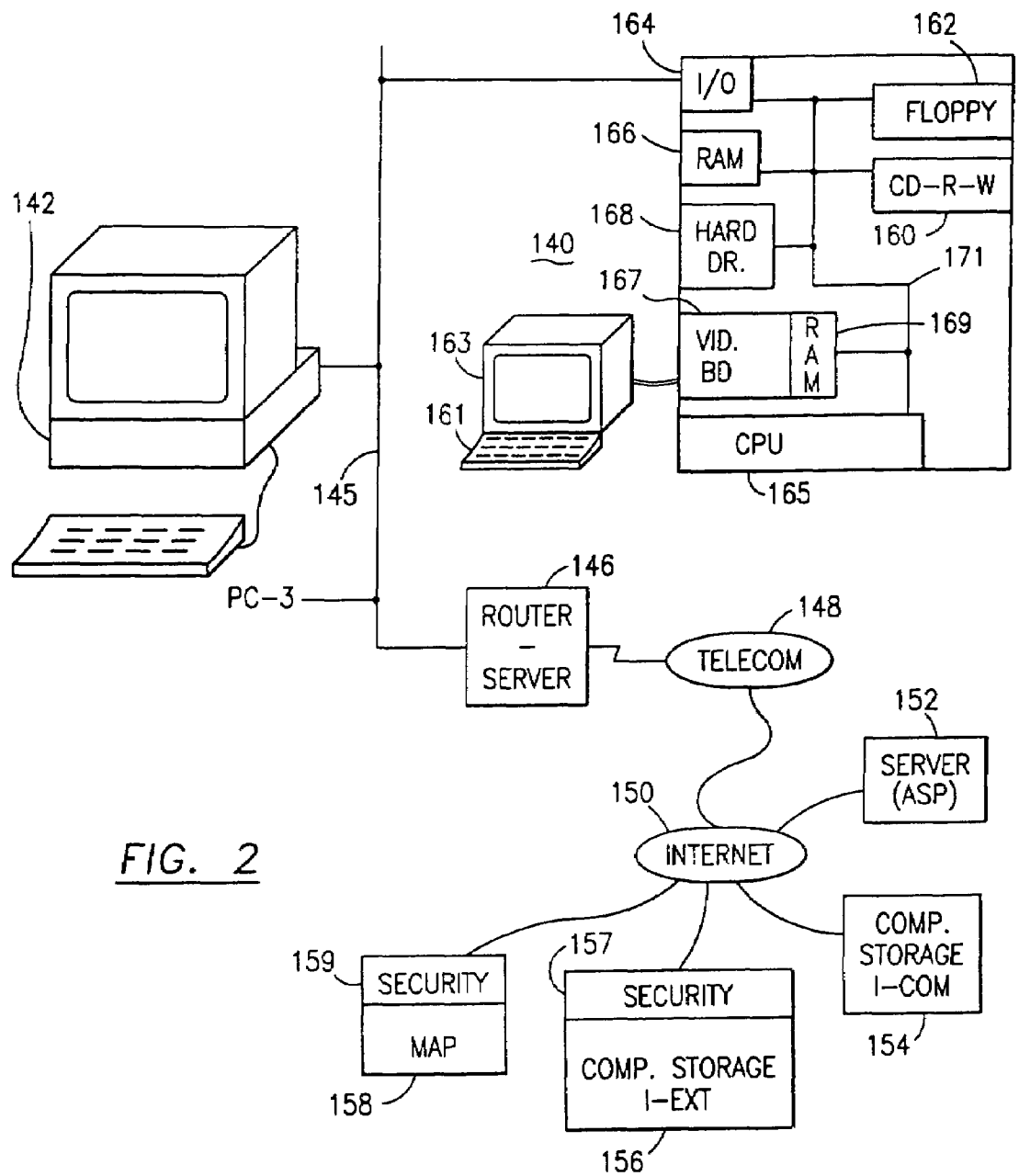
FIG. 2 diagrammatically illustrates a system showing major components of a single personal computer (PC) system, a networked system with several PCs (a LAN or WAN) and the network coupled to a telecommunications system and the Internet and shows the interconnection with a server and multiple, Internet-connected memory units.

FIG. 2 diagrammatically illustrates a personal computer or PC computer system 140, a second PC or computer 142, and a third PC-3. PCs 140, 142 and PC-3 are connected together via a network 145(LAN or WAN) and are also connected to an input/output device 146 that may be generally described as a router or a server to an outside communications system. The input/output device 146 is connected to a telecommunications system 148 which leads to Internet 150. The Internet is a global computer network. Internet 150 is coupled to a plurality of servers, one of which is server 152. Server 152 may be designated as an application service processor ASP. Internet 150 also includes various computer memory storage devices such as computer storage I-com 154, computer storage I-ext 156 and computer storage map 158. Computer storage enabling the store of extracted data includes a security level clearance module 157. Similarly, map computer storage 158 includes security level clearance module 159.

As stated earlier, the present data security system can be implemented on a single personal computer 140. In this case, different memory segments or hard drive 168 may be used for A-com and B-ext. Typically, PCs include a keyboard or data input device 161, a display 163, a central processing unit CPU 165, a video board 167 having video board memory 169, a fixed disc hard drive 168, a RAM 166, and input/output device 164, a removable media media or floppy drive 162 and a removable compact disk (CD)

read-write (CD-RW) device or drive 160. The system may include other removable disk drives, tape drives, or flash memory units. Internal units CPU 165, video board 167, hard drive 168, RAM 166 input/output device 164, floppy drive 162 and CD-ROM device 160 are all coupled together via an internal bus 171. Bus 171 represents a plurality of buses as is known to persons of ordinary skill in the art.

One methodology of implementing the present invention utilizes distinct memory segments which may be designated in one or more of the following: hard drive 168, memory in a removable disk in floppy drive 162, memory in a removable CD disc in CD-RW device 160, and, to a very limited extent RAM 166. In this manner, the user may select, generally at the outset of the process, that the extracted data memory storage B-ext 110 be stored on a floppy (removable memory) via floppy drive 162 or a CD via CD-RW drive 160. The user can then simply remove the floppy or the CD and carry it with him or her. To reconstruct the data, the operative program, generally discussed above would have access to the floppy or the CD and particularly the memory location of the data on the floppy and the CD in order to reconstruct the entire plaintext document 100 (see FIG. 1A). Alternatively, different portions of hard drive 168 may store A-com and B-ext. Of course, the computer system may utilize tape drives and memories or flash card, programmable memory.

In a local area network or wide area network implementation, PC 142 includes memory similar to memory units described in PC 140 and a memory segment may be set aside in PC 142 separate from the common data or remainder data storage typically placed on hard drive 168 in PC 140. As a further expansion of the present invention, the extracted data (that is, the high security data), may be stored on computer storage I-ext memory unit 156 via Internet 150, telecommunications system 148 and router/server 146. In this manner, the common data or remainder data is stored on hard drive 168 and the highly sensitive data is stored off site in a secured location. Access to that secured location may be limited via security layer 157. If the user implements an encryption system (see encryption e 118 in FIG. 1A), the extracted data is further secured by the encryption during the transfer from computer 140 through network 145, router/server 146, telecommunication system 148, Internet 150 and ultimately to computer storage I-ext 156.

The present invention may also be embodied utilizing an Application Service Provider on server 152 and in a client-server network.

An implementation of the present invention over Internet 150 most likely includes the use of a uniform research locator or URL for map memory computer 158, computer storage I-ext 156, computer storage I-com 158 and ASP server 152. In a client-server environment, server 152 acts as a server generally commanding the operation of client computer 140. Of course, persons of ordinary skill in the art recognize that the server may be located on the local area network 145 rather than being interconnected with Internet 150 as shown in FIG. 2. The claims appended hereto are meant to cover the alternative embodiments.

As an example of a client-server or web-based implementation of the present invention, the user at computer 140 may define the filter 102 as described above, and input data (plaintext) via keyboard 161 or load plaintext data from floppy drive 162 or CD-ROM drive 160 into RAM 166. In any event, whether the plaintext data is input via keyboard 161 or copied or accessed from floppy drive 162 or CD-RW drive 160, the plaintext data is filtered as discussed above in connection with FIG. 1A. Prior to filtering, it would be appropriate for the user at computer 140 to identify where the remainder data or common data will be stored and where the extracted or high security data would be stored. A simple program may automatically select the secure store location. The system is sufficiently flexible to enable the user to select local storage on different memory segments of PC 140 (hard drive 168, floppy drive 162, CD-RW drive 160) or be flexible enough to enable user at computer 140 to designate off site storage of the high security data (extracted data) and/or the common or remainder data. An automatic store routine may only require the user to accept or reject to preferred first security level, second security level and higher security level stores. The off site data storage process may include activating server 152 and enabling the server to take over the process directly from user 140. In other words, the user at computer 140 could call up the URL of the server 152, the server could request certain user information (user name, password), and would request data from the client computer to establish the filter pursuant to input selected by the user. The client computer may (a) filter the plaintext thereat or (b) send the data to the server for filtering. The server could store data either locally on computer 140 or remotely at computer memories 154, 156. After storage of the data at any of these locations, the server 152 may establish a map and store the map in memory location 158. Of course, remainder data (cleansed, plain-text data) and the map may be stored at ASP 152 or client computer 140. The map, if stored at map storage 158, may be downloaded to the user at computer 140. The filter may be stored at computer 140 or may be stored at a secured location on server 152. Alternatively, the map could be destroyed on user computer 140. The filter could also be destroyed on user computer 140. Of course, the filter could be stored in a fourth remote location (not shown), different from I-com 154, I-ext 156 and map computer memory 158. Storage of the map and decryption keys is a critical, high security task. Appropriate security measures should be utilized to protect those items. Local removable memory storage on disc in floppy drive 162 or disc in CD-RW 160 may be reasonable. All traces of the map, the filter, the encryption key, the extracted data, and possibly the remainder data may be scrubbed or deleted from all computer memories (by write-over or disc reformat routines) other than the "com" and "ext" storage sites. Deletion of all URLs, links, x-pointers, etc. is also recommended for high security applications. Deletion systems are known to persons of ordinary skill in the art. For multiple security levels, multiple web site for storage of cleansed plaintext, first, second, third and higher security level extract text is preferable. Where the community of interest has access to the targeted and protected data via the Internet, multiple secured storage locations, multiple stores for filters, for encryption keys and for maps locating the secured stores is provided by multiple storage locations distributed throughout the Internet.

To reconstruct the document, the user at computer 140 would be required to call up the URL of server 152 and input the appropriate security code. The server 152 would then call up and download data from various memory locations whether they be memory locations on computer 140 or memory locations I-com 154, I-ext 156 and map memory 158. The system compiles the entirety of the plaintext document by gathering the dispersed components thereof or compiles partial reconstructions for different levels of security. By implementing different security levels, the system is dynamic enough such that server 152 can easily locate the various extracted data levels based upon various security codes representing different security levels, as those codes are input by the user at computer 140. Multiple security codes, at the inception and during the process, may be utilized. The user may be required to input security codes at multiple times during the reconstruction or compilation process.

It should be noted that computer storage 154, 156 and 158 may be located on the same computer or may be located on different computers spread throughout the Internet. If the storage units are different computers spread throughout the Internet, computer storage 154, 156 and 158 would each have their own URL or Uniform Resource Locator. In any event, during reconstruction, the server 152 gathers the information and downloads the information into RAM 166 of computer 140. This download may include a first download of the common or remainder data from I-com 154. At a separate time, which may or may not include a decryption routine, the extracted from I-ext 156 is downloaded. Preferably, other than inputting initial security codes and any required or desired intermediate security codes, the system operates automatically without further input from the operator at client computer 140. The download of both data sets may be simultaneous in that the download is not humanly perceivable. This is especially true if storage in different memory locations in PC 140 is utilized.

The role of server 152 may be expanded or reduced dependent upon the desires of the user and the degree of security necessary. For example, server 152 may only enable separate storage of extracted data in I-ext 156. In this limited role, server 152 would require the input of a proper security code and clearance prior to identifying and enabling the download of extracted data from I-ext 156.

In an expanded mode, server 152 may be involved in filtering the data, extracting the security sensitive words, characters, icons or data objects to obtain extracted data and remainder data thereat, separately storing the extracted data from the remainder data (extracted data being placed in computer memory I-ext 156 and remainder data being stored in common remainder data memory I-com 154) and then permitting reconstruction via separate or combined downloads of the reminder data and the extracted data into computer 140.

The innovation is a system and method for automatically or manually controlled selection, extraction, storage, and release of selected and prioritized information. The system extracts selected information from data streams, in computers, computer networks communication devices, and net works, as well as electronic mail systems. The system and method can reside on a single computer, be distributed across multiple platforms, be distributed across multiple networks, or reside as a remote process (known as a hosted application service process in the state of the art).

Reconstruction Techniques

Figure 3:
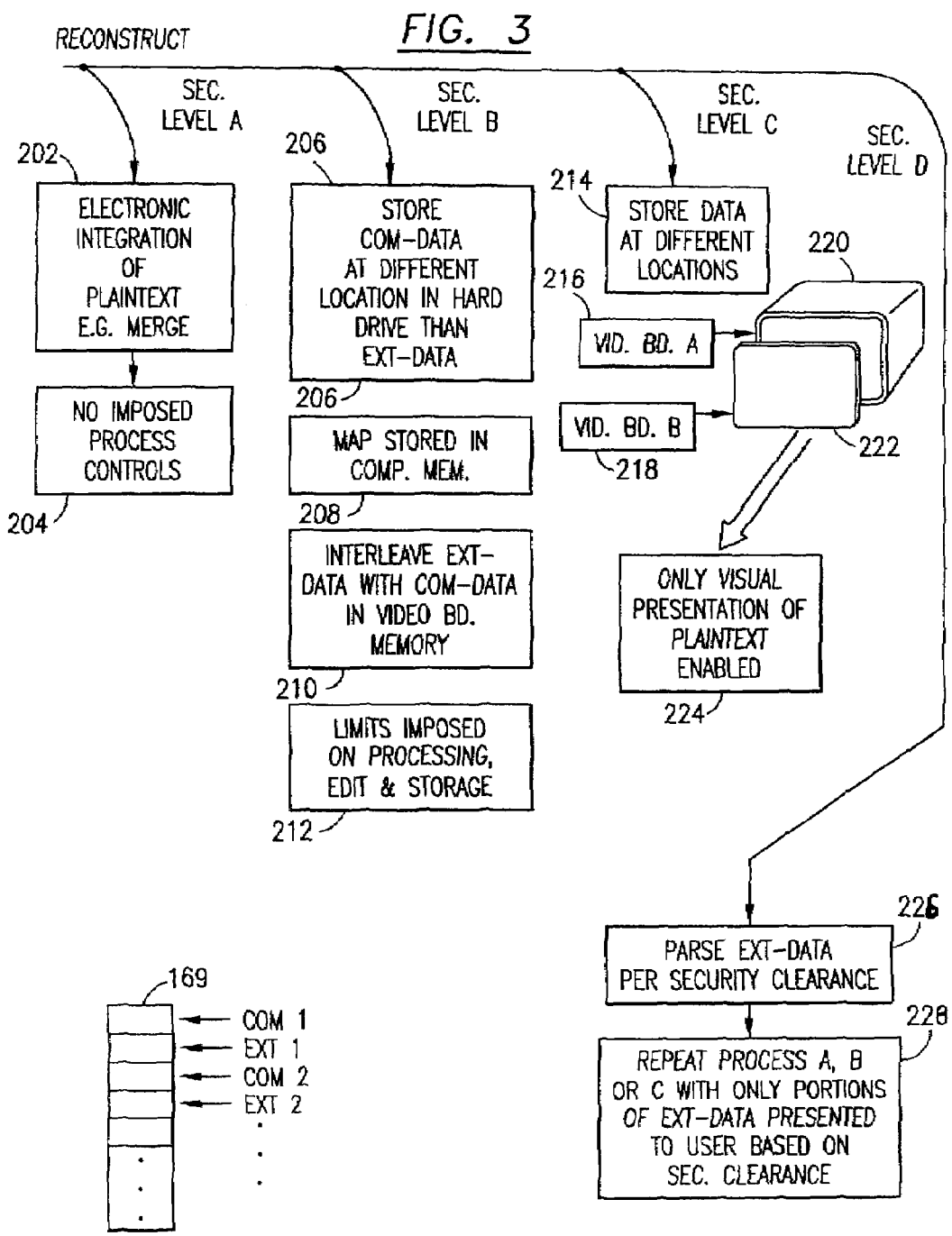
FIG. 3 diagrammatically illustrates a basic flowchart showing reconstruction for various security levels.

FIG. 3 diagrammatically illustrates a system diagram for various reconstruction routines. A complete reconstruction is shown as security level path A. This involves an electronic integration of plaintext in step 202 resulting from the complete electronic reconstruction of document 100. For example, a merge may occur between the extracted data and the remainder data or common text data. The document is completely compiled in this process. Placeholders in the reminder document are utilized to locate and insert the extracted data. Most likely, there will be no process controls imposed on the integrated document as shown in step 204. In other words, if the user at computer 140 has the proper security clearance, he or she could download or recreate the entire original source, plaintext document and the user would be entitled to edit the document or change it in any way or copy it and reproduce it.

The second level of security, path B, results in storage of the common or remainder data in a different memory location on the hard drive 168 as compared with the extracted data. This is noted in step 206. Another words, in a simple example, hard drive 168 or RAM 166 would hold a copy of a remainder data document and another copy of the extracted data document, that is, two separate documents. Since two documents are available in RAM 166 or hard drive 168, these documents are stored in different locations in the memory. In step 208, a map showing the memory location of the common or remainder document and the extracted data document is provided to computer 140. Step 210 commands the processor CPU 165 in computer 140 to interleave the extracted data with the common or remainder data in the video board memory. In this process, the extracted data would typically have placeholders for the missing remainder data. Otherwise, control codes to locate the extracted data into the remainder data would be executed by CPU 165 to properly place the extracted data into the "visual space" of the placeholders in the remainder data document. The extracted data document may have placeholder for the remainder data. Some type of register between the two image documents may be necessary. The compiler, in this embodiment, gathers the document elements and visually compiles and presents the plaintext to the user.

FIG. 3A diagrammatically shows that video board memory 169 is loaded with remainder or common data 1 and a different location of the video memory is loaded with extracted data 1. The next video memory location is loaded with common data 2 and then a different video memory location is loaded with extraction data 2. Since the refresh rate of computer monitor 163 is fast, the display 163 will show the common or the remainder data and then show the extracted data such that the user could not humanly perceive a difference in the document. However, the user could not copy the document from display screen 163 (a "screen shot") since the document is never electronically integrated into a single document. There is only a visual presentation of the combined document by interleaving the extracted data with the common or remainder in the video memory 169. Step 212 notes that the user may be limited in his or her ability to process, edit and store the reconstructed and presented plaintext document.

Security level path C recognizes in step 214 that the data is stored in different memory or computer locations. In this situation, two video boards, video board A and video board B are shown as board 216 and 218. Video board 216 drives display monitor 220. Video board 218 drives display monitor 222. Display screens 220, 222 are overlaid atop each other. Video board 216 is fed with common or remainder data from the remainder data store (see I-com store 154 in FIG. 2) and video board 218 is fed with the extracted data from the extracted data store, for example, I-ext store 156. In this manner, as noted in step 224, the user is presented only with a visual presentation or compilation of the plaintext. Since there was physical separation between video monitor 222 and video monitor 220, there is no electronic integration at all of the plaintext document. Hence, the ability for the user to do any significant editing on the plaintext document is blocked or prohibited because the user only has access to either the data on video board 216 or the video board 218.

Security level path D shows that the extracted data may be parsed or further separated based on a plurality of security clearances in step 226. Step 228 recognizes that the system can repeat process and security process paths A, B and C only with portions of the extracted data presented to the user based upon the user's security clearance.

General Operation

Figure 4:
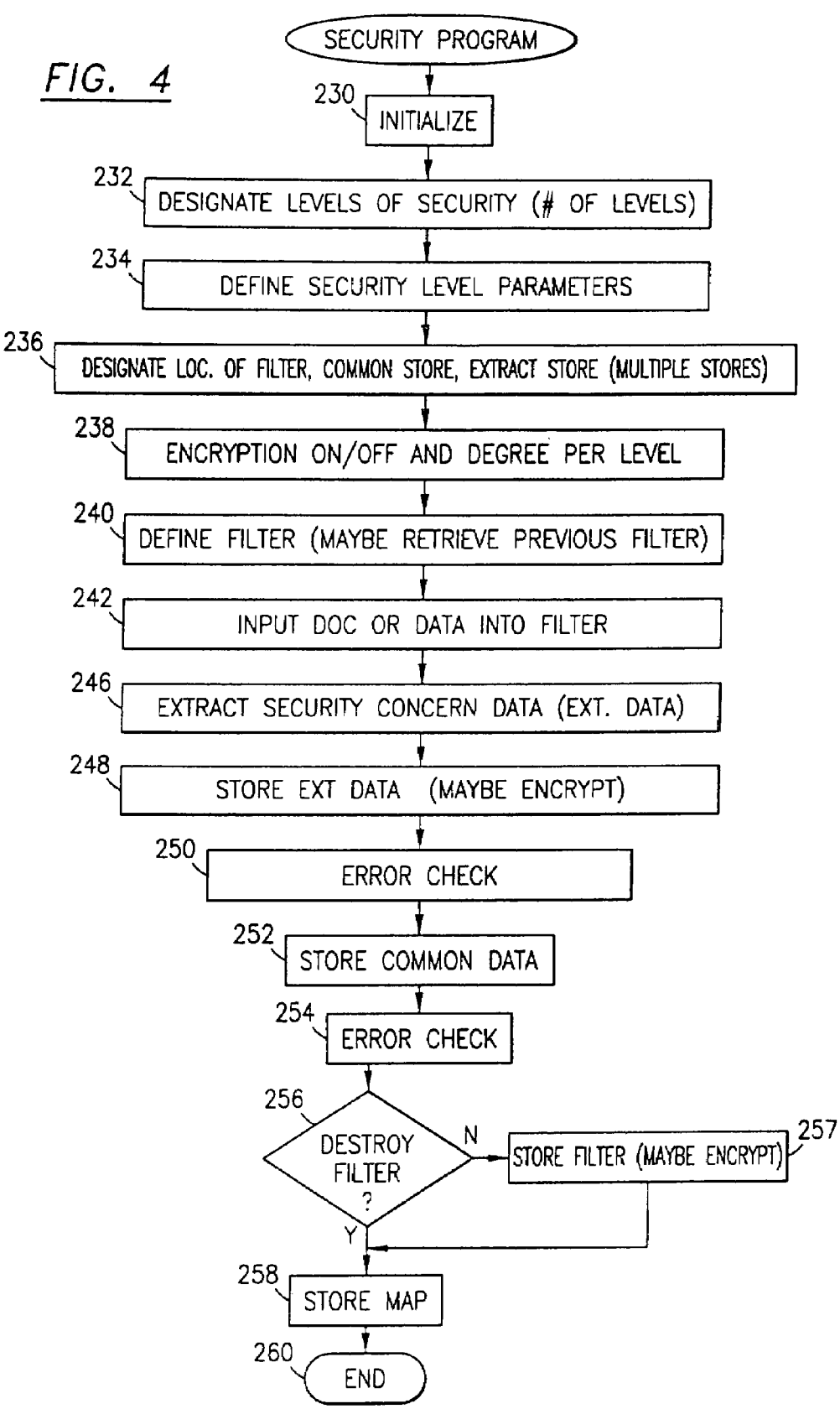
FIG. 4 diagrammatically illustrates a flowchart showing one embodiment of the principal portions of the data security program.

FIG. 4 diagrammatically illustrates the major components of a flowchart for the data security program. It should be noted that this flowchart may be truncated to limit user selection of certain items. The system would be pre-set to contain these features. Step 230 initializes the system. Step 232 enables the user to designate various levels of security for the activity which he or she will soon engage. The system, in step 234, enables the user to define the levels of security parameters. The following Security Table gives some examples of the type of security that may be available to the user.

Security Table to whom
to where
when (time of day, day of week, month, floating but predetermined time frame)
why (purpose, match purpose to other security parameters or to certain predetermined criteria)
how (through what medium (LAN, WAN, Internet, direct dial link), download to what site or destination)
how long (duration) the reconstruction process will be permitted per each security clearance level
how much (different security levels enable reconstitution of documents and data with different amounts of secure data therein)
timing systems may require synchronization for a standard clock (i.e., atomic clock)

As an example of a truncated or pre-set program, a client-server system over the Internet may have URLs designating storage sites and an ASP 152 (FIG. 2) controlling storage. In this pre-set system, the user does not select the sites. The sites may be randomly selected by ASP 152. The ASP may use artificial intelligence AI to locate secure extract data storage sites. AI or inference machines can ascertain (a) traffic on communications channels, (b) storage limit issues, (c) transmission failures in the communications links, and (d) the degree of security necessitated by exterior events, i.e., terrorism alerts, virus alerts, war, data security warnings posted by trusted sources, MicroSoft, Norton, NASA, DoD, CDC, FBI, etc. Higher security alerts trigger the AI configured storage locator and facilitator to locate memory stores in higher secured places. These higher security facilities may be more costly, may be located in more stable countries or on more stable servers and may have greater degrees of encryption capabilities.

The user, in step 326 can designate the location of the filter, the common storage area for the remainder data, the extraction data storage and potentially multiple data storage areas or segments. The user may enable an AI filter design. Step 238 permits the user to engage or disengage encryption and, if engaged, establish the degree of encryption for the system. Step 240 enables the user to define the parameters of the filter. The user can retrieve a preexisting filter or may define a new filter for each data security session. These filters may consist of dictionaries or any type of compilation of words, characters, icon, data objects or pixel formation or any indication that can be perceived by the computer system. Granular extraction of data elements in a data object may be permitted. Step 242 recognizes that the user either inputs a preexisting plaintext document or types data into the system. In any event, the plaintext document is fed through the filter. Step 246 extracts the security data from the input document. Step 248 stores the extracted data. The extracted data may be encrypted prior to storage. Step 250 conducts an error check on the extracted data. This error check is helpful in discerning problems in the storage of the data prior to closing down the data security system. Step 252 stores the common data or the remainder data. Step 254 conducts an error check on the common or remainder data. The decision step 256 determines whether the user has selected a "destroy filter" command. If not, the filter is stored with or without encryption in step 257. If YES, the filter is destroyed with a deletion routine. Typically, deletion is complete erasure of all traces of the file including, in high security systems multiple write-overs or disc reformatting. Step 258 stores a map. The map may be stored locally or remotely as described earlier. The system ends in step 260. All traces of these data elements or objects may be swiped clean or removed from whatever computer system generated the data objects or processed them, other than the memory storage locations. Deletion of data also includes the concept of deletion of data transmission paths, URLs, storage site locations and all temporary memory stores. Deletion of file location in the root directory of hard drive 168 of computer 140 is preferable in high security systems.

Figure 5:
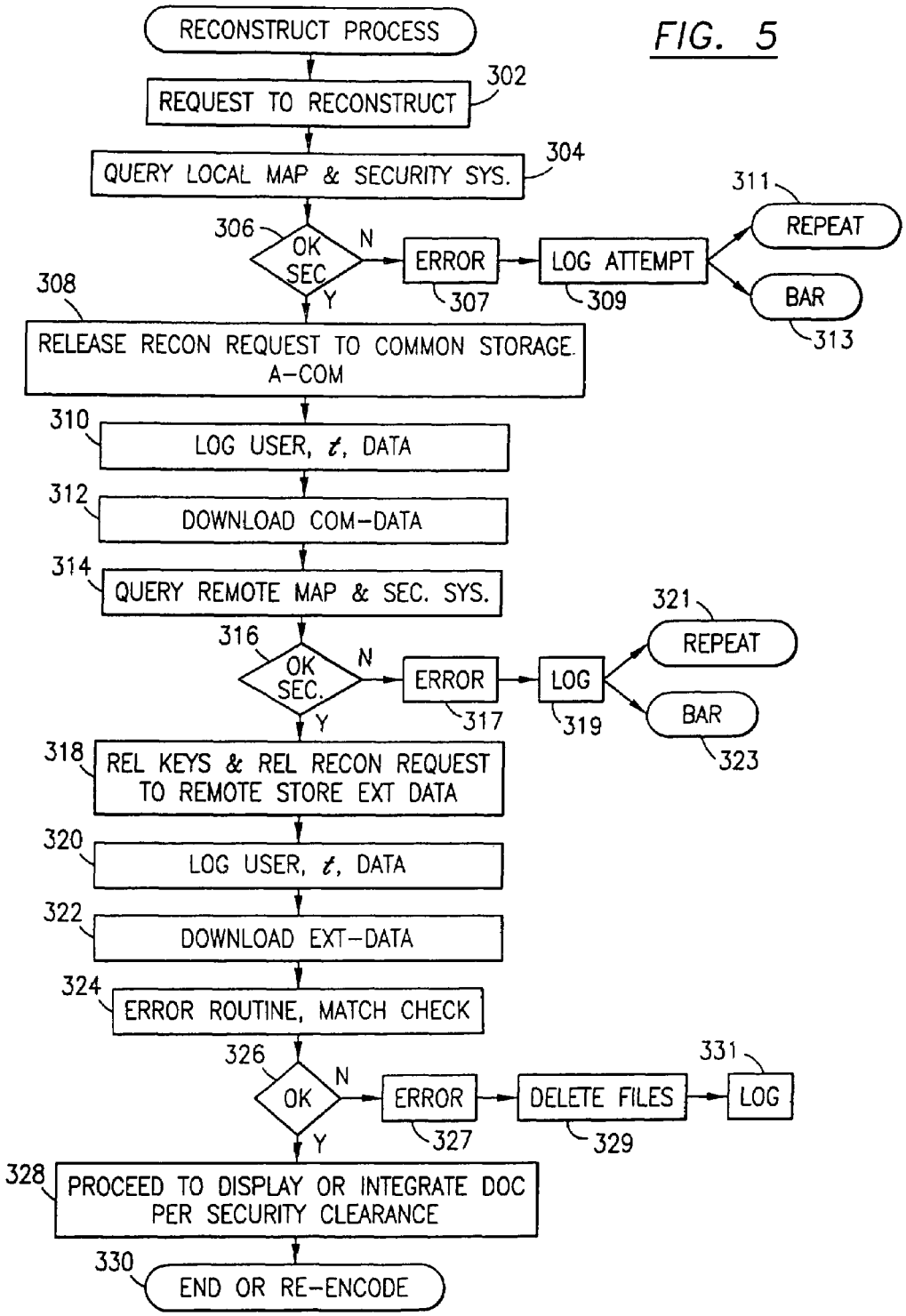
FIG. 5 diagrammatically illustrates a flowchart showing the basic elements of the reconstruction process for the data security program.

FIG. 5 diagrammatically illustrates basic flowchart features for the reconstruction process. Step 302 accepts a request to reconstruct the secured data. Step 304 queries a local map and the security system or protocol. In a preferred embodiment the user would have to input several passwords, one of them being a local password on computer 140. A local map which may be accessed only through the password, may simply identify the URL of server 152. Decision step 306 determines whether the local password is acceptable. If not, and error step is indicated in step 307, the attempt to log on to the security system is noted in step 309 (an audit trail), and the system either branches to repeat step 311 or bars the user from further activity in step 313.

Returning to decision step 306, if the password is locally acceptable, the YES branch is taken and the system executes step 308 which releases a reconstruction request to the common storage facility I-com 154 or A-com 108 (FIGS. 2 and 1A-B). The system in step 310 logs the user in, as well as time and date and the data regarding the request. In step 312, a download from the common data storage is provided to RAM 166 or hard drive 168.

In step 314, a query is made to obtain the remote map from the remote security system. The decision step 316 indicates that the user again successfully inputs his or her security code. If not, error routine 317 is activated, the password failure is noted in step 319 (an audit trial), and the user is given an opportunity to repeat in step 321 or is barred or prohibited from further activity in step 323. If the user has correctly input the security code, the system in step 318 releases the keys (to decrypt) and the map and releases the reconstruction request to the remote storage for the extracted data. This could be computer storage I-ext 156 or computer storage B-ext 110. In step 320, the user's access to the extracted data is logged in along with the time and day and type of data request. In step 322, the system downloads the extracted data into RAM 166 and/or hard drive 168 of computer 140. In step 324, an error routine is operated on the extracted data in order to insure that the extracted data properly matches the common or remainder previously stored. Decision step 326 determines whether the error routine properly generates the correct count or output. If not, the system in step 327 indicates an error, in step 329 the system deletes the common files and the extracted files and the system in step 331 logs in the failed attempt. If the error checking routine on the extracted data is acceptable, the YES branch is taken from decision step 326 and the system, in step 328, proceeds to display the plaintext document or to integrate the plaintext document pursuant to the security clearance initially input by the user. Step 330 ends this process. The end process may entail encrypting the data again and swiping clean all traces of data objects from the memory stores and computer handling units. Of course, every use of encryption requires decryption of the data prior to reconstruction.

The system may incorporate various types of security systems or routines.

pass word pass phrase multiple choice questions and answers initial, intermediate and subsequent security clearance routines biometric security routines (voice, fingerprint, signature, eye or retina scan)

The reconstruction routines may be interrupted or the security system automatically activated or initiated upon the occurrence of externally generated triggers or upon certain predetermined conditions or conditional events. Limited extraction, security clearance, release of data and reconstruction limits may be imposed. Artificial intelligence (AI) engines, inference engines or neural networks may be implemented to vary the permitted level of reconstruction via the security clearances. In other words, the AI system, as applied to reconstruction, may, relatively independent of the filter and storage processes, increase the necessary security levels permitted to access and generate full or partial plaintext recreation.

The display systems 220, 222 in FIG. 3 include CRT monitors, LCD screens, projection screens and combinations of those systems.

The audit trail to monitor reconstruct and reconstruction attempts may include adding a time/data stamp to the remainder data and/or the extracted data prior to storage and a cross-check to the audit trail log during the reconstruction process.

Placeholders in the remainder document may be:

blank spaces data symbols or elements or "- - - " or "xxx"

false data clearly erroneous data "ABC Company" or "Baker"

chaff or hash marks messages bar code serialization data alerts links to other data objects null set indicators "[ ]"

URL or website addresses

It is believed that the present invention is faster, during reconstruction, than standard encryption techniques, on the order of 100 to 1,000 faster.

Automatic Features

The system and method described herein may operate substantially automatically, that is, without operator intervention, other than the security clearance function. The clearance function does require some type of operator authentication prior to retrieval of the extracted and remainder data.

The system and the method may operate automatically in that the plaintext or originating data could be identified by a party desiring security. The system could obtain that data from any data input device (hard drive memory, floppy drive memory, flash card memory, personal data assistant (PDA), or any other type of data input device), filter the data, separate the extracted text or the remainder text, encrypt (or not encrypt) the data, separately store the extract and remainder data (all automatically, that is, without operator intervention). Hence, it is not necessary that the system operate with significant operator or manual intervention, Of course, the system may also operate on a plaintext document or data object that is being created "in real time" by an operator and keyboard, mouse or other type of data input device. Since the present system can be configured to operate in real time, the system works on data packets of sensitive text, characters, icons, images or a combination thereof, sound, video, and data objects in general.

The automatic operation of the system and the method can be caused by a triggering event. This triggering event may be a security attack (generating a trigger to start the gathering of plaintext, filtering, extraction and storing) or may be any other type of trigger such as a building burglar alarm, door alarm, fire alarm, or virus detection algorithm trigger. The event may be a time of day, week or month. It may be n seconds after the user stops typing on a keyboard. It may be a timed back-up feature.

Multiple Security Levels

Multiple filters may be utilized in the system and in connection with the method. These multiple filters may be useful in the operation of the system with a plurality of security levels. Each filter could filter out different levels of security sensitive items and each bundle or group of security sensitive items (from each distinct filter) could be stored at different computer storage locations. Multiple filters, multiple security levels and multiple storage areas may also include multiple encryption routines and decryption routines. Encryption and decryption routines can be related to the level of security of a particular group of data.

Multiple maps may also be provided for singular or multiple storage of extracted data and remainder data. These maps may or may not indicate the originating point of the data. Maps can be parsed such that an intruder, upon discovery of a single map or map portion, could not locate the storage locations of all piece of the extracted data and remainder data. maps may also be encrypted. The map may also be stored at a distinct map store location.

The concept of partial reconstruction also includes the concept that a portion of the plaintext would be reconstructed and the unreconstructed portions of the plaintext could be encrypted or could show blanks or other symbolic indicators. See the placeholder table above.

Partial reconstruction of the plaintext also includes a concept that the security sensitive items or materials may be subject to different types of encryption. Hence, a single plaintext document may have multiple levels of security and multiple levels of encryption wherein each encryption has a different level of security assigned to it.

The present invention can also be configured to provide a computer network which transparently establishes and manages the separation of user-based communities of interest. The separation is accomplished by extraction pursuant to security levels, dispersion of data into secure storage facilities (memory stores) and reconstruction based upon the assigned security level. A low level security clearance results in only partial reconstruction of the plain text or source document. These user-based communities of interest are a plurality of users each having respective security clearances. As described above, each successively higher level of security clearance permits the user to see greater degrees of reconstructed plain text obtained from the extracted data stored in extract stores and the remainder data from the remainder stores. By integrating encryption (and necessarily decryption), separation of user-based communities of interest are established such that the users in a particular community are permitted access to some or all of the plain text data based crypto-graphically separated communities and need to know security levels.

Figure 6:
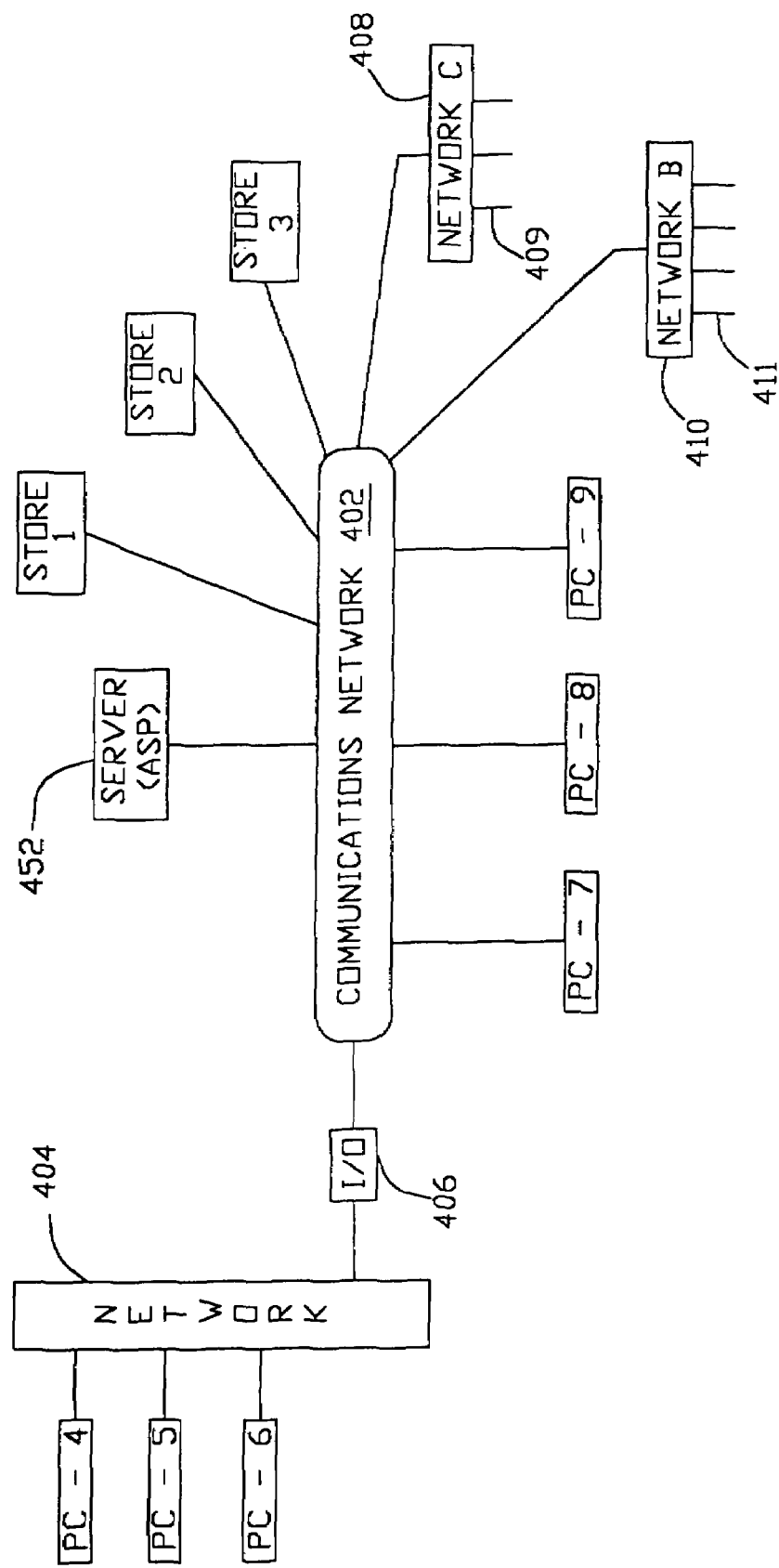
FIG. 6 is a computer network diagram showing various user communities.

FIG. 6 is an exemplary computer network diagram showing various user communities. The telecommunications network 402 is connected to the server application server provider ASP 452 and to various networks and personal computers or PCs. The PCs may be computer work stations. Network A 404 is coupled to telecommunications network 402 via an input/output unit 406. Network A is coupled to various PCs identified in FIG. 6 as PC-4, PC-5 and PC-6. Of course, Network A could be coupled to other PCs not illustrated in FIG. 6. As described earlier, server 452 can facilitate remote or offsite storage of extract data and remainder data in store 1, store 2 and/or store 3. Further, the map showing the storage location may be encrypted and stored in any one or more of these stores. Also as described earlier, the memory in one of the PCs, for example PC-4, PC-5 could be utilized to store extract data and remainder data from PC-6 and PC-6 can be configured as the input data computer. Hence, the present system and methodology encompasses the concept of local storage and remote storage. On the local level, the storage begins by storing the extract data at different locations in the hard drive of the PC. The next level higher is storing the extract data in removable computer media such as floppy disk, removable tape drives, CDs etc. associated with the PC accepting data or associated with a server on Network A. The next higher level of extract store is storage of the extract data on a server or other computer in a particular network. If PC-6 is designated as the input computer, the extract data may be stored on PC-4. Of course, PC-4 could be designated as the server for Network A.

PC-7, PC-8 and PC-9 are coupled to telecommunications network 402. Network C 408 and Network B 410 is coupled to communications network 402. The lines, one of which is line 409 extending from Network C 408, represent a plurality of computers or workstations coupled to Network C. Line 411 represents a plurality of workstations or computers coupled to Network B 410. In an e-mail implementation of one embodiment of the present invention, PC-7, PC-8, etc. may represent computerized devices accepting e-mail (personal data assistant, pager, cell phone, etc.). The sender and the e-mail addressee may utilize simple computerized systems to communicated via e-mail. Further, the network may be any telecommunications network including wire, cable, cellular, wireless, satellite, IR or RF systems.

Figure 7A:
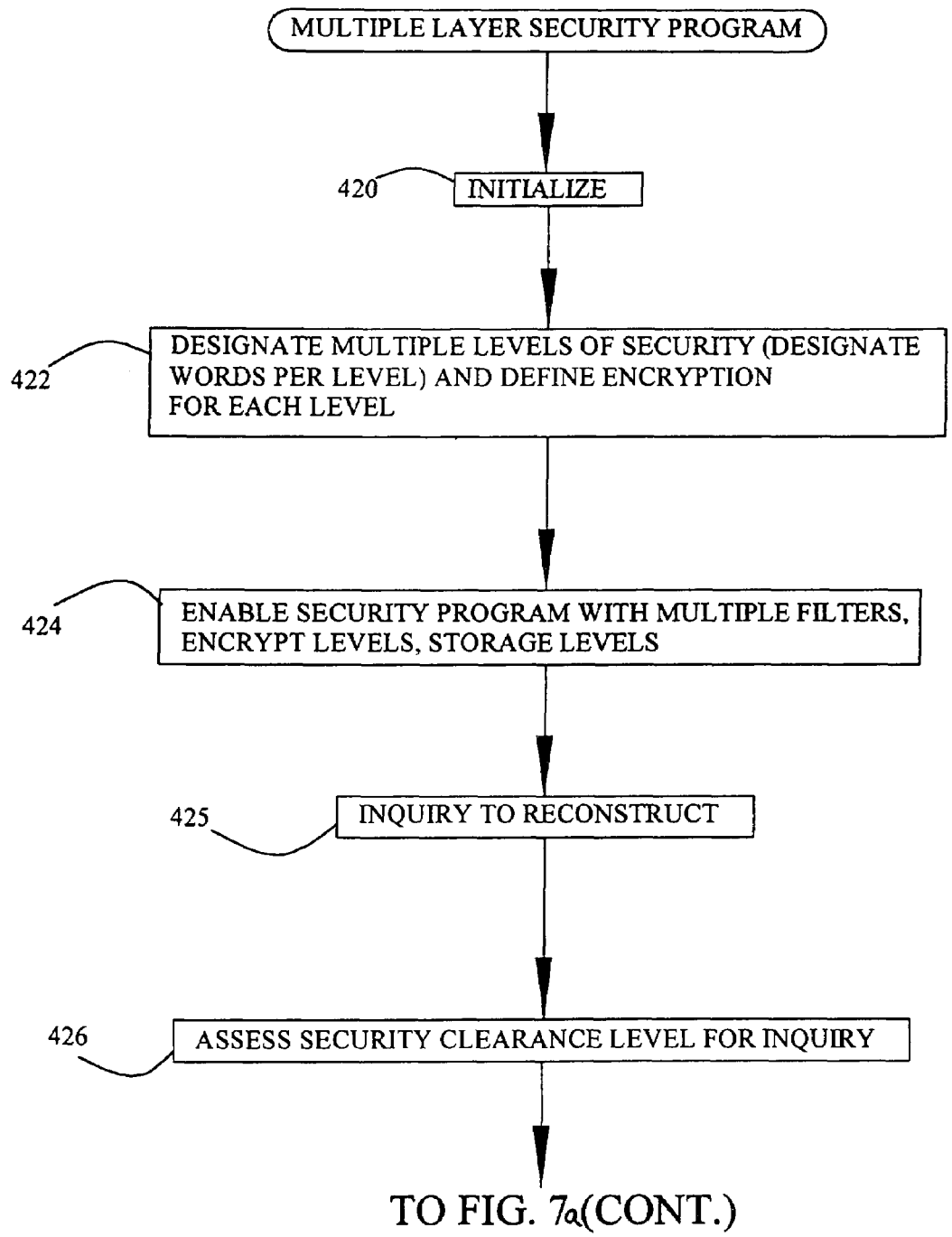
FIG. 7a diagrammatically illustrates a flowchart showing the key component steps for the multiple layer security program for the community of users.

FIG. 7a diagrammatically illustrates a flow chart showing the key component steps for the multiple layer security program for the community of users. The "community of interest" system described herein enables persons and organizations at the same security level to share data on a peer to peer level. Further the security system may operate automatically, with respect to extraction, storage and reconstruction, such that the peer to peer dissemination of data objects is quickly and readily available to all at the same or higher security levels. Step 420 initializes the program. Step 422 enables the user, administrator or system operator to designate multiple levels of security, that is, multiple words, characters, icon, data objects, or whatever, for each security level and further to define encryption for each security level. The designation step 422 also includes identifying the communities of interest and the particular security level and security clearance for each community of interest. One example of various security levels for communities is set forth below in the Community Security Level Table which is keyed to the computer network diagram of FIG. 6.

Community Security Level Table

| Security level | Community Group |
|---|---|
| High | PC-7; PC-8 |
| Medium high | all high group plus Network B |
| Medium | all above plus Network A |
| Low | all with nominal clearance |
| Special set medium | PC-7; PC-9; Network B |

Further, designation step 422 will include identifying the words, phrases, icons or data objects subject to security concerns and the potential location of the extract data and, if necessary the remainder data and the degree of encryption. The following Selection Table provides some examples.

Selection Table

| Level of encryption/storage | type or category of word or phrase; input specific word, phrase |
|---|---|
| High, web-based storage | dollar values, names of streets, countries, "Smith" and 5 words about "Smith," "avocado" |
| Medium high, remote storage | all addresses, all names |
| Medium network storage | all family names, all client names |
| Low, encrypt and separate store in local memory | all items not in dictionary |

As an example of various encryption methodologies, the following Encryption Table is illustrative.

Encryption Table

DES, random pad A ("r. pad A")
Huffman, r. pad B
Crypto API, r. pad 7
Two fish, r. pad C-2
Blowfish
RC4
Skipjack Ghost In FIG. 7a, step 424 executes or enables the security program with multiple filters, multiple encryption levels and multiple storage levels. Each one of these filters, encryption levels and storage levels correspond to the security level for the various communities of interest. Step 425 responds to an inquiry from a user to reconstruct the document. Step 426 accesses the user's security clearance and the particular inquiry. Decision 428 determines whether the inquiring party is entitled to full or partial access to the source document. If not, the NO branch is taken and the system, in step 429 adds placeholder substitutions. Step 429 may be optional. If YES, the system reconstruct pursuant to the clearance level in step 430. The following provides an example of multiple level encryption utilizing placeholder substitution.

EXAMPLE

Multiple Level Encryption

Applicants must be_____zzxx xx_____xxx_____citizens and have a high school diploma or equivalent. They must possess a valid subsubsub driver's license and qualify for top SUBWORD_____clearance.

With this multiple level encryption, substitutions may be utilized "subword" to indicate to the user with a less than superior security level that a certain word, term or phrase has been extracted and stored by he or she is entitled to know that substitute word, term or phrase has been inserted into the plain text document. Of course, any type of substitution character may be used for the placeholder.

In step 432, the system displays the plain text in a normal format or utilizing a split or bifurcated video memory or utilizing overlay display screen. FIG. 3 and the description of that figure set forth above describes the normal display in steps 202, 204, the split video memory display in steps 206, 208, 210 and 212 and the overlay display system in steps 214, 216, 218.

The system, in step 434, monitors and logs the location of the user making the inquiry, the type of inquiry, the time, day, date, clearance level and access level and logs all modifications to the plain text source document. One example of the log is set forth below in the Security Report Table.

Security Report Table

Privacy Scrubber Report
   source file: path\filename
   scrubbed file: path\filename-scrub
   source file: date, time, size
   process: date, time
   user: name
   system: name
Recovery File
   (a) storage location, type of encryption, random key
   (b) storage location B . . .
   (c) store C . . .
   (d) store D . . .

Step 436 enables the security program and parses and extracts the data per the security program, filters the data, extracts it and codes it disperses it and stores it as discussed above. The multiple layer security program ends in step 440.

The following Security Level Access Placeholder Table is another example of the type of placeholder substitutions that may be available. The example in the Security Table Access Placeholder Table may be used in conjunction with step 429.

Security Level Access Placeholder Table

[security level 2] intelligence located [security level 4] 20 miles from [security level 4]. He is using the name [security level 4], and dressed as a [security level 4] preacher. With him are his lieutenants, [security level 4] and [security level 4]. He is communicating with the international media through Mr. [security level 4], who resides at [security level 3], [security level 4], [security level 4]. Telephone is [security level 1] and Facsimile is [security level 1].

It should be noted that in order to reconstruct some or all of the plain text source data, some or all of the subsets of extracted data from the extract stores will be utilized dependent upon the respective security level of the inquiring party or user.

Sharing Data with Different Security Levels—Data Mining

The present invention can be configured to overcome obstacles to intelligence sharing and data sharing between parties by enabling the parties to identify granular critical data and control the release the granular critical electronic data subject to a sharing arrangement with other parties. In some instances, the controlled release process is designed to implement an agreed upon plan to share secured data based upon arms length negotiations between the parties. The invention enables a party to release specific granular data such as a name, address, or date without releasing the entire "classified" document. In a commercial context, this is akin to data mining in that the inquiring party seeks limited data (not the entire data file, record or document) and is willing to pay for the "mined" data. As an example of a security intelligence system, a local police chief may release granular critical data about a suspect to a federal agency, when in return the federal authority will release further intelligence "mined" or obtained for the secured data storage, about the suspect. The controlled release of data from the higher security level party (the FBI) may be an intelligence document or a granular part of it (a partial reconstruction provided to the local police). The rational behind this implementation of the invention is that there are many obstacles for sharing intelligence and information. There are even many more hurdles when it comes to sharing of raw intelligence. The invention creates a leveled playing field in, which the different parties must share and exchange information in order to achieve their objectives.

The invention can be configured to resolve the major challenges facing government by enabling sharing of information between its different organizations in relationship to fighting terrorism. The invention for example can enable organizations, connected to the Homeland Security Department, to search data bases of various other government, state and local organizations, eliminating the fear of the "source" organizations, owning or controlling the source or plaintext documents that their proprietary data or granular critical data is released without their specific permission. The invention enables open negotiations between the parties regarding what data to release and for what consideration. When several organizations are seeking access to a specific document, the invention and can allow a controlled release of different granular data to different parties for different considerations and benchmarks.

The invention's mechanism of controlled release of the located document/data enables other parties to search their documents without the fear that sensitive information will be released to the searching party. This invention is designed to foster sharing of documentation between different parties, taking into consideration the need to limit the access of other parties to the total content of the owner's document.

The invention is a machine and process and its purposes and advantages may be as follows: (a) To automatically control selection of data objects within a data stream and release them in a controlled method only to authorized parties. (b) To automatically separate data objects within a data stream into two or more digital data streams according to the importance and categorization of contents, through extraction and removal of the prioritized content and its replacement by appropriate placeholders. (c) To automatically control selected contents in E-mail, and enable its release in a controlled method only to authorized parties. (d) To enable users to leverage the growth in computer and telecommunications connectivity and electronic commerce by reducing security risks. (e) To enable users to release documents, digital files, and data streams into closed and opened digital networks with the confidence that important, identifying, and critical contents in that documents, digital files, and data streams is secure and will be seen only by authorized parties. (f) To enable real time simultaneous customization and personalization of selected contents within a data stream to different parties, allowing instant display of the selected content or part of it based on, and tailored made to the status of the user or receiving party. (g) To secure the important and critical contents of a document or digital file by transporting said contents into a separated data stream and removing said data stream to a removed storage memory, while eradicating any copies, temporary caches, or traces of the removed extracts on the original computer or machine. (h) To enable instant return transfer to the display or to another display all or part of extracted content instantly with verification of authorized user. (i) To create a projection of the original document, digital file, data objects within a data stream, or variations of it through combined projection of the splinted data streams, while maintaining separation between the data streams. (j) To create an alternative method for security, instead of encryption, which is secure, cost effective, less time-consuming, and flexible. (k) To enable automatic timed removal of specific content items, automatically or manually selected from a document, digital file, or data objects within a data stream. (l) To enable an automatic timed reconstruction (reconstitution) of the said document, digital file, or data objects within a data stream.

Another object of this invention is as a system and method for automatically creating customized and personalized versions of a document, data object, or data stream. In real time, simultaneous versions of the original are created and altered, then disseminated based on the status of the different users and their access privileges. The system and method enables content management and control by automatically locating content items prioritized by importance, transporting them to a secure memory, and releasing them under explicit controls or preset rules.

Another object of the invention is as a system and method for control, analysis and management of important and prioritized information within documents, files, data object, and data streams. The system and method, enables the processing of all data objects at the time in which they are created or imported into the system. The early stage processing, enables early stage inventorying of prioritized contents as well as early stage pattern recognition. Extracting critical information, such as credit card numbers, last names, first names, social security numbers, phones numbers, transaction dollar amounts and addresses, enables the system and method to aggregate data in categories and analyze the data in different optional methodologies including pattern recognition.

Another object of the invention is as a system and method for comprehensive monitoring of various activities including business activities in real time. With this level of detail, the system and method becomes a management information tool and information/data command and control center. The said system and method can include an alert system, which in effect creates a real time apparatus for command and control of the systems activities. In real time, and at any point in time, the user can get a comprehensive view of different activities including: (a) How many transactions are being processed, their content, their context, identity of the involved parties identity, their profiles, and the personnel involved. (b) How much money is being transacted. (c) When, in terms of dates, relevant to the transaction. (d) Where, in terms of geographical location, the transactions are taking place. (e) Where, in terms of geographical location, monies or goods are being transferred. (f) Which departments in the organization are involved.

Multilevel Security through Sanitization with Reconstruction of Sanitized Content A multilevel security (MLS) technology secures the targeted, filtered content with extraction and dispersal to storage, bypassing the use of classification labels, in order to achieve stronger security of the source document or data. During the process of developing security technologies for defending critical infrastructure, it was discovered that the business model was too complex and there was a need to redefine and create new systems and methods for doing business. As a result, the present invention provides a system and codifies methods and business processes to automatically identify, extract, store critical data (as an input security system) and permit reconstruction of critical data only in the presence of certain security clearances (as the output of the security system).

The invention is a method and process to establish a stronger multilevel security (or MLS) architecture and product, than is currently available. The invention introduces multilevel security through sanitization of critical content of a source or plaintext document (or data object) with the unique ability to reconstruct all or part of the original document in conformance to the classification level of the user. A user with top classification may view the entire document, while a user with a lower level classification will view a sanitized document, tailor made automatically for his clearance level. The invention secures the targeted filtered content of a document, file, or data stream, through extraction and dispersal to storage, bypassing the common use of classification labels in order to achieve stronger security. The invention enables secure document storage and secure message transfers between users and networks with different security classification levels while protecting the information on a need to know basis.

Currently multilevel security MLS systems are using multiple PCs for each user, and using physically separate systems for processing data at each classification level. The inventive system, in several embodiments, eliminates the need for the use of multiple computers. All the documents in the user's PC are automatically secured with a granular classification process generally described above with identification of special security data, extraction from the source document or data object, and then separate storage of the security data. The classified granular content is dispersed to different secure, distributed storage locations. The classification level of a user will determine his right and ability to access and release the stored critical extracted content from the various storage locations for reconstruction. A user with top classification will view the entire document, while a user with a lower level classification will view a sanitized document, tailor made automatically for his clearance level.

Types of government security levels are: Top Secret (TS); Secret (S); Confidential (C); and Unclassified (UC). Business identifies security levels as: Restricted to Management (R, for example, attorney-client privilege); Proprietary (P); Sensitive (S); and Public (P). These MLS security levels may be supplemented with "need to know" classification labels, organizational limits (Army, Navy, DoD) and time limits. Prior art security systems identified each file with: owner, size, date and time of creation and security attributes. The Bell Lapadula (BPL) security model uses concepts such as domination of the MLS security level over both a process and the subject (a data object). Some examples of various processes are read, execute, overwrite, append, write, kill (delete), etc. Some examples of process rules under the BPL model are: NRU—No Read Up (a lower security level cannot read a document at a higher security level); NWD—No Write Down (a higher level cannot write down to a lower MLS level).

The invention herein does not use the "classification labels" of the prior art. Instead it creates a situation in which the user gets access rights to specific distributed storage locations based upon his MLS level, each access right can be classified with a different classification level.

Figure 7A:
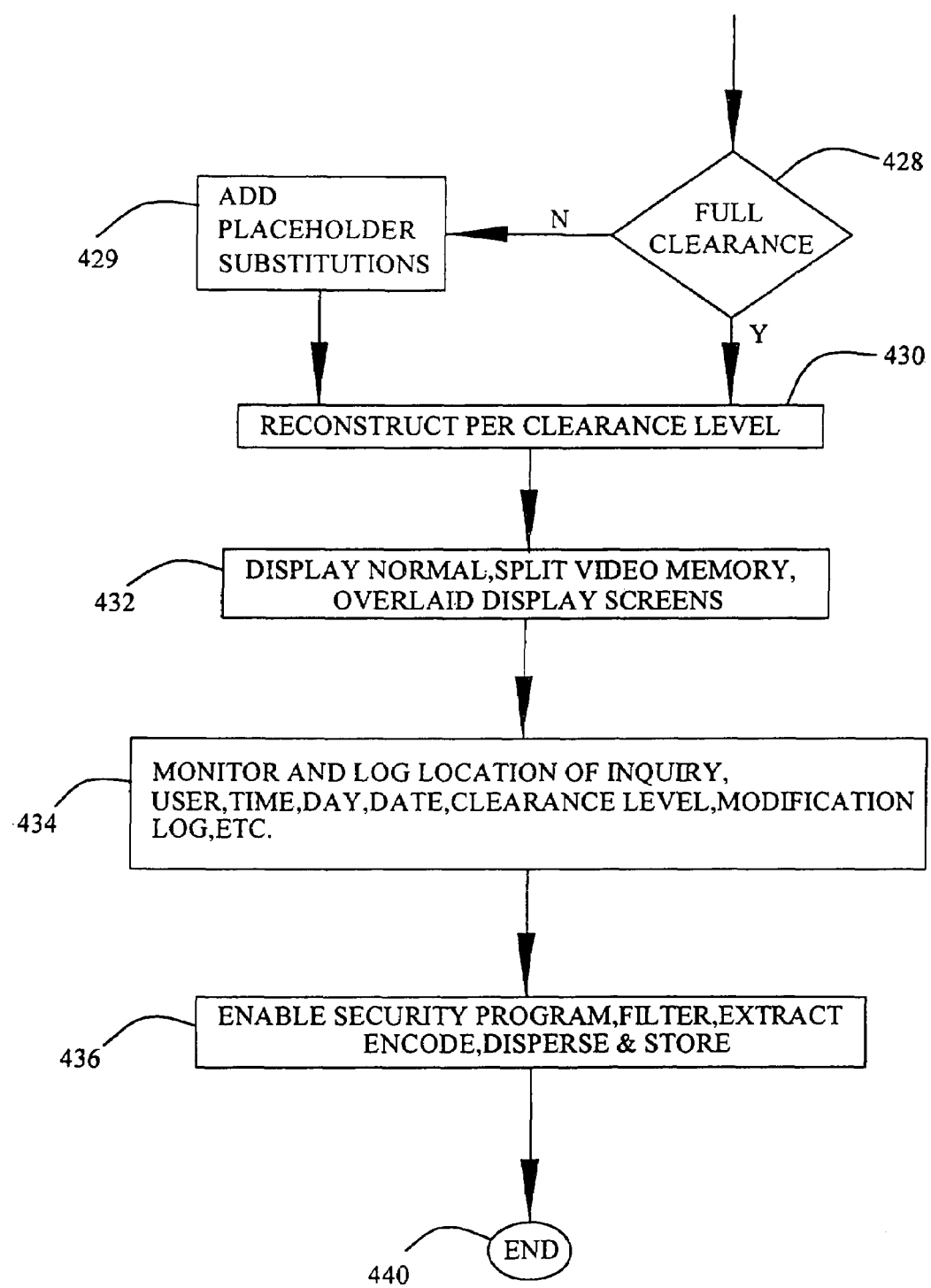
Figure 7B:
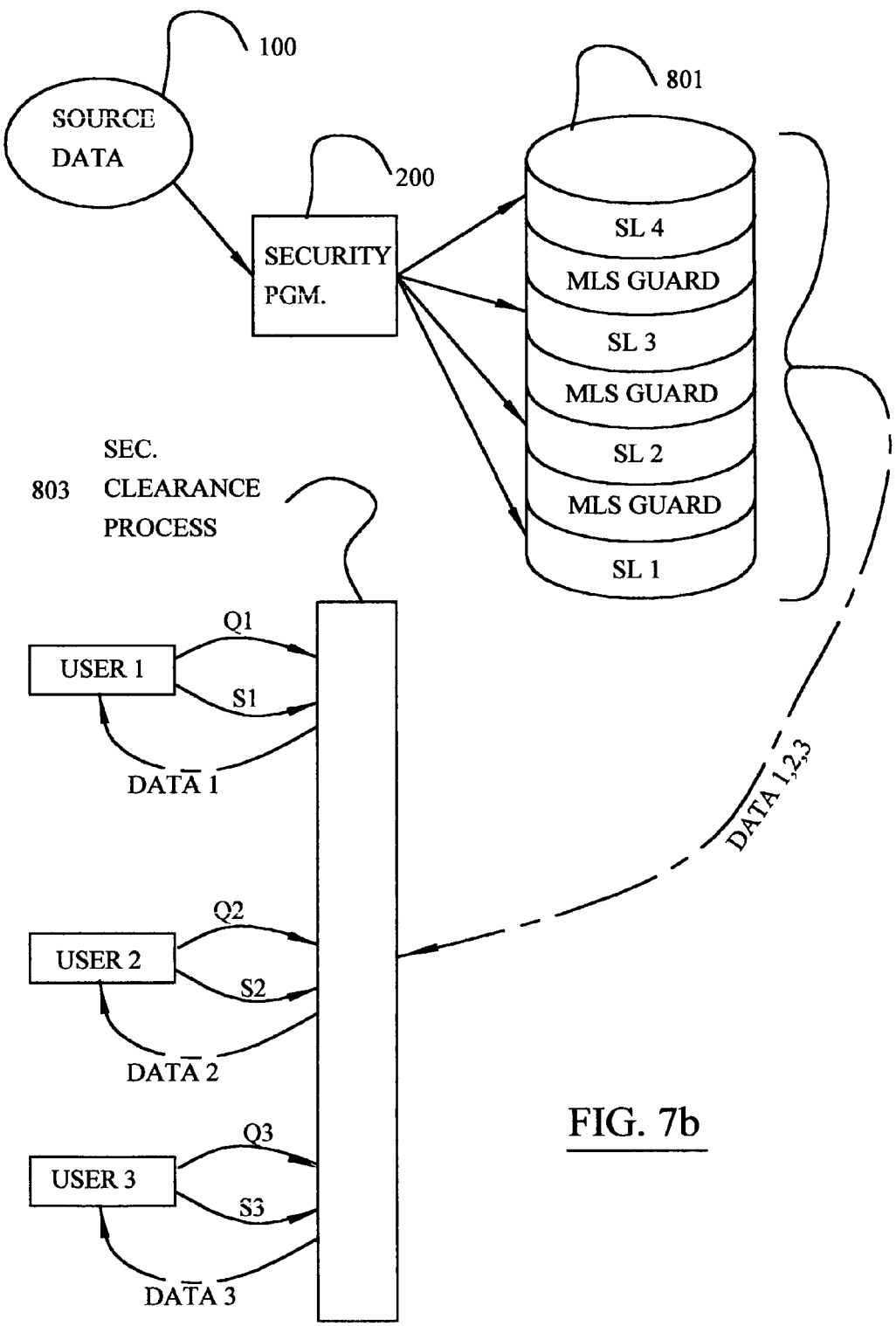
FIG. 7b diagrammatically illustrates a multiple level security system accessed by users having different security clearances (which also represents a data mining system and operation).

FIG. 7b diagrammatically illustrates a multiple level security system accessed by users having different security clearances (which also represents a data mining system and operation). Source data 100 passes through security program 200. Critical, important data objects or elements are extracted and dispersed into storage 801. In the illustrated embodiment, storage 801 has four security levels SL1-SL4, level SL4 being the most secure data requiring the highest security clearance. Between each level is an MLS or multiple level security guard. The guard (physical or software configured) limits transfer of data objects there between. Upon a request or inquiry from user 1, 2 or 3, each having a security clearance s1, s2 or s3, respectively, the query or request for access to data Q1, Q2, or Q3 is sent to security clearance process 803. The process 803 detects and confirms the user's clearance level and passes a cleared query to storage 801. Cleared data (an entire document/data object or a portion thereof or simply one secured data (i.e., a name)), is sent as Data 1, 2 or 3 to clearance process 803. If clearance is still valid, data 1, 2 or 3 is sent to the respective user.

FIG. 7b can be a data mining system in that the user is permitted to mine the "cleared" data from storage 801. Data mining may be a monetary charge associated with the clearance function in process 803.

In a secured system, the documents in the user's PC may be in "declassified" to his security level 99.9% of the time. The "declassified" or available documents are reconstituted through a controlled release of the critical data from storage, and re-classified only when the user presents his identification and his classification level is being verified. Reclassification is automatic at the user's PC. The result is that the user's PC or workstation can operate in classified and unclassified modes. It is unclassified when the documents are declassified and when the documents are reconstituted the user is working in a classified mode.

The invention introduces a new paradigm whereby computers that are classified as secret or top secret, in actuality will contain 99.9% of the time declassified documents. This capability strengthens substantially the security of such classified systems.

The invention can resolve the major challenges facing government in enabling sharing of information between its different organizations in relationship to conducting military operations as well as fighting terrorism. The invention for example can enable organizations connected to the Department of Defense (DOD) or the Homeland Security Department to search into data bases of various other government, state and local organizations, eliminating the fear of the organizations owning the documents that their proprietary data or granular critical data would be released without their specific permission. The invention's mechanism of controlled release of the located document/data enables other parties to search their documents without the fear that sensitive information will be released to the searching party. This invention is designed to foster sharing of documentation between different parties, taking into consideration the need to limit the access of other parties to the total content of the owner's document. The invention enables overcoming the obstacles of existing multiple level security MLS systems by enabling sharing of sensitive data, and granular data between parties in a much more flexible way which also enables much greater access to information not enabled by the current MLS systems. The invention includes a controlled release mechanism for release of data in conformance to benchmarks, which can include submitting of access identification, the giving of consideration, submitting of other information, etc.

The invention creates better collaboration between users and organizations based on a better flow of information. It enables better efficiency enabling easier communication between users and networks with different levels of classification while maintaining the highest levels of security. The invention enables a much better management of documents in storage and in transport including e-mail. The invention introduces automation to the sanitization process and an automatic reconstruction process. The automation will avoid human error both intentionally as well as unintentionally. The automation will enable a substantial reduction in costs, furthermore the ability to create a multilevel security environment in one PC or workstation will save costs of purchasing operating and maintaining multiple machines as is the current practice.

The challenge of many organizations is in getting mission critical and time sensitive information speedily to the users who need it. In many cases the needed non-classified or low-level classified information is stored in systems but is not provided to the user who needs it, because the information is in documents which are highly classified. This creates situations in which users are unable to access information, which they need to accomplish their tasks, because of a technological classification barrier. This over classification of information results in hampering critical tasks and activities, as well as creating system redundancies inefficiencies. The DoD (Department of Defense) multiple level security (MLS) was based upon the Bell-Lapadula (BPL) Model. Many believe that the BLP security model is superior to other models. The Bell-Lapadula Model and the existing MLS uses labels to classify users and subject matter. A professional attacker will use his efforts to change or damage the labels in-order to compromise the machines secured information.

The architecture or the present invention extracts and physically separates data whereby content is being recognized not by labels by automatically based on the semantic content of the plaintext.

In the DoD's MLS, data of multiple security levels are processed and transferred by the system, which separates the varying security levels and controls access to the data. In the prior art MLS system, some applications process only one level of data at a time, (for example, when a user edits a document with a word processing tool, the data in the document are treated as if they were a single level, the classification of the document itself). Other applications treat individual data elements at their actual levels. For example, a word processor enforces paragraph and page MLS classification labels, or an MLS data base brings together data elements of different security levels to allow an analyst a multilevel view of the information.

The vulnerabilities of MLS: The components in the MLS system contain the data in their memories and disks, and the data could be compromised if adequate physical security is not maintained. An attacker who gets access to the system might be able to locate the data or its copies.

MLS guards control the flow of information across security boundaries. These MLS guards are known.

One concern with the Bell-Lapadula Model and the existing MLS is the use of labels to classify users and subject matter. A professional attacker will use all his efforts to change or damage the labels in—order to compromise the machines secured information. The invention introduces an architecture whereby content is being recognized not by labels by automatically based on the semantic contents of the plain text. The invention sanitizes and enables reconstitution upon valid authentication. It is the only architecture and system which enables both sanitization and reconstitution according to user's verified access identification. The conventional way of classifying documents with high classification (TS), limits the low level clearance users (C) from accessing substantially unclassified information "granular data" which is in the classified document. Furthermore, the invention enables maximum sharing of unclassified information which lies dormant in classified documents. Top security-secret information is dispersed to distributed storage in many locations. The invention is designed to avoid any one point of failure. The theory behind the architecture is the creation of substantial lines of defense in depth. The attacker will need to break through many obstacles before accessing all the dispersed data of the document. Additional levels of security are provided with multi-type encryption. The system and process introduces the capability to encrypt different parts of a document with different types of encryption. Multi type encryption creates a major barrier to an attacker. Should he wish to break the encryption, he would need many super computers. Should the attacker look for implementation mistakes, even if he finds few, he will still not get access to the total plain text. The inventive system provides flexibility. The system and process delivers flexibility to accommodate changing circumstances. By controlling the level of the granularity, the user can boost the level of security according to changing circumstances. For example, if a competitor becomes a partner the user enables him access to more storage locations, by changing the matrix.

The system and process integrates the Internet for dispersal and hiding of contents. If a party needs more information it could be released granularly. There is no need to release the whole secret document. The system and process does not use labeling but rather extracts the critical to storage. The system avoids situations, in which, attackers may manipulate the labels or the labeling system. Furthermore, the release of information is based on changing circumstances (time, location-GPS, event).

The invention is a machine and process and its purposes and advantages may be as follows: (a) To automatically control selection of data objects within a data stream and release them in a controlled method only to authorized parties. (b) To automatically separate data objects within a data stream into two or more digital data streams according to the importance and categorization of contents, through extraction and removal of the prioritized content and its replacement by appropriate placeholders. (c) To automatically control selected contents in E-mail, and enable its release in a controlled method only to authorized parties. (d) To enable users to leverage the growth in computer and telecommunications connectivity and electronic commerce by reducing security risks. (e) To enable users to release documents, digital files, and data streams into closed and opened digital networks with the confidence that important, identifying, and critical contents in that documents, digital files, and data streams is secure and will be seen only by authorized parties. (f) To enable real time simultaneous customization and personalization of selected contents within a data stream to different parties, allowing instant display of the selected content or part of it based on, and tailored made to the status of the user or receiving party. (g) To secure the important and critical contents of a document or digital file by transporting said contents into a separated data stream and removing said data stream to a removed storage memory, while eradicating any copies, temporary caches, or traces of the removed extracts on the original computer or machine. (h) To enable instant return transfer to the display or to another display all or part of extracted content instantly with verification of authorized user. (i) To create a projection of the original document, digital file, data objects within a data stream, or variations of it through combined projection of the splinted data streams, while maintaining separation between the data streams. (j) To create an alternative method for security, instead of encryption, which is secure, cost effective, less time-consuming, and flexible. (k) To enable automatic timed removal of specific content items, automatically or manually selected from a document, digital file, or data objects within a data stream. (l) To enable an automatic timed reconstruction (reconstitution) of the said document, digital file, or data objects within a data stream.

The invention differs from the current implementations of multilevel security MLS systems based on the Bell-Lapadula Model, and the prior art use of labels to classify users and subject matter. A professional attacker will use all his efforts to change or damage the labels in—order to compromise the machines secured information. The present invention introduces an architecture whereby content is being recognized not by labels by automatically based on the semantic contents of the plain text. The invention enables overcoming the obstacles of existing multiple level security systems by enabling sharing of sensitive data, and granular data between parties in a much more flexible way which also enables much greater access to information not enabled by the current MLS systems. The invention includes a controlled release mechanism for release of data in conformance to benchmarks, which can include submitting of access identification, the giving of consideration, submitting of other information, etc. The invention creates better collaboration between users and organizations based on a better flow of information. It enables better efficiency enabling easier communication between users and networks with different levels of classification while maintaining the highest levels of security. The invention enables a much better management of documents in storage and in transport including e-mail. The invention introduces automation to the sanitization process and an automatic reconstruction process. The automation will avoid human error both intentionally as well as unintentionally. The automation will enable a substantial reduction in costs, furthermore the ability to create a multilevel security environment in one PC or workstation will save costs of purchasing operating and maintaining multiple machines as is the current practice.

Adaptive Data Security

The present invention can also be configured as an adaptive security program which adapts and adjusts the security provisions based upon intrusion into a particular network or attempts to electronically attack or hack into that network or successful hack events. Programs are available to track electronic attacks or hacking attempts. One of these programs is manufactured by Cisco and identified as the Cisco Intrusion Detection System (IDS). The Cisco IDS system can work on a server or on PCs in a network. The Cisco IDS is an electronic intrusion detector, or an electronic attack detector or a hacking monitor. The hack or attack monitor is software loaded into a designated computer.

The output of the electronic attack or hacking monitor loaded into PC 142 (FIG. 2) for example, or loaded into PC-6 acting as a server for Network A 404 in FIG. 6, generates a plurality of attack warnings. The attack warnings progressively and incrementally indicate the severity and degree of intrusion and hacking attacks directed to the computer system. The following Security Level Table illustrates an example of various responses to increasing levels of attacks. These increasing security responses include engaging the filter and extracting critical data and storing it locally; the next level involves storing the critical data on removable storage media; the next higher level involves offsite storage of all security data; the subsequent security alert results in multiple offsite storage for multiple levels of security or critical data and the highest level involves offsite storage of both common data (remainder data) and security data. Of course, other combinations responsive to the hack attack may be provided. The electronic attack monitor may use artificial intelligence AI to (a) assess the severity of the attack, (b) plan an appropriate "secure data" response, (c) select the degree of filter, extraction and/or encryption, and (d) locate secure extract data storage sites. AI or inference machines can ascertain (a) traffic on communications channels, both intra and inter network, (b) storage limit issues, (c) transmission failures in the communications links, and (d) the degree of security necessitated by exterior events, i.e., terrorism alerts, virus alerts, war, data security warnings posted by trusted sources, MicroSoft, Norton, NASA, DoD, CDC, FBI, etc. Higher security alerts trigger the AI security monitor to heighten the security level (or to decrease that security level in view of a reduction or withdrawal of an electronic attack). Aspects of AI systems, inference engines and neural networks are discussed above in conjunction with the AI configured filter. These AI aspects can be utilized with an AI configured security sensor.

Security Level Table

Attack (low threat level) Level One
   engage filter
   local storage—disk drive
   encrypt map
Attack (moderate threat level) Level Two
   same as Level One but use removable storage media (local)
Attack (nominal attack) Level Three
   Engage higher level filter
   Off site storage, single storage for all security data
Attack (moderate attack) Level Four
   Multiple off site storage, multiple levels of security data
Attack (severe attack) Level Five
   Off site storage both common data and security data Hence, the filtering of data is based upon respective ones of the plurality of attack or hack warnings and the extraction of data and degree of extraction is dependent upon respective ones of the plurality of attack-hack warnings. Storage of the extracted data and the remainder data is also based upon the degree of attack which is reflected in the attack-hack warning issued by the monitor.

Figure 8:
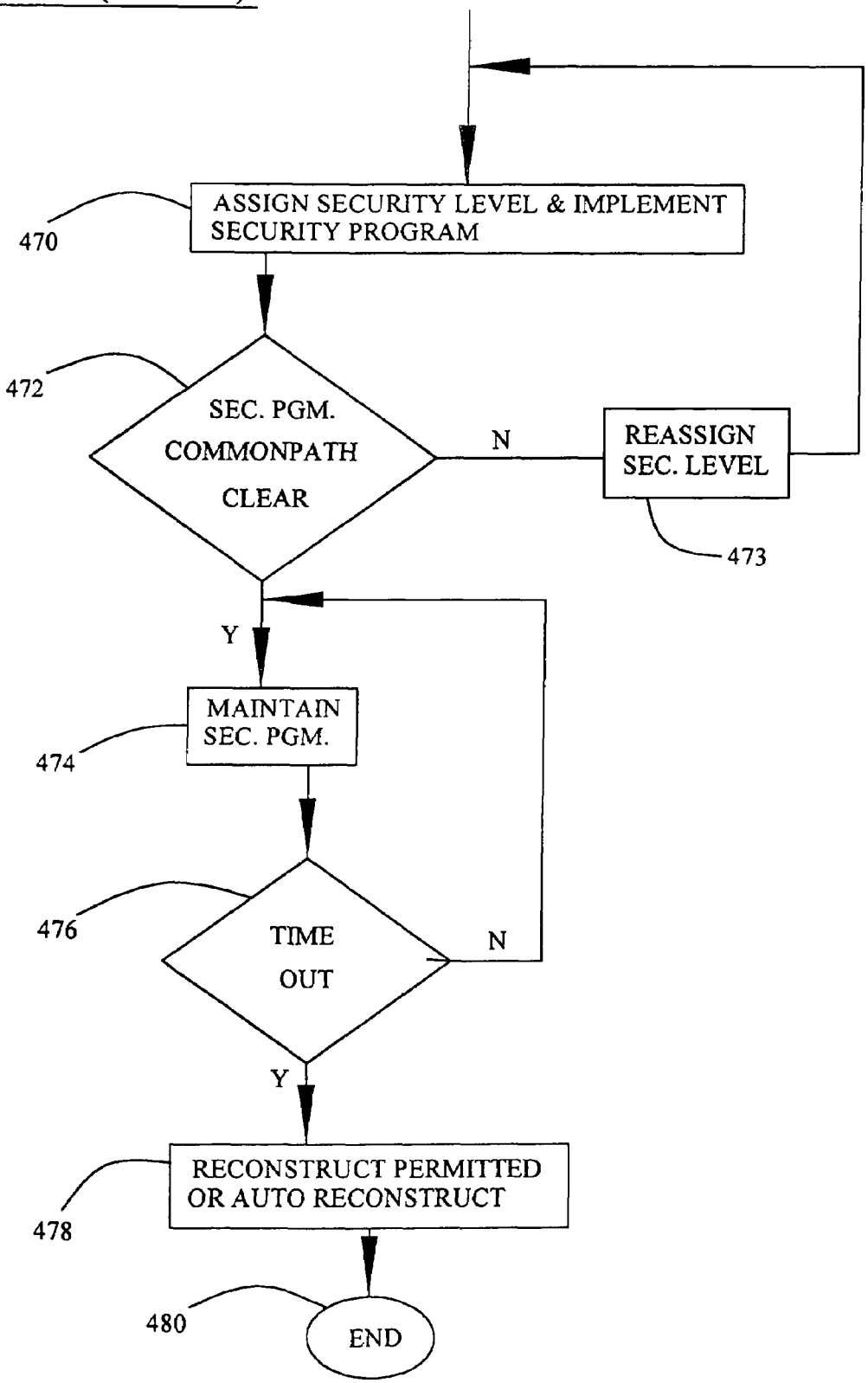
FIG. 8 diagrammatically illustrates a flowchart showing the key components of an adaptive security program adaptable to various levels of electronic attacks, hacker or hack attacks.

FIG. 8 diagrammatically illustrates a flow chart showing the key components of the adaptive security program adaptable to various levels of hacker of electronic attacks. Step 460 senses all intrusions and attempts, that is, electronic attacks, hack attacks or hacking actions on a computer or a computer network. This step is equivalent to the output of the attack-hack monitor. Step 462 assesses the current network performance, adjusts the storage location for the extract data (the location of the extract store), the encryption level (the degree of encryption) and the storage of the map showing the extract data storage (if necessary) and storage of remainder data, if necessary given the severity of the attack. For example, during high utilization of the computer network (high utilization in a server computer in a server-client environment), local storage of extracted data may be preferable as compared with offsite storage of critical data. However, if the attack occurs during non-working hours, the performance of the network is very high, and the security system could utilize all the resources in the computer network to achieve the security goal of safe guarding the data during the attack. System resources include processing resources (for encryption/decryption), bandwidth resources to store extract data and any other resources that are critical for the utilization of the security system described herein. Decision step 464 determines whether a threat or attack as occurred. If not, the system takes the NO branch returns to step 460. If YES, the system in step 466 assigns an attack level or a hack warning level to the threat or attack. The system in decision step 468, monitors the network during the attack. If the network performance or the computer performance does not change, the YES branch is taken. If the computer performance or network performance changes based upon or during the attack, the NO branch is taken and the system returns to step 466 which reassigns an attack level or a warning level to the next higher or significantly higher warning levels.

After decision step 468, the system executes step 470 which assigns the security level and implements the security program based upon the attack. It should be noted that the administrator establishes the degree of security level, the encryption, the extract store and remainder store (if necessary) for various levels of attacks or hack warnings. The security level assigned to a particular attack warning is implemented in step 470. Decision step 472 determines whether the security program's communication path is clear. For offsite storage of extract and/or remainder data, a communication path is important. If the path is blocked or compromised by the attack, the NO branch is taken and the system in step 473 reassigns the security level to a next higher level or a different, safer security level and returns to step 470. If the security and communications path is clear, the YES branch is taken from decision step 472 and, in step 474, the system maintains the security program. Decision step 476 determines whether sufficient time has passed from the attack. If not, the system loops to step 474. If YES, the system executes step 478 which either permits reconstruction of the user operating the plain text or source document or automatically reconstructs those documents that were filtered, parsed, extracted, and subject to outside storage.

The system ends in step 480. To provide additional security, the attack monitor can be configured to monitor security warnings from trusted parties such as MicroSoft, Norton, NASA, DoD, CDC, FBI, etc. Emails or electronic communications from trusted parties can trigger higher levels of security. The attack monitor described above can be configured to accept messages from trusted parties. These messages are equivalent to detecting an electronic attack.

Further, the attack-hack monitor can be configured to monitor and assess other environmental conditions such as fire, power failure, equipment failure, unauthorized physical entry into the building, plant, computer room. These exterior threats or events are monitored by the attack monitor since they may quickly develop into an electronic attack on the secured data retained by the computer system. In response to these exterior events, the attack monitor generates corresponding attack warnings similar in nature to the hack attack warnings discussed above.

There are various methodologies that may be utilized in the adaptive system. The tables that follow set forth these various security methodologies.

| Mode | Normal | Threat | Attack |
|---|---|---|---|
| Standard Automatic Defenses Matrix | | | |
| Encryption | Targeted Encryption | Full Encryption | Multi Type Encryption |
| Extraction | Plain-text Extraction | Extraction of Encrypted Data | Extraction of Multi Type Encryption |
| Distributed Dispersion | Single Storage Location | Several Storage Locations | Many Storage Locations |
| Display | Single display | Color/Dither Protection | Multiple Displays |
| Optional Automatic Defenses Matrix | | | |
| Mode | Normal | Threat | Attack |
| Substitution of Code Words | None | Partial | Many |
| Substitution of Misinformation | None | Partial | Many |
| Controlled Release-Storage | Full | Partial | Conditional |
| Storage Locations | 2 | 4 | 10 or more |
| Time for release | Anytime | Working Hours | Conditional |
| Authorized Users | Many | Partial | Conditional |
| What to Release | All | Partial | Conditional |
| Secret Sharing | None | Two Users | As Configured |

| Security Meter Module Table | | | |
|---|---|---|---|
| | Normal Mode | Threat Mode | Attack Mode |
| ENCRYPTION | Targeted encryption (Secret sharing) | Full encryption (Secret sharing) | Multi layer encryption (Secret sharing) |
| EXTRACTION | Plain-text extraction | Extraction of encrypted Data | Extraction of multi encryption |
| Distributed Storage | 1 critical storage | few critical storage | many critical storage |
| Controlled Release-Storage | Storage # ID Time for release Authorized Users What to release Special conditions | 2 users online | 3 or more users |
| Display | single display | single display | multiple displays |
| Substitution of code words | No | No | No |

| | Extraction Level 1 | Level 2 | Level 3 | Level 4 | Storage Web | Offline | Remote | Removable | Local |
|---|---|---|---|---|---|---|---|---|---|
| Normal Work Mode | | | | | | | | | |
| social security | X | | | | | X | | | |
| credit card | X | | | | | X | | | |
| included | X | | | | | X | | | |
| last name | X | | | | | X | | | |
| number | X | | | | | X | | | |
| telephone | | X | | | | | | X | |
| name | | X | | | | | | X | |
| URL | | X | | | | | | X | |
| e-mail | | X | | | | | | X | |
| uppercase | | X | | | | | | X | |
| initial capital | | X | | | | | | X | |
| currency | | | X | | | | | | X |
| postal code | | | X | | | | | | X |

-continued

|  | Extraction Level 1 | Level 2 | Level 3 | Level 4 | Storage Web | Offline | Remote | Removable | Local |
|---|---|---|---|---|---|---|---|---|---|
| address |  |  |  | X |  |  |  |  | X |
| location |  |  |  | X |  |  |  |  | X |
| date |  |  |  | X |  |  |  |  | X |
| Threat Mode | | | | | | | | | |
| social security | X |  |  |  |  |  |  | X |  |
| credit card | X |  |  |  |  |  |  | X |  |
| included | X |  |  |  |  |  |  | X |  |
| last name | X |  |  |  |  |  |  | X |  |
| number | X |  |  |  |  |  |  | X |  |
| telephone |  | X |  |  |  |  |  | X |  |
| name |  | X |  |  |  |  |  | X |  |
| URL |  | X |  |  |  |  |  | X |  |
| e-mail |  | X |  |  |  |  |  | X |  |
| uppercase |  | X |  |  |  |  |  | X |  |
| initial capital |  | X |  |  |  |  |  | X |  |
| currency |  |  | X |  |  |  |  |  | X |
| postal code |  |  | X |  |  |  |  |  | X |
| address |  |  | X |  |  |  |  |  | X |
| location |  |  | X |  |  |  |  |  | X |
| date |  |  | X |  |  |  |  |  | X |
| Attack Mode | | | | | | | | | |
| social security | X |  |  |  |  | X |  |  |  |
| credit card | X |  |  |  |  | X |  |  |  |
| included | X |  |  |  |  | X |  |  |  |
| last name | X |  |  |  |  | X |  |  |  |
| number | X |  |  |  |  | X |  |  |  |
| telephone | X |  |  |  |  |  | X |  |  |
| name | X |  |  |  |  |  | X |  |  |
| URL | X |  |  |  |  |  | X |  |  |
| e-mail | X |  |  |  |  |  | X |  |  |
| uppercase | X |  |  |  |  |  | X |  |  |
| initial capital | X |  |  |  |  |  | X |  |  |
| currency |  | X |  |  |  |  | X |  |  |
| postal code |  | X |  |  |  |  | X |  |  |
| address |  | X |  |  |  |  | X |  |  |
| location |  | X |  |  |  |  | X |  |  |
| dale |  | X |  |  |  |  | X |  |  |

Another object of the system and method is to enhance the survivability of a system, network, or an organization through distribution of critical information. The objective is to enable a network or organization to carry on its critical missions even while under attacked or damaged. Survivability is the ability of a system to execute its mission and provide critical operational services during and after a successful intrusion or damage. Providing critical operational services includes maintaining availability of information and data such as credit card numbers, names, phone numbers, transaction amounts, shipment details without compromising the security of the information and data.

The invention is designed to enable a network to adapt to ongoing attack and react in a way that permits critical missions to continue. With the current state of the art, when firewalls or other security measures are compromised, no real obstacles curtail or hinder intruders. The system and method is very adaptable and flexible to provide additional layers of security, privacy, anonymity, redundancy, and backup through the selection, extraction, storage, transportation, and reconstruction processes. The dynamic architecture of the invention enables it to conduct an automatic real time configuration of its extraction/transport/recovery activities, in response to the challenge of attacks.

The invention's survivability modes enable: (a) Presetting of rules for computer or network functioning under attack or alert. (b) An automatic assessment of damage and automatic reaction to enable functionality of critical missions.

Multiple Security Features for Data

Figure 9:
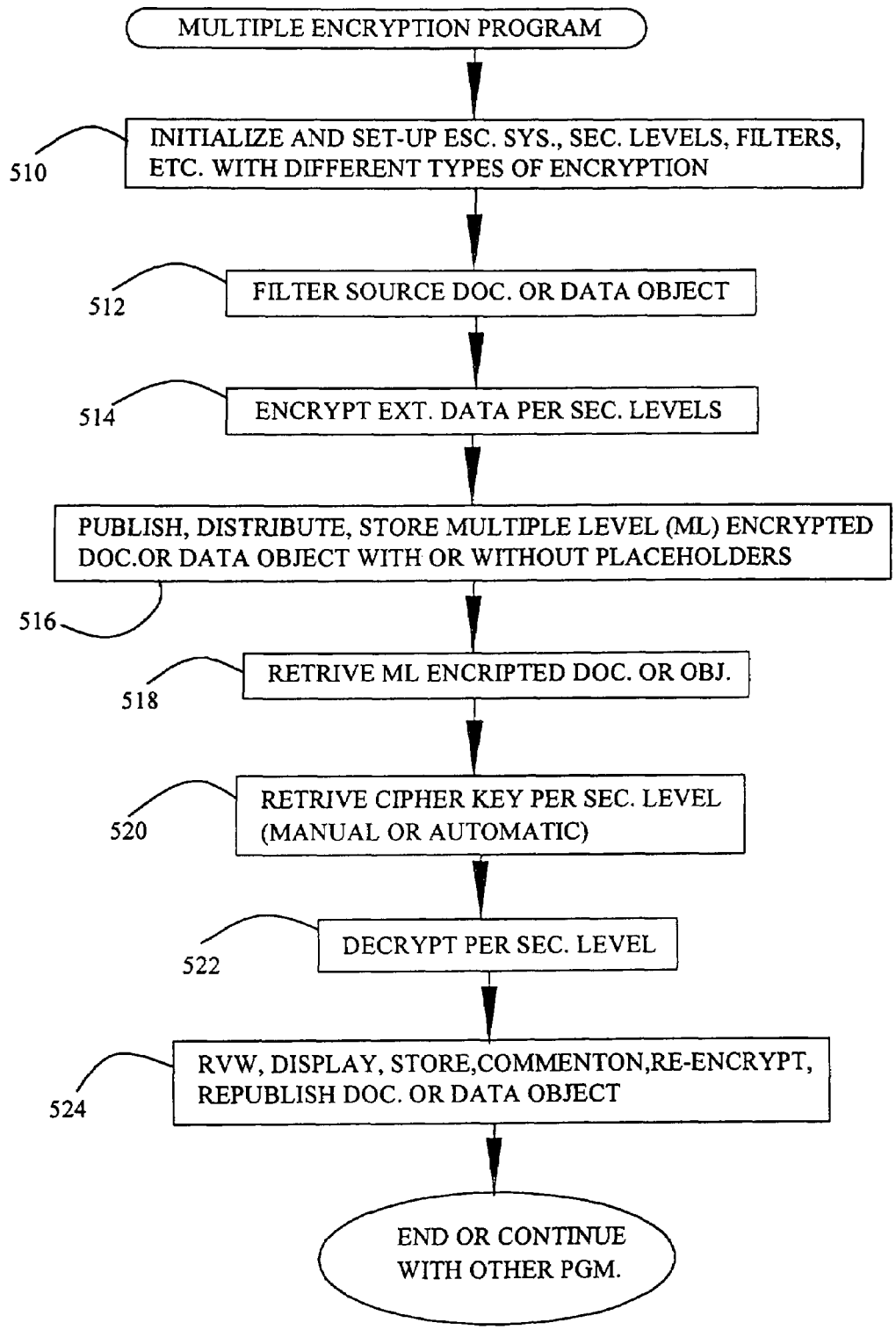
FIG. 9 diagrammatically illustrates a flowchart showing the key components of a multiple encryption program using multiple types of encryption in one document or data object.

FIG. 9 diagrammatically illustrates a flowchart showing the key components of a multiple encryption program using multiple types of encryption in one document or data object. Multiple levels, types or modes of encryption are utilized in the same document or data object to enable securing data and transparently managing the separation of user-based communities of interest based upon cryptographically separated, need to know security levels. These security levels are associated with a plurality of encryption types or with different cipher keys using the same encryption. An example of a multiple level encrypted document is shown above in the Multiple Level Encryption sample. Different levels or modes or types of encryption are listed in the Encryption Table above.

Step 510 in FIG. 9 initializes the system by organizing different security levels with different encryption types and cipher keys. Also, the program sets filters to create the multiple encryption or ML document or data object. Step 512 filters the document or data object. Step 514 encrypts the extracted data for each security level. These steps 510, 512 and 514 utilize many of the routines discussed above in connection with FIGS. 4 and 7, steps 232, 234, 236, 238, 240, 422 and 424. Step 516 recognizes that the secured document or data object may be stored for later use (with associated multiple decryption), published, distributed, or otherwise utilized to achieve the primary purpose of the document, i.e., to communicate information or to safely store security critical information. Step 518 permits the user, with the proper security clearance to retrieve the document or data object. Step 520 illustrates that the user must retrieve his or her cipher key to decode all or a portion of the ML encrypted document or data object. This step may be manual which engages the user to into certain codes or may be automatic such that the user's computer automatically, without operator input, decodes all or part of the document or data object. Step 522 decrypts the document pursuant to the user's security clearance. Step 524 recognizes that the user may review, re-publish, store, comment on, re-encrypt or otherwise deal and handle the full or partially decoded document or data object. The program ends or otherwise continues with other programs set forth herein. It should be noted that storage of the extracted data may be included in the flow path of the program in FIG. 9 is necessary.

Figure 10:
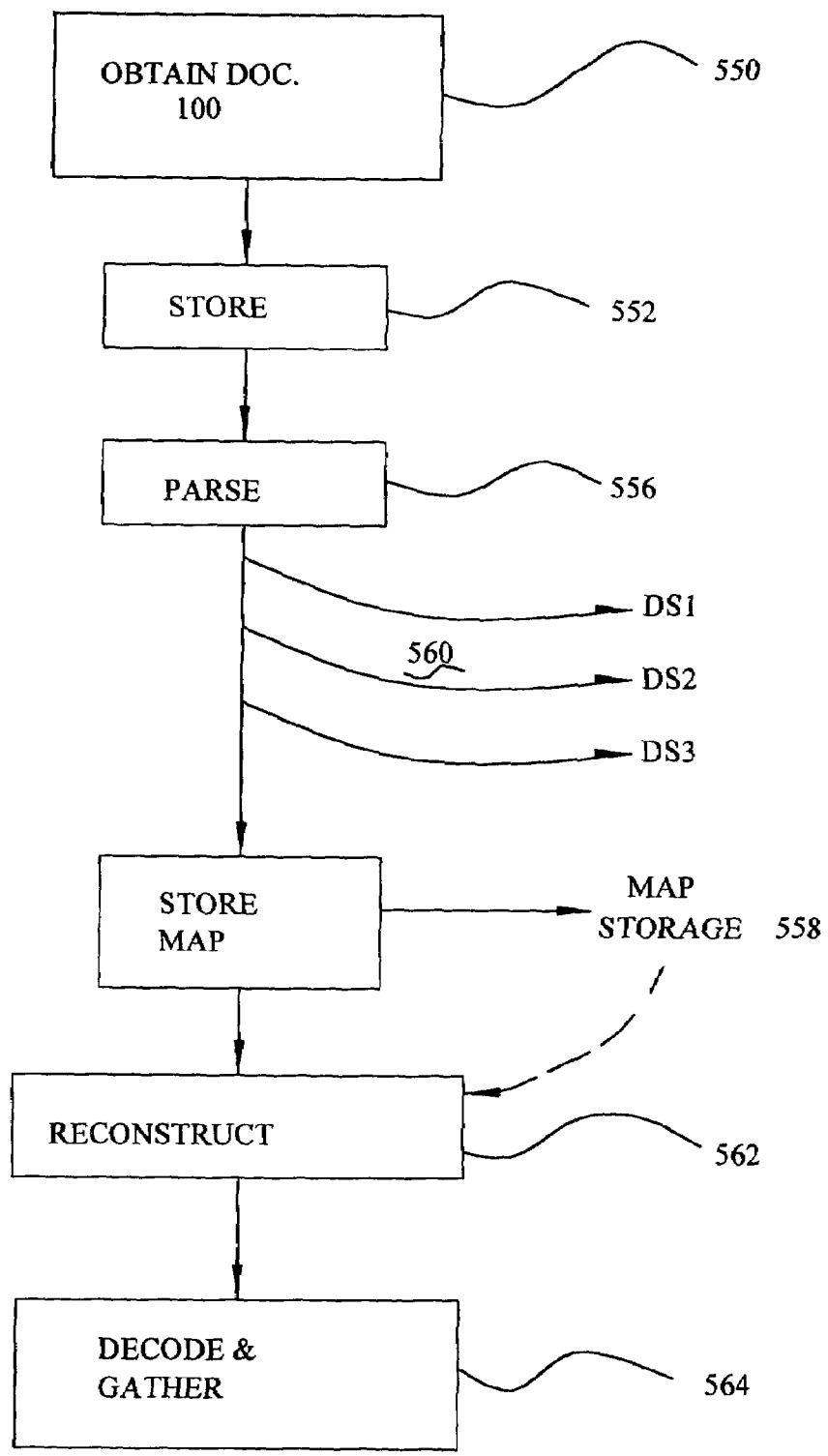
FIG. 10 diagrammatically illustrates a chart showing the key components of the parsing, dispersion, multiple storage and reconstruction (under security clearance) of data.

FIG. 10 diagrammatically illustrates a chart showing the key components of the parsing, dispersion, multiple storage and reconstruction (under security clearance) of data. Document or data object 100, in function element 550, is created or obtained by the input computer device. The document is stored in a normal manner in customary data store 552. A parsing algorithm function 554 is utilized in parsing step 556. The parsing algorithm, as stated earlier, targets the plaintext document or data object 100 and splits, cuts and segments (that is, parses) the document by bit count, word, word count, page, line count, paragraph count, any identifiable document or icon characteristic, or other identifiable feature such as capital letters, italics, underline, etc. Hence, the parsed document 100 constitutes at least remainder data and data which is extracted or parsed or segmented out. A plurality of data extracts may be obtained. The parsed data (which is both the extract data and remainder data) is then dispersed into storage facilities data store DS 1, 2, 3, 4, etc. Preferably, the parsed documents are encrypted as shown by "e" in FIG. 10. In order to facilitate the potential reconstitution of document 100, a map is stored in a map storage 558. Hence, the dispersement 560 largely spreads out or distributes the parsed document 100 to a plurality of memories in the distributed computer system. These memories may be removable memory devices (floppy disc, removable tape drive, CDs) or may be more fixed devices such as hard drives, Internet storage facilities, etc. Preferably, the map is also encrypted.

Reconstruction step 562 enables a person with the appropriate security to obtain the map from map storage 558, decode the map, gather the dispersed, parsed segments of document 100 and compile the document. This is noted in function 564.

Since the original document 100 is stored in a customary manner in data storage 552, the parsed document stored in multiple data storage units DS1-DS4 provides a unique backup for document 100. The algorithm can employ many different mathematical constructions but is, in the current embodiment, primarily based upon one or more of a bit count, a word, a word count, a page count, a line count, a paragraph count, and identifiable document characteristic, and identifiable word characteristic, and identifiable icon characteristic and identifiable data object characteristic, capital letters, italics, and underline found in the plaintext document or data object. Further, the parsing algorithm can generate different security levels wherein parsed segments are stored at different storage facilities having various degrees of security clearance. This establishes a hierarchy of data storage units and corresponding degrees of security clearances. The parsing algorithm may identify unique words or strings of data, i.e., credit card numbers. The hierarchy of security clearances may involve first a password, second a biometric confirmation such as a voice match and a third highly unique biometric characteristic such as a fingerprint or retinal scan. The parsing system enables a large distribution of data in a secured environment. In this manner, if the original data object 100 at customary data storage 552 is destroyed, a person with an appropriate security clearance can reconstitute the original data document 100 due to the secured parsing and dispersal of document 100 through data storage units DS1-DS4 and map storage 558. The parsing may occur on a granular level. In particular, the parsing may occur on a financial document in electronic form.

Financial Document Table

Startcode; Abel, Robert, NMI; 100567; TRANSFER803; To8900586943; FROM3897622891; $700.00; endcode In the Financial Document Table, the start code and end code is typically represented by a digital code unique to the communications channel, the name on the account has no middle initial (NMI) and the various words "transfer 803" and "to 8900586943" and the words "from" and "$" are represented by predefined numeric or alpha numeric codes. The electronic financial document complies with an established protocol. In any event, financial documents are often times transmitted through electronic communications and telecommunications channels. The present invention, in one embodiment, enables a higher level of security by parsing the financial document or data stream. Further, a higher level of security may be employed by extracting identified text or characters and storing the extracted text as discussed above in connection with FIGS. 1A, 1B and 2.

To some extent, the present system can also be utilized for key management and encryption systems.

In a broad sense, the parsing methodology disclosed herein is not based upon the separation of critical versus non-critical or classified versus non-classified security information. The primary focus of the parsing methodology is (1) automatic transparent parsing of data content into granular data groups which are thereafter dispersed to different storage locations in order to maintain a very high level of security with or without encryption; (2) dispersal of the segmented data to different storage locations each which, potentially, demand additional identification or security clearance prior to the release of the stored segmented data, including, possibly, the creation of a digital bureaucracy, in order to hinder or circumvent digital attacks on the plaintext document or data object; (3) proposing and implementing a system wherein the user has a very basic appliance since most of the user's data is stored both locally (customary data storage 552; FIG. 10) and parsed and stored in a distributed system (DS1-DS4) and wherein an important asset is the map stored in map location 558; (4) enabling an institutional system to parse highly confidential information and extract the same in granular form and disperse the same throughout the Internet or other storage locations with or without encryption without compromising the document's security privacy and integrity.

The process involves parsing the documents or content into granular data groups and optionally creating small groups of data wherein the data segments cannot be recognized even to the level of providing 2-4 data objects in each file; dispersing the granular data groups into different storage locations; creation of a map of dispersal to the different storage locations (wherein the map is secured and encrypted and stored); and reconstructing the documents or data content. The reconstruction utilizes the map of dispersed and distributed storage and requires the presentation of security clearances such as passwords, biometric information and/or physical identifiers for access at the storage level and potentially at all the other data storage sites. The data is compartmentalized through distributed storage and sometimes requires separate security clearance. This need for presenting additional security clearance at different storage locations (DS1-DS4) creates a digital bureaucratic process which enhances the security level of the entire system. The selection and extraction of data and dispersal of that data to select storage locations can be established under different criteria. For example, one level of criteria extracts last name, address and social security numbers. Another criteria extracts every other line, every third word, etc. The parsing algorithm can utilize random selection or systematic selection as long as the parsing algorithm is documented and utilized in reconstruct step 562. The parsing algorithm may be stored with map and map store 558 or may be stored separately. An additional feature, as discussed above, involves utilizing place holders or adding substitute content to the remainder data of the parsed document 100. The use of place holders and substitute content may be thought of as an algorithm for the parsing. By using place holders and substitute data, private or highly confidential data is masked insuring privacy, security, and confidentiality. The ability to parse the information and/or extract security information is important for financial transactions. The transactions which require account numbers (see Financial Document Table above) are useless without the account numbers. The security of the account numbers, whether identified and extracted or severely parsed and segmented, stored and reconstituted under security clearances, is enhanced by the present system.

To achieve a very high level of security, the system can optionally incorporate a two-man key system. The system automatically separates the selected data stream into one or more data groups and extracts one or more of these data groups and disperses them into data storage DS1-DS4. To release the extracted data groups and/or critical content, the reconstruct step 562 may require two persons submitting identification credentials or security clearances. This two-man key method is a further protection against identity theft and insider attacks. The two-men key system can be implemented on a regular basis or on an emergency basis when there is need for a higher level of security.

Financial documents sometimes include substantial amounts of numerical data such as financial projections, balance sheets, electronic funds transfer messages, etc. It should be noted that the extraction may be based upon a particular item such a digit and a nine digit number representing money or may be parsed automatically based upon some parsing facility. Of course, the financial document may also be viewed as a data stream with delimiters ";" separating fields in the data stream. The parsing algorithm may work on the data in each field as well as different fields in the entire data stream.

Most storage facility systems require a map in order to reconstruct the original plaintext document 100. The map may be encrypted and may require a secret key sharing scheme for access thereto. Further, the map may be a physical map (a printout) or may be stored on a removable data storage medium, rather than be an electronic representation. In some instances, a map is not necessary. For example, if the security data or the parsed or segmented data were automatically stored on a floppy disc, the originator of plaintext document 100 could move the floppy disc from the computer system thereby physically safeguarding the security data or the segmented, parsed data. Without the disc, another person or the originator of plaintext document 100 could not reconstitute the document. The originator may deliver the floppy disc to another in order to permit reconstitution. The same is true regarding removable tapes and CD-ROMs.

Advantages of the present parsing system, methodology and program, include the ability to connect to unsecured networks without adversely affecting the overall security of the plaintext document 100; less dependence on existing security system including fire walls; the reduction of the requirement to keep daily updates regarding vulnerabilities of the computer system originating plaintext document 100; the security of plaintext document 100 is not dependent upon the number of access points into the network or number of users located on the network originating plaintext document 100; there is no damage to the parsed and stored backup version of plaintext document 100 if new security systems are installed wrong or misconfigured and there is no damage if system administrators turn OFF the existing security systems or improperly install or operate the security systems.

The parsing system can operate as a main security operation or an emergency backup system or as a customary backup system. The plaintext source document or data object may be preserved with or without encryption, or destroyed as a further data security step. The parsing and disbursement of data protects plaintext document 100 and insures the survivability of plaintext document 100 if the system originating plaintext document 100 comes under significant electronic or physical attack. That is, if customary data storage 552 is destroyed electronically or physically, the survivability of data in the plaintext document 100 is established by the present system. The storage of granular data groups most likely would defeat any attempt to view the entire content of plaintext document 100. Only verified user users with a confirmed security clearances or identifications verified at reconstruct step 562 and in data storage sites DS1-DS4 are permitted to reconstruct plaintext document 100. Further, the parsing of the system can be triggered based upon an electronic attack, an electronic hack or a physical environmental detection scheme. This system immediately protects of the critical data plaintext document 100 with a transparent, automatic parsing, dispersal and storage system.

It should be noted that various aspects of the methodology and program described above in connection with FIGS. 1A-9 can be incorporated into the parsing methodology and program in order to enhance or modify the system.

Email, Web-based and Other Types of Applications

Figure 11A:
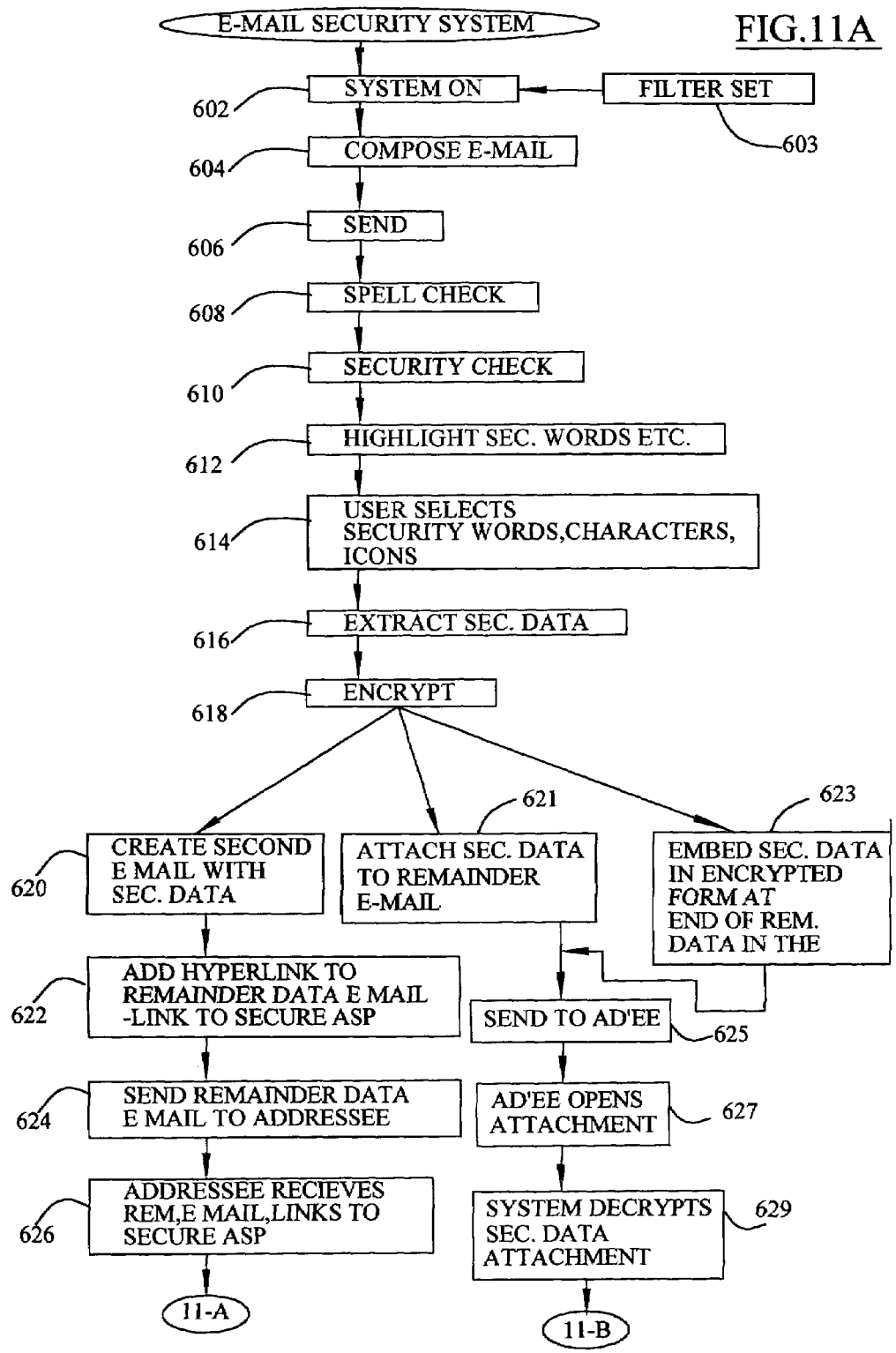
FIGS. 11A and 11B diagrammatically illustrate a flowchart showing the key components of one embodiment of the e-mail security system (jump points 11-A and 11-B link the flow charts).
Figure 11B:
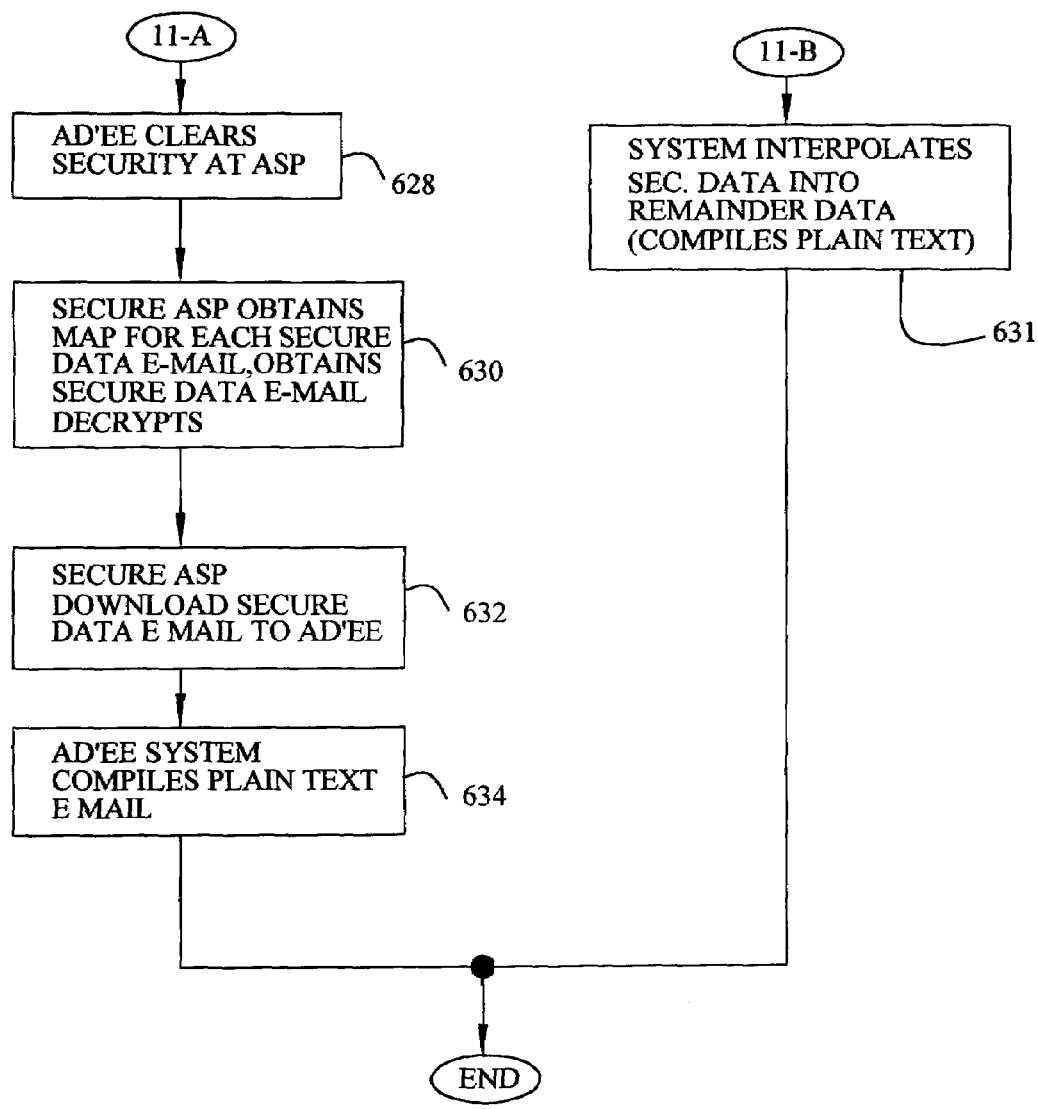

FIGS. 11A and 11B diagrammatically illustrate a flowchart showing the key components of one embodiment of the present invention, that is, an e-mail security system. FIG. 11A is linked to FIG. 11B via jump points 11-A and 11-B. The method of securing e-mail data operates on a distributed computer system which at least includes a remote memory designated as an extract store. Of course, the extract store may comprise a plurality of extract stores operative in conjunction with a plurality of security clearance levels. A singular security level is identified in FIG. 11A. Further, the e-mail may be subject to a parsing algorithm which, as discussed above, is generally independent of the identification of security sensitive data. However, with respect to the parsing aspect of the present invention, the original e-mail data is split into extracted data and remainder data and the extracted data is stored in an extract store. Hence, the parsing algorithm operates essentially independent of the content whereas the secured e-mail program operates based upon content identification. Although FIGS. 11A and 11B primarily relate to identification of security data, the same is true regarding the use of securing e-mail data with a parsing algorithm.

The e-mail security system begins with step 602 wherein the system or program is turned ON or is activated. Step 603 recognizes that the user originating plaintext document 100 (not shown) has set a security filter identifying one or more security sensitive words, characters or icons. In step 604, the user composes the e-mail representative of plaintext document 100. In step 606, the user selects the "send" command in the typical e-mail program. As is customary, the system in step 608 conducts a spell checking routine prior to sending the e-mail. In step 610, the system conducts a security check on the plaintext document or composed e-mail generated in step 604. The filter is used in step 604. In step 612, security words are highlighted or distinguished in the e-mail prior to the actual sending of the e-mail to the addressee. This step 612 is optional. In step 614, the user selects the security words for data to be extracted out. The highlighting step facilitates this selection. In step 616, the system extracts the security data and, preferably, in step 618, the security data is encrypted. Step 618 is optional. In a parsing application to secure e-mail, the parsing algorithm operates automatically at step 610 thereby eliminating steps 612 and 614. The extracting step 616 simply represents that the segmented data obtained from the original plaintext e-mail generated at step 604 is separated from remainder data.

After encryption step 618, the e-mail security system generally operates in one of three manners. Other systems may be formulated based upon the systems and subsystems discussed herein. In one methodology, a second e-mail is created (see step 629), in a second methodology the secured data in encrypted form is attached or appended to the original e-mail containing remainder data (step 621) or, in a third methodology, the encrypted security data is simply added to or inserted into the end of the remainder data of the e-mail (step 623). The methodology of generating a second e-mail is initially discussed.

A second e-mail having encrypted security data is created in step 620. Further, the system in step 622 adds a hyperlink to the remainder data in the original e-mail created in step 604. The hyperlink presents a pointer for the addressee to a secured application service provider or ASP. See the discussion of FIG. 2 above. The ASP represents a data storage facility for the secured e-mail data. In step 624, the remainder data from the original e-mail is sent to the addressee in a normal manner. This step also includes the concept that the second e-mail containing the encrypted security data is sent to the ASP. In step 626, the addressee receives the remainder e-mail which includes a hyperlink to the secured data ASP. The system jumps at jump step 11-A from FIG. 11-A to FIG. 11-B.

In step 628, the addressee receives the remainder e-mail, visits the ASP via the hyperlink and clears the security levels at the secured ASP. In step 630, the secured data ASP obtains a map for each secured data e-mail (since the original e-mail may be broken up into a plurality of extracted, secured data e-mails) obtains all secured data e-mail and decrypts the same. In step 632, the secured ASP downloads the secured data as an e-mail to the addressee. In step 634, the addressee system compiles the original plaintext e-mail 100. A reconstruction program may be necessary to decode the secured data and insert the data into the document via the placeholders.

Optionally, the decryption could occur at the recipient's e-mail device somewhat prior to the reconstitution of the e-mail plaintext document 100 during step 634. This requires the addressee to have the encryption routine and the correct key or decrypt code. The e-mail security system described above may include many of the features discussed earlier in connection with FIGS. 1-9. For example, both the security data and the remainder e-mail data can be encrypted prior to transmission to the addressee and the secured data ASP. The encryption may include multiple levels of encryption and decryption may require multiple levels of security clearance. The encryption may be mixed in the remainder e-mail. Partial as well as full reconstruction is enabled as discussed above in connection with FIG. 3.

From the senders or originator's viewpoint, the e-mail facility described herein facilitates the storage of the extracted data at one or more secured sites.

Another implementation of the secured e-mail system attaches the encrypted and secured data to the remainder e-mail data as indicated in step 621. E-mail attachments are well known. Alternatively, the encrypted secured data may be embedded or copied in encrypted form at the end of the remainder data in the original e-mail as indicated in step 623. In either case, in step 625, the e-mail is sent to the addressee. In step 627, the addressee opens the attachment. In step 629, the system of the recipient decrypts the secured data attachment or the embedded data attachment. In step 631, the recipient's system integrates the now decrypted secured data with the remainder data. Of course, this a compilation step. Place holders or other position indicators are customarily utilized. Appending the encrypted security data is generally equivalent to attaching a file to the original e-mail which constitutes, after extraction, the remainder data. Including the encrypted security data is adding the security data to the original e-mail at a predetermined location (either the top of the e-mail, the bottom of the e-mail or some predetermined line number).

It should be appreciated that the e-mail security system may work automatically or may be selected manually by the user. The highlighting or special distinguishing manner for the security words in step 612 is optional. By highlighting the security words, the user may select or deselect those words for extraction. At the addressee's side, the addressee's system may be configured to automatically seek out the secured data ASP, enter security clearance data, download the secure data and integrate the secure data in the remainder data e-mail. The present invention contemplates automatic as well as manual steps in steps 626, 628, 630, 632 and 634. The hyperlink with the original remainder e-mail essentially maps the remainder data to the secured data and the remote storage locations handling the secure data. Multiple security clearances may be required of the recipient or addressee. The e-mail system can be combined with other features of the security system discussed above such as multiple security data locations, secret key sharing schemes, multiple encryption of the data in a single document, multiple security clearance levels required for a plurality of storage facilities, the two man key system, automation of key management and a plurality of levels of access to the data such as partial reconstruction in step 634 and full reconstruction.

Figure 12A:
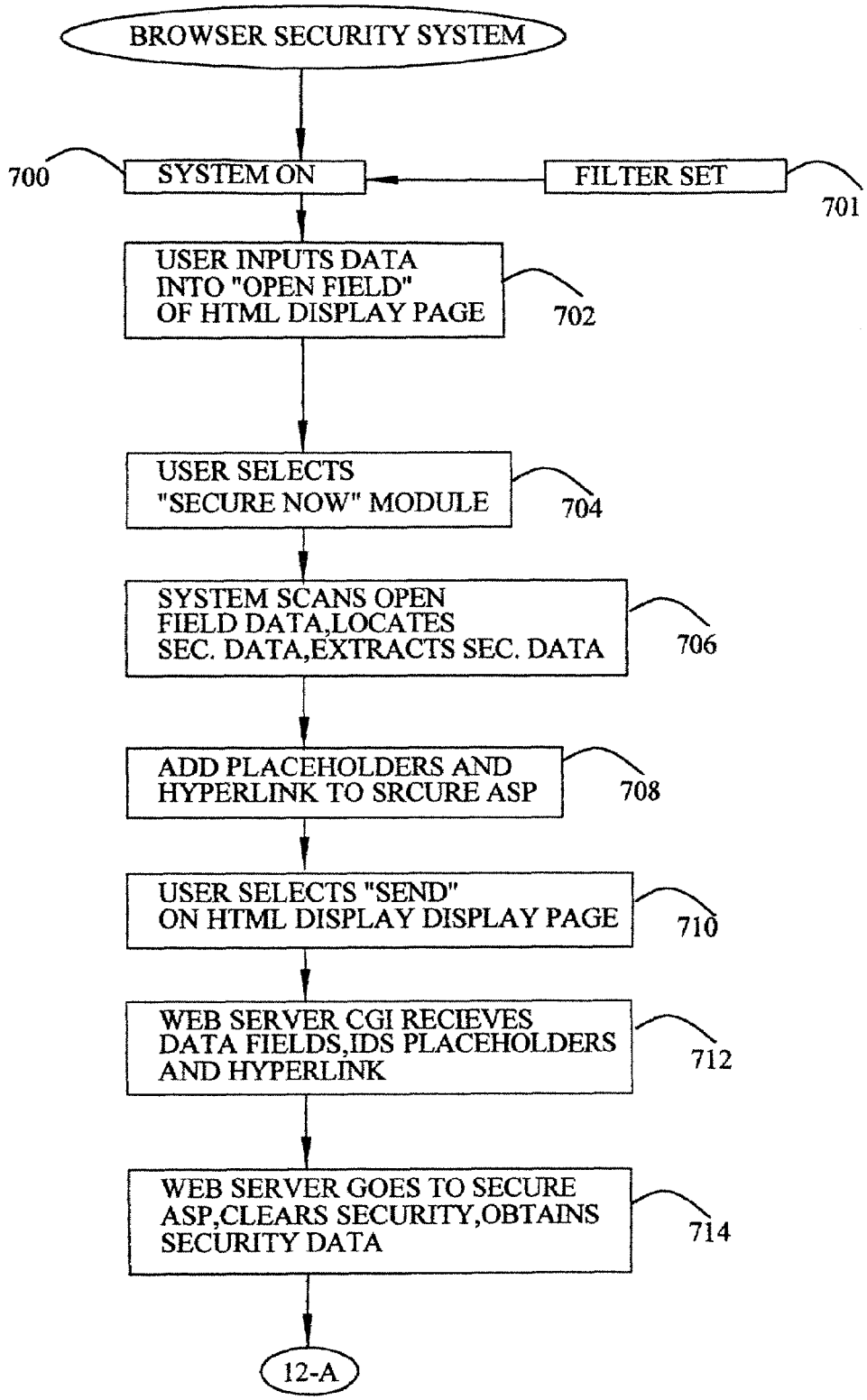
FIGS. 12A and 12B diagrammatically illustrate a flowchart showing the key components of one embodiment of the invention implements the security system on a web browser (jump point 12-A links the flow charts).
Figure 12B:
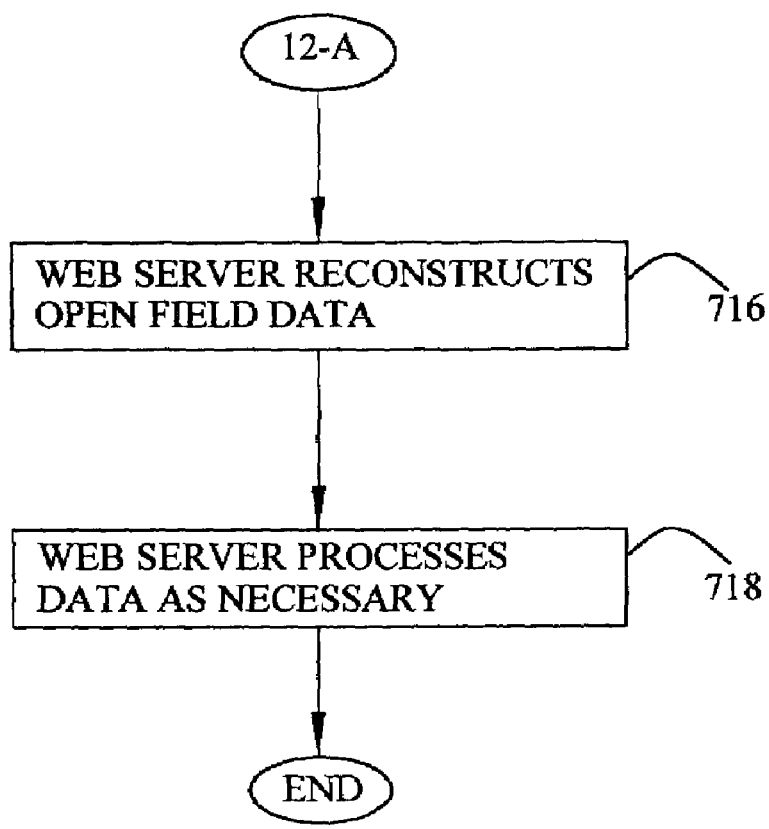

FIGS. 12A and 12B diagrammatically illustrate a flowchart showing the key components of one embodiment of the system and the invention which implements the security system on a web browser. Jump point 12-A links FIG. 12A to FIG. 12B. The system, at step 700 is ON. The filters establishing either the parsing or the identification of security data are established in the filter set step 701. In step 702, the user inputs data into open field of an HTML display page which the user has previously downloaded from a web server. In step 704, the user may select "secure now" turning ON the system or the system may automatically be ON such that the filter is screening all the data input by the user in the open field. In step 706, the system scans all the open field data, locates security data and extracts security data. In step 708, place holders are added to replace the extracted security data in the remainder data and a hyperlink is added to the open field remainder data providing a link to the secure data ASP. In step 710, the user selects the "send button" or any other indicator on the HTML page triggering an operation which transmits the open field data (which is now remainder data) to the web server. In step 712, the web server and particularly the common gateway interface (CGI) receives the remainder data fields, identifies the place holders in the data and the hyperlink to the secure data ASP. In step 714, the web server receiving the data from user's browser goes to the secure data ASP, inputs and clears any security level, and obtains the secured data. In step 716, the web server reconstructs the open field data which generally is represented by plaintext document 100. In step 718, the web server processes the data as necessary. Many of the features discussed above in connection with FIGS. 1A-11A may be implemented on the browser system.

The credit card scrubber or financial data scrubber operates in a similar manner to the email and browser data security system described above. The credit card or financial data scrubber (herein collectively "CC scrubber") typically operates on a defined sequence of numbers. For example, if a credit card number is 17 digits, whenever the email or browser security system or program detects 17 sequential numerical digits (a pre-set filter), a pop-up window may appear enabling the user to select or turn ON the scrubber. If ON, the data security program strips or parses the credit card number and sends, for example, five of the 17 digits to a secure store. Placeholders or substitute characters may be inserted into the remainder CC data. To reconstitute the entire CC data, the intended recipient would be required to pass security clearance levels at the secure store. Of course, the CC scrubber could be set to detect bank account numbers, personal or business account holder names, pre-set passwords, etc. In an OFF state, the CC scrubber would let pass the CC number, account number or pre-set data stream or string. The user may select (i) always ON; (ii) pop-up window, select ON or OFF per transaction; (iii) pop-up window to select OFF (default being ON); or (iv) always OFF but minor reminder (audible sound, icon appearance, etc.) of data security risk. The CC scrubber may encrypt the extracted data for security. Other visual ques may rather than a pop-up window may be used (for example, a drop down menu). The scrubber can also be deployed on wireless devices to scrub sensitive data such as credit card and other financial data.

Figure 13:
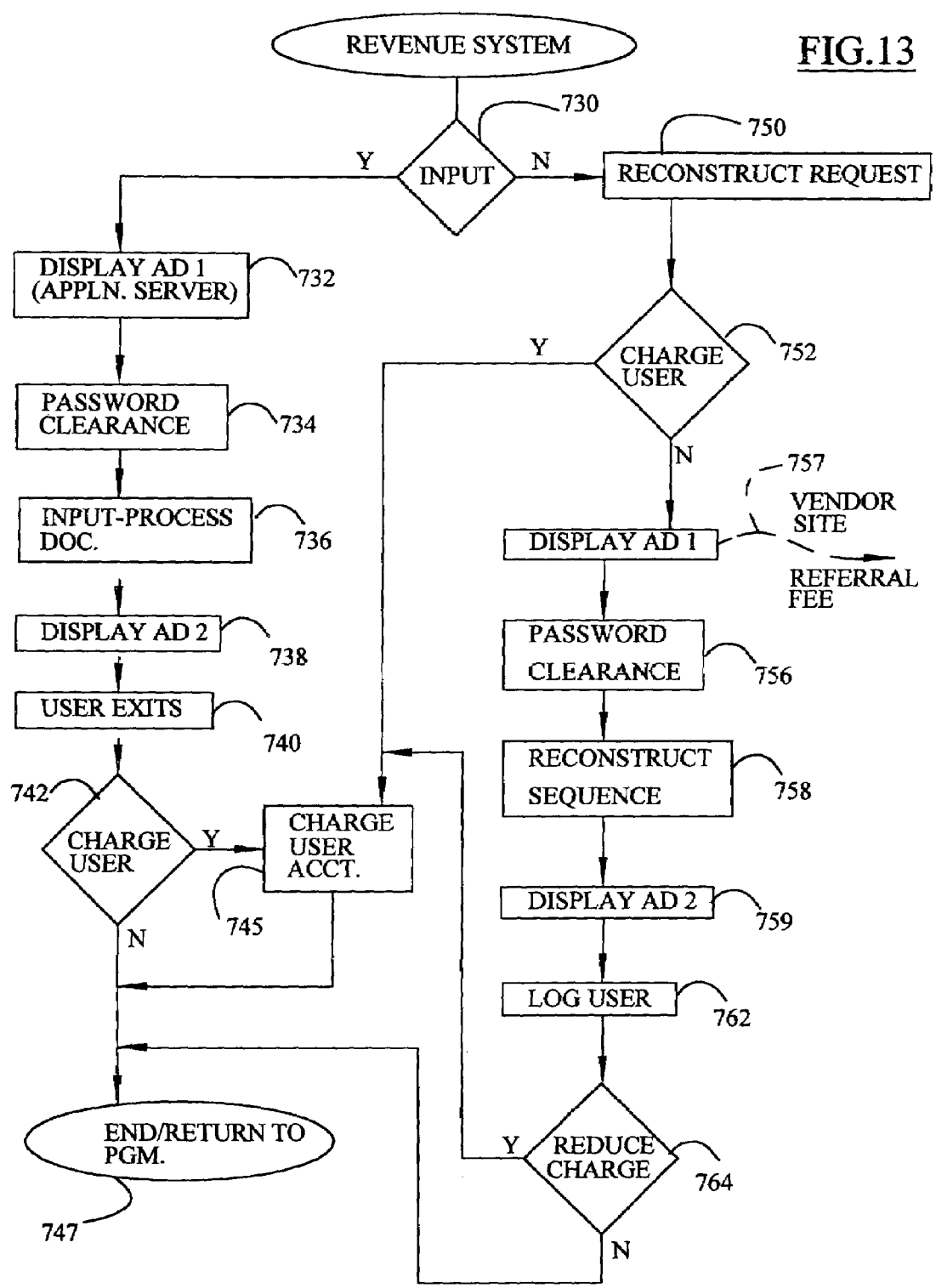
FIG. 13 diagrammatically shows several revenue systems which may be employed with the data security systems described herein.

FIG. 13 diagrammatically shows several revenue systems which may be employed with the data security systems described herein. Many types of revenue systems may be employed in conjunction with the present invention. FIG. 13 shows two basic systems, one at the data input stage and the second at the data output or reconstruction phase. Release of the reconstructed document or portions thereof are based upon security clearance and compensation. Within each revenue subsystem are two types of revenue generators, an advertising revenue generator and a user charge generator. The user charge system contemplates charging or assessing a fee to the user's employer or organization. Therefore, the system operator may select up to four (4) revenue generation systems (ads at the input, charges at the input, ads at the output and charges at the output). It is well known that vendors selling goods and services over the Internet are willing to pay a certain percentage of their sales revenue to other entities referring customers to the vendor's web sites. The concept of display ads in FIG. 13 includes this revenue stream. The system operator may choose all, one, several or none of these revenue systems to be deployed in conjunction with the data security system described earlier herein. Other revenue system may also be utilized. The steps in the revenue system described herein may be reorganized to attain higher consumer and user acceptance and/or to maximize the revenue to the system operator.

Decision step 730 determines whether the system is deployed at the data input phase or not. It is clear that the system operator may utilize the data reconstruction revenue system and hence the decision step 730 is not necessary. If the data input system is employed, step 732 displays the ad to the user. The user may be uploading a complete document to an application server on the Internet or may be using a application service provider on the Internet or an private LAN to secure his or her data. The display ad 732 step enables the user to click on the ad and visit the vendor, thereby potentially generating a referral fee. See referral fee branch 757. Step 734 requires password clearance. Step 736 processes the document or data object with the security system. The user may input the document real time or input it to the application server or may upload the complete document to the server. Alternatively, the ad could be buried in the email or application program run on the user's computer and the user would be shown an ad and given a link to the vendor's Internet site. Selecting the link points the user's browser to the vendor's site.

Step 738 shows display ad 2 to the user thereby potentially generating referral revenue for the system operator. Step 740 notes that the user exits the revenue system. Step 742 determines whether the system charges the user for the security service. If YES, the program processes the charge in step 745 (charge systems are known). If NO, the system ends or returns to other programs in step 747.

The NO branch from determination step 730 leads to the receipt of a reconstruction request by the user in step 750. Step 752 determines whether the user will be charged. If YES, the system executes step 745. If NO, the system displays the ad 1 in step 754. Referral generation is noted by branch 757 from step 754. In step 756, the user's password is subject to clearance. In step 758, the user's request is processed, the document or data object is reconstructed (fully or partially as described earlier), and in step 759 the system displays ad 2. In step 762, the user's activity is logged in to the system. Step 764 determines whether the charge to the user is reduced (because he or she viewed the ads) and if not, the system ends in step 747, if YES, the system processes the charge in step 745. Alternatively, the user may be shown display ads and/or charged for services upon storage of extracted data. Step 750 includes this concept.

The claims appended hereto are meant to cover modifications and changes within the scope and spirit of the present invention.

What is claimed is:

1. A method of securing data based upon a plurality of security levels, each with a predetermined security clearance, in a computer system having a plurality of computers therein and a plurality of memories designated as a remainder store and a plurality of extract stores for respective ones of said plurality of security levels operatively coupled over a communications network, said data having security sensitive content represented by one or more security sensitive words, data objects, characters, images, data elements or icons, comprising:
   extracting said security sensitive content from said data to obtain (a) subsets of extracted data and (b) remainder data;
   storing said extracted data and said remainder data in respective extract stores, corresponding to the respective security level of the extracted data, and said remainder store, respectively; and,
   permitting reconstruction of some or all of said data via one or more of said subsets of extracted data from respective extract stores and remainder data only in the presence of predetermined security clearance for said respective security level corresponding to said respective extract stores.

2. A method of securing data as claimed in claim 1 operating over a plurality of computers interconnected together.

3. A method of securing data as claimed in claim 2 including encrypting said subsets of extracted data with corresponding degrees of encryption associated with said plurality of security levels, and including decrypting, during the reconstruction, of some or all of said subsets of extracted data only in the presence of said predetermined security clearance of said plurality of security levels.

4. A method of securing data as claimed in claim 3 including encrypting said subsets of extracted data and remainder data prior to storing.

5. A method of securing data as claimed in claim 4 wherein the step of extracting utilizes one of an inference engine, neural network and artificial intelligence process.

6. A method of securing data as claimed in claim 5 wherein said reconstruction partially reconstructs said data in response to a query and represents data mining of said data.

7. A method of securing data as claimed in claim 6 including permitting reconstruction of some or all of said data after securing compensation therefor.

8. A method as claimed in claim 7 wherein the step of reconstruction including the step of permitting a plurality of partial reconstructions of said data in the presence of respective ones of said plurality of security clearance levels.

9. A method of securing data as claimed in claim 1 wherein the step of extracting utilizes one of an inference engine, neural network and artificial intelligence process.

10. A method of securing data as claimed in claim 1 wherein said reconstruction partially reconstructs said data in response to a query and represents data mining of said data.

11. A method of securing data as claimed in claim 10 including permitting reconstruction of some or all of said data after securing compensation therefor.

12. A method as claimed in claim 1 wherein the step of reconstruction including the step of permitting a plurality of partial reconstructions of said data in the presence of respective ones of said plurality of security clearance levels.

13. A method as claimed in claim 1 wherein said computer system includes a display fed from video memory having a plurality of frame memory segments, the reconstruction step including interleaving extracted data and remainder data into respective ones of said plurality of frame memory segments.

14. A method as claimed in claim 1 wherein said computer system includes a data display system with at least two separate but visually overlaid displays, the step of reconstruction including displaying said extracted data on one of said at least two displays and displaying said remainder data on another of said at least two displays.

15. A computerized method of securing data based upon a plurality of security levels, each with a predetermined security clearance, in memories designated as a remainder store and a plurality of extract stores for respective ones of said plurality of security levels, said data having security sensitive content represented by one or more security sensitive words, data objects, characters, images, data elements or icons, comprising:
   extracting said security sensitive content from said data to obtain subsets of extracted data and remainder data;
   storing said extracted data and said remainder data in respective extract stores, corresponding to the respective security level of the extracted data, and said remainder store, respectively; and,
   permitting reconstruction of some or all of said data via one or more of said subsets of extracted data from respective extract stores and remainder data only in the presence of predetermined security clearance for said respective security level corresponding to said respective extract stores.

16. A method of securing data as claimed in claim 15 operating over a plurality of computers interconnected together.

17. A method of securing data as claimed in claim 16 wherein said subsets of extracted data are encrypted with corresponding degrees of encryption associated with said plurality of security levels, and including decrypting, during the reconstruction, of some or all of said subsets of extracted data only in the presence of said predetermined security clearance of said plurality of security levels.

18. A method of securing data as claimed in claim 17 including encrypting said subsets of extracted data and remainder data prior to storing.

19. A method of securing data as claimed in claim 15 wherein said reconstruction partially reconstructs said data in response to a query and represents data mining of said data.

20. A method of securing data as claimed in claim 19 including permitting reconstruction of some or all of said data after securing compensation therefor.

21. A method of securing data as claimed in claim 20 wherein said reconstruction partially reconstructs said data in response to a query and represents data mining of said data.

22. A method of securing data as claimed in claim 21 including permitting reconstruction of some or all of said data after securing compensation therefor.

23. A method as claimed in claim 22 wherein the step of reconstruction including the step of permitting a plurality of partial reconstructions of said data in the presence of respective ones of said plurality of security clearance levels.

24. A method as claimed in claim 15 wherein the step of reconstruction including the step of permitting a plurality of partial reconstructions of said data in the presence of respective ones of said plurality of security clearance levels.

25. A method as claimed in claim 15 wherein said computer system includes a display fed from video memory having a plurality of frame memory segments, the reconstruction step including interleaving extracted data and remainder data into respective ones of said plurality of frame memory segments.

26. A method as claimed in claim 15 wherein said computer system includes a data display system with at least two separate but visually overlaid displays, the step of reconstruction including displaying said extracted data on one of said at least two displays and displaying said remainder data on another of said at least two displays.

27. The computerized method of securing data as claimed in claim 15 wherein the method of securing data operates on source data and the method includes storing said source data in addition to extracting, storing said extracted data and permitting reconstruction.

28. The computerized method of securing data as claimed in claim 15 including separating into groups said subsets of extracted data and storing the same in a predefined customized manner in said respective extract store.

29. The computerized method of securing data as claimed in claim 28 including, prior to permitting reconstruction, applying a security clearance protocol on a supplied user's security clearance to determine respective levels of clearance and the respective full or partial reconstruction of some or all of said data.

30. The computerized method of securing data as claimed in claim 29 including, substantially concurrently with permitting reconstruction, logging at least one reconstruction condition from the group of conditions including a location of a user making a reconstruction inquiry, a type of reconstruction inquiry, a chronologic marker for a reconstruction inquiry, said supplied user's security clearance, and said respective security level corresponding to said respective extract stores.

31. The computerized method of securing data as claimed in claim 15 including, prior to permitting reconstruction, applying a security clearance protocol on a supplied user's security clearance to determine respective levels of clearance and the respective full or partial reconstruction of some or all of said data.

32. The computerized method of securing data as claimed in claim 15 including, substantially concurrently with permitting reconstruction, logging at least one reconstruction condition from the group of conditions including a location of a user making a reconstruction inquiry, a type of reconstruction inquiry, a chronologic marker for a reconstruction inquiry, said supplied user's security clearance, and said respective security level corresponding to said respective extract stores.

33. A computer readable storage medium containing programming instructions for securing data based upon a plurality of security levels, each with a predetermined security clearance, in a computer system having a plurality of computers therein and a plurality of memories designated as a remainder store and a plurality of extract stores for respective ones of said plurality of security levels operatively coupled over a communications network, said data having security sensitive content represented by one or more security sensitive words, data objects, characters, images, data elements, or icons, the programming instructions comprising:

extracting said security sensitive content from said data to obtain (a) subsets of extracted data and (b) remainder data;

storing said extracted data and said remainder data in respective extract stores, corresponding to the respective security level of the extracted data, and said remainder store, respectively; and, permitting reconstruction of some or all of said data via one or more of said subsets of extracted data from respective extract stores and remainder data only in the presence of predetermined security clearance for said respective security level corresponding to said respective extract stores.

34. A medium with programming instructions as claimed in claim 33 including programming instructions to store said extracted data and said remainder data over a plurality of computers interconnected together.

35. A medium with programming instructions as claimed in claim 33 including instructions for encrypting said subsets of extracted data with corresponding degrees of encryption associated with said plurality of security levels, and including decrypting, during the reconstruction, of some or all of said subsets of extracted data only in the presence of said predetermined security clearance of said plurality of security levels.

36. A medium with programming instructions as claimed in claim 35 wherein extracting utilizes one of an inference engine, neural network and artificial intelligence process.

37. A medium with programming instructions as claimed in claim 36 wherein said reconstruction partially reconstructs said data in response to a query and represents data mining of said data.

38. A medium with programming instructions as claimed in claim 37 including permitting reconstruction of some or all of said data after securing compensation therefor.

39. A medium with programming instructions as claimed in claim 38 wherein the reconstruction includes permitting a plurality of partial reconstructions of said data in the presence of respective ones of said plurality of security clearance levels.

40. A medium with programming instructions as claimed in claim 33 including instructions for encrypting said subsets of extracted data and remainder data prior to storing.

41. A medium with programming instructions as claimed in claim 33 wherein the extracting utilizes one of an inference engine, neural network and artificial intelligence process.

42. A medium with programming instructions as claimed in claim 33 wherein said reconstruction partially reconstructs said data in response to a query and represents data mining of said data.

43. A medium with programming instructions as claimed in claim 33 including instructions for permitting reconstruction of some or all of said data after securing compensation therefor.

44. A medium with programming instructions as claimed in claim 33 wherein the reconstruction includes permitting a plurality of partial reconstructions of said data in the presence of respective ones of said plurality of security clearance levels.

45. A medium with programming instructions as claimed in claim 33 wherein said computer system includes a display fed from video memory having a plurality of frame memory segments, the reconstruction including interleaving extracted data and remainder data into respective ones of said plurality of frame memory segments.

46. A medium with programming instructions as claimed in claim 33 wherein said computer system includes a data display system with at least two separate but visually overlaid displays, the reconstruction including displaying said extracted data on one of said at least two displays and displaying said remainder data on another of said at least two displays.

47. A computer readable storage medium containing programming instructions for securing data based upon a plurality of security levels, each with a predetermined security clearance, in a plurality of memories designated as a remainder store and a plurality of extract stores for respective ones of said plurality of security levels, said data having security sensitive content represented by one or more security sensitive words, data objects, characters, images, data elements or icons, comprising:

extracting said security sensitive content from said data to obtain (a) subsets of extracted data and (b) remainder data;
   storing said extracted data and said remainder data in respective extract stores, corresponding to the respective security level of the extracted data, and said remainder store, respectively; and,
   permitting reconstruction of some or all of said data via one or more of said subsets of extracted data from respective extract stores and remainder data only in the presence of predetermined security clearance for said respective security level corresponding to said respective extract stores.

48. A medium with programming instructions as claimed in claim 47 operating over a plurality of computers interconnected together.

49. A medium with programming instructions as claimed in claim 48 wherein said subsets of extracted data are encrypted with corresponding degrees of encryption associated with said plurality of security levels, and including decrypting, during the reconstruction, of some or all of said subsets of extracted data only in the presence of said predetermined security clearance of said plurality of security levels.

50. A medium with programming instructions as claimed in claim 49 including encrypting said subsets of extracted data and remainder data prior to storing.

51. A medium with programming instructions as claimed in claim 47 wherein said reconstruction partially reconstructs said data in response to a query and represents data mining of said data.

52. A medium with programming instructions as claimed in claim 51 including permitting reconstruction of some or all of said data after securing compensation therefor.

53. A medium with programming instructions as claimed in claim 52 wherein said reconstruction partially reconstructs said data in response to a query and represents data mining of said data.

54. A medium with programming instructions as claimed in claim 53 including permitting reconstruction of some or all of said data after securing compensation therefor.

55. A medium with programming instructions as claimed in claim 54 wherein the reconstruction includes permitting a plurality of partial reconstructions of said data in the presence of respective ones of said plurality of security clearance levels.

56. A medium with programming instructions as claimed in claim 47 wherein the reconstruction includes permitting a plurality of partial reconstructions of said data in the presence of respective ones of said plurality of security clearance levels.

57. A medium with programming instructions as claimed in claim 47 wherein said computer system includes a display fed from video memory having a plurality of frame memory segments, the reconstruction includes interleaving extracted data and remainder data into respective ones of said plurality of frame memory segments.

58. A medium with programming instructions as claimed in claim 47 wherein said computer system includes a data display system with at least two separate but visually overlaid displays, the reconstruction including displaying said extracted data on one of said at least two displays and displaying said remainder data on another of said at least two displays.

59. A medium with programming instructions for securing data as claimed in claim 47 wherein the program operates on source data and the program includes storing said source data in addition to extracting, storing said extracted data and permitting reconstruction.

60. A medium with programming instructions for securing data as claimed in claim 47 including separating into groups said subsets of extracted data and storing the same in a predefined customized manner in said respective extract store.

61. A medium with programming instructions for securing data as claimed in claim 60 including, prior to permitting reconstruction, applying a security clearance protocol on a supplied user's security clearance to determine respective levels of clearance and the respective full or partial reconstruction of some or all of said data.

62. A medium with programming instructions for securing data as claimed in claim 61 including, substantially concurrently with permitting reconstruction, logging at least one reconstruction condition from the group of conditions including a location of a user making a reconstruction inquiry, a type of reconstruction inquiry, a chronologic marker for a reconstruction inquiry, said supplied user's security clearance, and said respective security level corresponding to said respective extract stores.

63. A medium with programming instructions for securing data as claimed in claim 47 including, prior to permitting reconstruction, applying a security clearance protocol on a supplied user's security clearance to determine respective levels of clearance and the respective full or partial reconstruction of some or all of said data.

64. A medium with programming instructions for securing data as claimed in claim 47 including, substantially concurrently with permitting reconstruction, logging at least one reconstruction condition from the group of conditions including a location of a user making a reconstruction inquiry, a type of reconstruction inquiry, a chronologic marker for a reconstruction inquiry, said supplied user's security clearance, and said respective security level corresponding to said respective extract stores.

65. An information processing system for securing data based upon a plurality of security levels, each with a predetermined security clearance, in a computer system having a plurality of computers therein and a plurality of memories designated as a remainder store and a plurality of extract stores for respective ones of said plurality of security levels operatively coupled over a communications network, said data having security sensitive content represented by one or more security sensitive words, data objects, characters, images, data elements or icons, comprising:

means for extracting said security sensitive content from said data to obtain (a) subsets of extracted data and (b) remainder data;
   means for storing said extracted data and said remainder data in respective extract stores, corresponding to the respective security level of the extracted data, and said remainder store, respectively; and,
   means for permitting reconstruction of some or all of said data via one or more of said subsets of extracted data from respective extract stores and remainder data only in the presence of predetermined security clearance for said respective security level corresponding to said respective extract stores.

66. An information processing system as claimed in claim 65 including means for storing said extracted data and said remainder data over a plurality of computers interconnected together.

67. An information processing system as claimed in claim 65 including means for encrypting said subsets of extracted data with corresponding degrees of encryption associated with said plurality of security levels, and including means for decrypting, during the reconstruction, of some or all of said subsets of extracted data only in the presence of said predetermined security clearance of said plurality of security levels.

68. An information processing system as claimed in claim 65 including means for encrypting said subsets of extracted data and remainder data prior to storing.

69. An information processing system as claimed in claim 65 wherein said means for extracting utilizes one of an inference engine, neural network and artificial intelligence system.

70. An information processing system as claimed in claim 65 wherein said means for reconstruction partially reconstructs said data in response to a query and includes means for data mining said data.

71. An information processing system as claimed in claim 65 including means for permitting reconstruction of some or all of said data after securing compensation therefor.

72. An information processing system as claimed in claim 65 wherein said means for reconstruction including means for permitting a plurality of partial reconstructions of said data in the presence of respective ones of said plurality of security clearance levels.

73. An information processing system as claimed in claim 65 wherein said computer system includes a display fed from video memory having a plurality of frame memory segments, the means for reconstruction including means for interleaving extracted data and remainder data into respective ones of said plurality of frame memory segments.

74. An information processing system as claimed in claim 65 wherein said computer system includes a data display system with at least two separate but visually overlaid displays, the means for reconstruction including means for displaying said extracted data on one of said at least two displays and displaying said remainder data on another of said at least two displays.

75. An information processing system as claimed in claim 67 wherein the means for extracting utilizes one of an inference engine, neural network and artificial intelligence process.

76. An information processing system as claimed in claim 75 wherein said means for reconstruction partially reconstructs said data in response to a query and includes means for data mining said data.

77. An information processing system as claimed in claim 76 including means for permitting reconstruction of some or all of said data after securing compensation therefor.

78. An information processing system as claimed in claim 77 wherein the means for reconstruction including means for permitting a plurality of partial reconstructions of said data in the presence of respective ones of said plurality of security clearance levels.

79. An information processing system for securing data based upon a plurality of security levels, each with a predetermined security clearance, in a plurality of memories designated as a remainder store and a plurality of extract stores for respective ones of said plurality of security levels, said data having security sensitive content represented by one or more security sensitive words, data objects, characters, images, data elements or icons, comprising:

means for extracting said security sensitive content to obtain (a) subsets of extracted data and (b) remainder data;

means for storing said extracted data and said remainder data in respective extract stores, corresponding to the respective security level of the extracted data, and said remainder store, respectively; and, means for permitting reconstruction of some or all of said data via one or more of said subsets of extracted data from respective extract stores and remainder data only in the presence of predetermined security clearance for said respective security level corresponding to said respective extract stores.

80. An information processing system as claimed in claim 79 operating over a plurality of computers interconnected together.

81. An information processing system as claimed in claim 80 wherein said subsets of extracted data are encrypted with corresponding degrees of encryption associated with said plurality of security levels, and including means for decrypting of some or all of said subsets of extracted data only in the presence of said predetermined security clearance of said plurality of security levels.

82. An information processing system as claimed in claim 81 including means for encrypting said subsets of extracted data and remainder data prior to storing.

83. An information processing system as claimed in claim 79 wherein said means for reconstruction partially reconstructs said data in response to a query and includes data mining means for said data.

84. An information processing system as claimed in claim 83 including means for permitting reconstruction of some or all of said data after securing compensation therefor.

85. An information processing system as claimed in claim 84 wherein said means for reconstruction partially reconstructs said data in response to a query and includes means for data mining said data.

86. An information processing system as claimed in claim 85 including means for permitting reconstruction of some or all of said data after securing compensation therefor.

87. An information processing system as claimed in claim 86 wherein the means for reconstruction includes means for permitting a plurality of partial reconstructions of said data in the presence of respective ones of said plurality of security clearance levels.

88. An information processing system as claimed in claim 79 wherein means for reconstruction including means for permitting a plurality of partial reconstructions of said data in the presence of respective ones of said plurality of security clearance levels.

89. An information processing system as claimed in claim 79 wherein said computer system includes a display fed from video memory having a plurality of frame memory segments, the means for reconstruction including means for interleaving extracted data and remainder data into respective ones of said plurality of frame memory segments.

90. An information processing system as claimed in claim 79 wherein said computer system includes a data display system with at least two separate but visually overlaid displays, the means for reconstruction including means for displaying said extracted data on one of said at least two displays and displaying said remainder data on another of said at least two displays.

* * * * *